US012256928B1

(12) United States Patent
Marecki et al.

(10) Patent No.: US 12,256,928 B1
(45) Date of Patent: Mar. 25, 2025

(54) SAFETY CONTROL ALGORITHMS FOR SURGICAL DEVICES, INCLUDING SAFETY CONTROL ALGORITHMS FOR SURGICAL STAPLER DEVICES, AND ASSOCIATED SYSTEMS, DEVICES, AND METHODS

(71) Applicant: LEXINGTON MEDICAL, INC., Billerica, MA (US)

(72) Inventors: Andrew Marecki, Wilbraham, MA (US); Leon Amariglio, Lexington, MA (US); Ali Rezaei, Arlington, MA (US); Gilad Nave Frost, Rosh HaAyin (IL); Keren Sagi, Tel-Aviv (IL); Ilan Krymka, Rosh HaAyin (IL)

(73) Assignee: Lexington Medical, Inc., Bedford, MA (US)

( * ) Notice: Subject to any disclaimer, the term of this patent is extended or adjusted under 35 U.S.C. 154(b) by 0 days.

(21) Appl. No.: 18/391,251

(22) Filed: Dec. 20, 2023

(51) Int. Cl.
*A61B 17/072* (2006.01)
*A61B 17/29* (2006.01)

(52) U.S. Cl.
CPC ............... *A61B 17/07207* (2013.01); *A61B 2017/07271* (2013.01); *A61B 2017/07285* (2013.01); *A61B 2017/2946* (2013.01)

(58) Field of Classification Search
CPC .............................................. A61B 17/07207
See application file for complete search history.

(56) References Cited

U.S. PATENT DOCUMENTS

| | | | |
|---|---|---|---|
| 11,812,961 B2 | 11/2023 | Giordano et al. | |
| 2011/0056715 A1* | 3/2011 | Vanko | H02P 25/145 173/217 |
| 2014/0012289 A1* | 1/2014 | Snow | A61B 17/068 606/130 |
| 2014/0200612 A1* | 7/2014 | Weir | A61B 90/98 227/176.1 |
| 2019/0183502 A1* | 6/2019 | Shelton, IV | A61B 17/07207 |
| 2021/0085316 A1 | 3/2021 | Harris et al. | |
| 2022/0387025 A1 | 12/2022 | Marecki et al. | |
| 2023/0255626 A1 | 8/2023 | Marecki et al. | |

* cited by examiner

*Primary Examiner* — Nathaniel C Chukwurah
(74) *Attorney, Agent, or Firm* — Perkins Coie LLP

(57) ABSTRACT

Safety control algorithms for surgical devices, including safety control algorithms for surgical stapler devices, and associated systems, devices, and methods. In one embodiment, a method of operating a surgical stapler comprises tracking a position of a distal end of a blade assembly of a reloadable cartridge assembly of the surgical stapler as the distal end of the blade assembly is moved, via actuation of a motor and a corresponding drivetrain, along a stroke of the blade assembly. The method can further comprise adjusting a current limit for current levels in the drivetrain based on the position of the distal end of the blade assembly along the stroke.

21 Claims, 24 Drawing Sheets

1410

| Gear | Current | PWN CCR |
|---|---|---|
| 1 | Current Limit A | Target Speed G |
| 2 | Current Limit B | Target Speed F |
| 3 | Current Limit C | Target Speed E |
| 4 | Current Limit D | Target Speed D |
| 5 | Current Limit E | Target Speed C |
| 6 | Current Limit F | Target Speed B |
| 7 | Current Limit G | Target Speed A |

*FIG. 14*

SAFETY CONTROL ALGORITHMS FOR SURGICAL DEVICES, INCLUDING SAFETY CONTROL ALGORITHMS FOR SURGICAL STAPLER DEVICES, AND ASSOCIATED SYSTEMS, DEVICES, AND METHODS

TECHNICAL FIELD

The present disclosure relates generally to safety control algorithms, such as for use in surgical devices. For example, several embodiments of the present technology relate to safety control algorithms for motor-driven surgical stapler devices, and to associated systems, devices, and methods.

BACKGROUND

A surgical handle assembly and/or a surgical reloadable cartridge assembly can be used in a number of surgical devices. One example includes use in—or as part of—a surgical stapler. A surgical stapler is a fastening device used to clamp tissue between opposing jaw structures to join tissue using surgical fasteners. Surgical staplers can include two elongated members used to clamp the tissue. One of the elongated members can include one or more staple cartridges, and the other elongated member can include an anvil that can be used to form a staple when driven from the staple cartridge. Some surgical staplers are equipped with an electric motor that can provide the power to clamp tissue, deliver staples, and provide power for other aspects of a surgical stapler.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. The drawings should not be taken to limit the disclosure to the specific embodiments shown, but are provided for explanation and understanding.

FIG. 14 is a motor virtual gear lookup table in accordance with various embodiments of the present technology.

DETAILED DESCRIPTION

Figure 1:
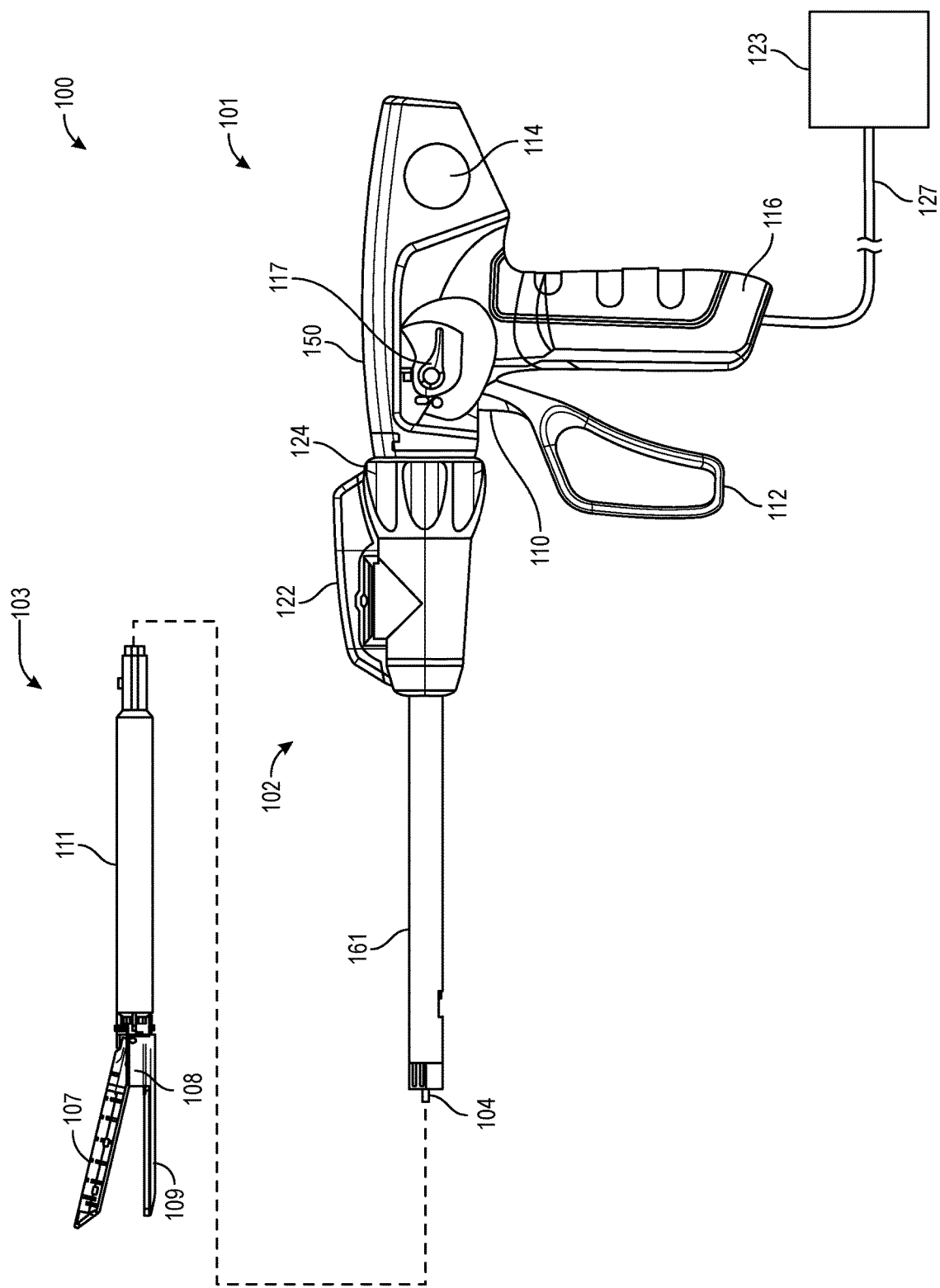
FIG. 1 is a partially schematic diagram of a surgical stapling system configured in accordance with various embodiments of the present technology.

The present disclosure is generally directed to safety control algorithms, such as safety control algorithms for use in surgical stapler devices, and to associated systems, devices, and methods. Specific details of several embodiments of the present technology are described herein with reference to FIGS. 1-23. Although many of the embodiments are described below with reference to safety control algorithms for use in motor-driven surgical stapler devices, other applications and other embodiments in addition to those described herein are within the scope of the present technology. For example, unless otherwise specified or made clear from context, the safety control algorithms of the present technology can be used in or for other devices, such as surgical handle assemblies for other non-stapler medical devices.

It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

As used herein, the term "physician" shall be understood to include any type of medical personnel who may be performing or assisting a medical procedure and, thus, is inclusive of a doctor, a nurse, a clinician, a medical technician, other similar personnel, and any combination thereof. As used herein, the term "patient" and "subject" should be considered to include human and/or non-human (e.g., animal) patients upon which a medical procedure is being performed.

A. OVERVIEW

A surgical stapler can include a surgical handle assembly and a reloadable cartridge assembly. The reloadable cartridge assembly can be releasably attached to the surgical handle assembly. Thereafter, a user can actuate a movable handle of the surgical handle assembly to clamp a first elongated member and a second elongated member of the reloadable cartridge assembly together (e.g., to grip tissue). Once the first elongated member and the second elongated member are clamped together, a user can actuate a power trigger to actuate an electric motor of the surgical handle assembly and a corresponding drivetrain to move a blade assembly in the reloadable cartridge assembly along a stroke of the blade assembly (e.g., to cut and/or staple tissue clamped between the first elongated member and the second elongated member).

A reloadable cartridge assembly can include a single-use lockout assembly that can be triggered or engaged whenever the blade assembly is advanced distally along its stroke by a threshold amount. When the lockout assembly is triggered or engaged, a lockout mechanism of the lockout assembly can pose an obstacle (referred to herein as a "lockout obstacle") to subsequent distal advancements of the blade assembly beyond a point along the stroke of the blade assembly. Such a lockout assembly is used to ensure a single use of the reloadable cartridge assembly (at least until it has been reloaded). Stated another way, once the blade assembly of the reloadable cartridge assembly has been advanced distally along its stroke by the threshold amount, the lockout assembly can be triggered to prevent subsequent reuse or refiring of the reloadable cartridge assembly to avoid accidentally cutting tissue without stapling the tissue.

As tissue is clamped between the first elongated member and the second elongated member, the tissue provides a degree of resistance to distal advancement of the blade assembly along the stroke of the blade assembly. As discussed in greater detail below, the degree of resistance can depend on characteristics of the clamped tissue. In addition, when the lockout assembly is engaged and the lockout mechanism poses a lockout obstacle, the lockout obstacle also provides resistance to distal advancement of the blade assembly beyond a point along the stroke of the blade assembly. Therefore, because attempts to advance the blade assembly beyond a lockout obstacle can result in damage to the reloadable cartridge assembly and/or inadvertent damage to tissue, a motor-driven surgical stapling system must be able to distinguish between (a) resistance to distal advancement of the blade assembly that is provided by tissue (through which the blade assembly can safely pass by cutting and/or stapling the tissue) and (b) resistance to distal advancement of the blade assembly that is provided by a lockout obstruction (through which the blade assembly cannot pass without, for example, risk of damaging the reloadable cartridge assembly and/or inadvertently damaging tissue).

Furthermore, as the blade assembly is advanced to the end of its stroke, the blade assembly can encounter a wall or other stop in the reloadable cartridge assembly 103 that prevents further distal advancement of the blade assembly. The wall or other stop at the end of the stroke for the blade assembly is referred to herein as an end-of-stroke (EOS) obstacle. In some embodiments, a length of the stroke for the blade assembly and/or an exact location of the EOS obstacle may not be known. Therefore, because attempts to advance the blade assembly beyond the EOS obstacle can result in damage to the reloadable cartridge assembly and/or inadvertent damage to tissue, a motor-driven surgical stapling system must be able to quickly detect an EOS obstacle and stall advancement or other movement of the blade assembly that could result in damage to the reloadable cartridge assembly and/or inadvertent damage to tissue.

To address the above concerns, several embodiments of the present technology are directed to safety control algorithms that can adjust power supplied to the motor and/or the speed of the motor as needed to safely cut and/or staple tissue, but that can detect obstacles and stall advancement or other movement of the blade assembly that could result in damage to the reloadable cartridge assembly and/or inadvertent damage to tissue. For example, in some embodiments discussed in detail below, the position of a distal end of a blade assembly can be tracked using an encoder and/or relative to a known, initial position. Thus, as the distal end of the blade assembly approaches or is positioned within a first region along its stroke within which, assuming the lockout assembly has been previously triggered, a lockout obstacle is anticipated to prevent further distal movement of the distal end of the blade assembly along the stroke, the present technology can dynamically set a current limit for current levels in the powertrain and/or a target speed for the motor that is based at least in part on previous current levels observed in the drivetrain as the distal end of the blade assembly approaches or is positioned within the first region. Then, as the distal end of the blade assembly is advanced distally through or across the first region, the system can detect that a lockout obstacle is preventing or hindering further distal movement of the blade assembly along its stroke when a spike in current levels exceeding the dynamically set current limit are observed in the drivetrain (e.g., in combination with little to no change in the tracked position of the distal end of the blade assembly). In turn, the system can stall, cease, or abort further distal advancement of the distal end of the blade assembly along its stroke, and/or can notify a user/operator of the system of the lockout obstacle.

In other embodiments of the present technology discussed in greater detail below, the system can set the motor to a predetermined, preselected, or fixed virtual gear whenever the tracked position of the distal end of the blade assembly indicates that the distal end of the blade assembly is within or approaching the first region (e.g., while being advanced distally). The virtual gear can define a predetermined, preselected, fixed, or static current limit for current levels in the drivetrain and/or a predetermined, preselected, fixed, or static target speed for the motor. In these embodiments, when current levels in the drivetrain exceed the static current limit and/or when a speed of the motor violates the static target speed, the present technology can detect a lockout obstacle; stall, cease, or abort further distal advancement of the distal end of the blade assembly along its stroke; and/or notify a user/operator of the lockout obstacle.

In these and other embodiments, as the distal end of the blade assembly approaches or is positioned within the first region (e.g., within an end portion of the first region) and/or within a beginning portion of a second region following (e.g., positioned distal to) the end of the first region, the present technology can monitor the motor for abrupt speed increases (e.g., that are indicative of a mechanical failure in the surgical stapler, such as a failure of a triggered lockout mechanism of the lockout assembly). In particular, the present technology can compare a rate of change of the speed of the motor and/or a slope of the encoder position to a corresponding threshold value. When the rate of change of the speed of the motor and/or the slope of the encoder position meets or exceeds the corresponding threshold value, the present technology is configured assume that a mechanical failure has occurred; stall, cease, or abort further distal advancement of the distal end of the blade assembly along its stroke; and/or notify a user/operator of the error or likely failure.

In these and still other embodiments, as the distal end of the blade assembly approaches or is positioned within one or more third regions along its stroke within which it is anticipated that the blade assembly may encounter an end-of-stroke (EOS) obstacle that prevents or hinders further distal movement of the distal end of the blade assembly, the present technology can, while the distal end of the blade assembly is (e.g., continuously) positioned in the third region(s), track a number of times (a) a current limit for current levels in the drivetrain is adjusted, s (b) a target speed for the motor is adjusted, and/or (c) a virtual gear for the motor is adjusted. The present technology can compare a tracked number of times to a corresponding threshold number of times. When the tracked number of times reaches or exceeds the corresponding threshold number of times, the present technology can detect an EOS obstacle; stall, cease, or abort further distal advancement of the distal end of the blade assembly along its stroke; and/or notify a user/operator of the EOS obstacle.

In some embodiments, as the distal end of the blade assembly approaches or is positioned within other regions along its stroke (e.g., regions outside of the first region and/or the one or more second regions), the present technology can control a virtual gear of the motor using a lookup table. The lookup table can define a plurality of virtual gears for the motor, with each gear defining a pairing of a current limit for current levels in the drivetrain and a target speed for the motor. In some embodiments, the current limits can be generally inversely related with the corresponding target speeds across the plurality of virtual gears. As the distal end of the blade assembly is moved distally and/or proximally along its stroke, the present technology can adjust the virtual gear of the motor using the lookup table whenever current levels in the powertrain violate the current limit for a present virtual gear of the motor and/or whenever a speed of the motor violates the target speed for the present virtual gear.

B. SELECTED EMBODIMENTS OF SAFETY CONTROL ALGORITHMS FOR SURGICAL DEVICES, AND ASSOCIATED SYSTEMS, DEVICES, AND METHODS

1. Surgical Stapling Systems and Devices

FIG. 1 is a partially schematic diagram of a surgical stapling system 100 ("the system 100") configured in accordance with various embodiments of the present technology. As shown, the system 100 can include a surgical stapling apparatus 101 ("the surgical stapler 101") having a surgical handle assembly 102 and/or a surgical reloadable cartridge assembly 103 (e.g., a disposable loading unit). The surgical reloadable cartridge assembly 103 can be releasably secured to a distal end of an elongated body 161 of the surgical handle assembly 102, such as to a drive shaft 104 of the surgical handle assembly 102.

In the illustrated embodiment, the reloadable cartridge assembly 103 includes a shaft 111, a first elongated member 107, and a second elongated member 109. The first elongated member 107 and the second elongated member 109 can be used to clamp tissue, and are also referred to herein as "jaws." One of the elongated members (e.g., the first elongated member 107) can house one or more staple cartridges. The other elongated member (e.g., the second elongated member 109) can include an anvil that can be used to form a staple when driven from the staple cartridge (e.g., by a blade assembly (not shown in FIG. 1), as discussed in greater detail below). In some embodiments, the reloadable cartridge assembly 103 can further include a stabilizing bracket 108 that can help to hold the first elongated member 107 and the second elongated member 109 in alignment with one another and/or that can function as a tissue shield to prevent or hinder tissue from being clamped between the first elongated member 107 and the second elongated member 109 at a location more proximal than a distal end of the stabilizing bracket 108. In these and other embodiments, the reloadable cartridge assembly 103 can include one or more rows of staples having a linear length. For example, a row of staples can have a linear length between approximately 30 mm and approximately 60 mm. In a number of embodiments, third party reloadable cartridges and/or reloadable cartridge assemblies may be used with the surgical handle assembly 102 and embodiments of the surgical handle assembly 102 may be configured to receive the same.

The surgical handle assembly 102 can include a radial positioner 124, an articulation assembly activated by an articulation knob 122, a non-movable handle 116 ("the stationary handle 116"), and a movable handle 112. When the reloadable cartridge assembly 103 is releasably secured to the distal end of the elongated body 161 of the surgical handle assembly 102, the reloadable cartridge assembly 103 can be actuated using the articulation knob 122 and/or the radial positioner 124 to reach a stapling site. For example, the radial positioner 124 can be used to rotate the reloadable cartridge assembly 103. Additionally, or alternatively, the articulation knob 122 can be used to position the first elongated member 107 and/or the second elongated member 109 at a particular angle for stapling. The articulation knob 122 can be rotationally actuatable, and the reloadable cartridge assembly 103 can rotate about an axis of a particular plane in response to the articulation knob 122 being rotationally actuated by a physician. The movable handle 112 can be used to clamp and unclamp the first elongated member 107 and the second elongated member 109 together (e.g., to clamp or grip tissue).

As shown, the surgical handle assembly 102 further includes a power trigger 110, a selector lever 117, and a manual retraction or bailout handle 150. The power trigger 110 can be used to activate an electric motor (not shown in FIG. 1) of the surgical handle assembly 102 to move a gear rack (not shown in FIG. 1) distally. The selector lever 117 can include a number of settings, which can include a locked position (e.g., a safety-activated position), an unlocked position (e.g., a fire position, a safety-deactivated position), and a reverse position. While the selector lever 117 is in the locked position, the movable handle 112 may be used to clamp and unclamp the first elongated member 107 and the second elongated member 109 together, but the power trigger 110 may be electrically deactivated or disabled such that actuation of the power trigger 110 does not activate the electric motor. When the selector lever 117 is in the unlocked position, the power trigger 110 may be enabled such that actuation of the power trigger 110 can supply power to the electric motor (e.g., to move the gear rack distally). When set to the reverse (e.g., retract) position, the selector lever 117 can cause the electric motor to be activated (e.g., to move the gear rack proximally). In some embodiments, the reverse position of the selector lever 117 can be a momentary position. Although not shown in the illustrated embodiment, the surgical handle assembly 102 can include a safety switch and a reverse button that are separate from one another (e.g., in addition to or in lieu of the selector lever 117) in other embodiments of the present technology.

In the illustrated embodiment, the surgical handle assembly 102 also includes a manual retraction or bailout handle 150. The bailout handle 150 can be used, for example, in the event the surgical stapler 101 or another component of the system 100 malfunctions, such as to manually open or separate the first elongated member 107 and the second elongated member 109 away from one another such that they no longer clamp tissue.

In some embodiments, the surgical handle assembly 102 can include a user feedback mechanism 114 that is usable to audibly or visually alert or inform a physician of one or more statuses of the system 100 (e.g., of the surgical handle assembly 102 and/or the surgical stapler 101). In the illustrated embodiment, the user feedback mechanism 114 includes a visible indicator, such as a LED. In some embodiments, the user feedback mechanism 114 can, for example, emit various colors to inform a physician of various states of the system 100. As a specific example, the user feedback mechanism 114 can emit a steady (e.g., non-flashing) green color to inform a physician when everything is fine; a flashing green color when the surgical handle assembly 102 is in the ready to fire position; a yellow color when a possible obstruction is detected, when the electric motor has stalled, and/or when the drivetrain is stopped for an obstruction, such as at an end of a firing stroke or upon encountering an actuated single use lockout mechanism; and/or a red color when a major system error or safety issue is detected. In some embodiments, the user feedback mechanism 114 can additionally, or alternatively, emit one or more sounds (e.g., beeps) that can, for example, change in pitch or frequency to inform a physician of certain events or statuses. Although illustrated on a side of the surgical handle assembly 102, the user feedback mechanism 114 can be positioned at other locations on the surgical handle assembly 102 in other embodiments of the present technology, such as on a top or bottom of the surgical handle assembly 102.

Although not shown in FIG. 1, the surgical handle assembly 102 can include a power source, such as a battery. The power source (e.g., battery) can be rechargeable (e.g., via an AC power supply) or disposable. If a rechargeable battery is used, the battery can be positioned so that it can be either removed or recharged. If a disposable battery is used, the stationary handle 116 can include a drain so that the battery can be drained prior to disposal.

In these and other embodiments, the surgical handle assembly 102 can include or be (e.g., releasably) coupled to a power cord 127. For example, the power cord 127 can be used to electrically couple the surgical handle assembly 102 (e.g., a battery and/or an electric motor of the surgical handle assembly 102) to a power source 123 positioned outside of the surgical handle assembly 102. In turn, the power source 123 can supply AC or DC current to the surgical handle assembly 102 to power various electronics of the surgical handle assembly 102. If AC power is used, a power converter can be used to convert 120V or 240V AC, at either 50 or 60 Hz, to 24V, or any other suitable voltage, DC.

Figure 2:
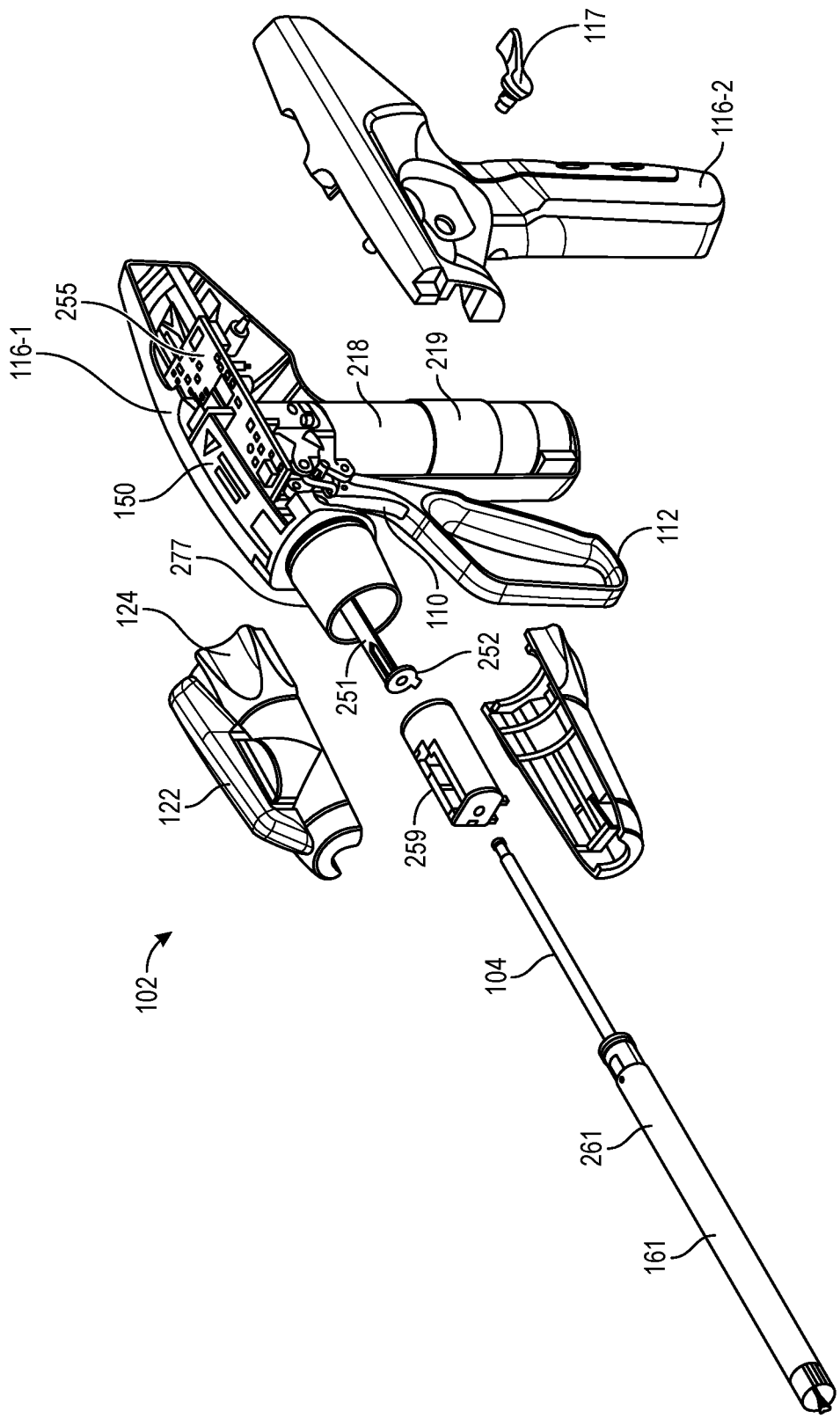
FIG. 2 is a partially schematic, partial exploded view of a surgical handle assembly configured in accordance with various embodiments of the present technology.

FIG. 2 is a partially schematic, partial exploded view of the surgical handle assembly 102 of FIG. 1. As discussed above, a distal portion of the surgical handle assembly 102 can include the articulation knob 122 and the radial positioner 124. The drive shaft 104 (e.g., drive rod) can cooperate with a gear rack (not shown in FIG. 2) to effect movement for a reloadable cartridge assembly (e.g., the reloadable cartridge assembly 103 of FIG. 1).

FIG. 2 illustrates a first handle half 116-1 and a second handle half 116-2 that together provide the stationary handle 116 for a user of the surgical handle assembly 102 and that together house a drivetrain 218 and/or other electrical and mechanical mechanisms of the surgical handle assembly 102. The first handle half 116-1 and/or the second handle half 116-2 may also include components that are used in the clamping and/or unclamping of the jaws.

In some embodiments, the drivetrain 218 can include a number of gears (not shown in FIG. 2) and/or a power source (not shown), such as a battery. As discussed in greater detail below, the drivetrain 218 includes an electric motor 219. The electric motor 219 can be battery-powered and/or can be connected to an external power source (e.g., the power source 123 of FIG. 1). In these and other embodiments, the drivetrain 218 can include the electric motor 219 and a number of gears, and a battery can be located elsewhere (e.g., another position between the first handle half 116-1 and the second handle half 116-2). As discussed in greater detail below, the gear rack can interact with the drivetrain 218, and the drive shaft 104 can be coupled to a distal end of the gear rack.

The power trigger 110 and the selector lever 117 can be used to activate the drivetrain 218. The movable handle 112 can be used to clamp and unclamp the first elongated member 107 (FIG. 1) and the second elongated member 109 (FIG. 1) together, and the selector lever 117 can allow power to flow to the electric motor and/or block the power trigger 110 from being activated. Also shown in FIG. 2 is an outer shaft 261 of the elongated body 161, a nose cone 277, the bailout handle 150, a circuit board 255, an articulation lock 259, toggle plates 252, and a bailout bar 151.

Figure 3:
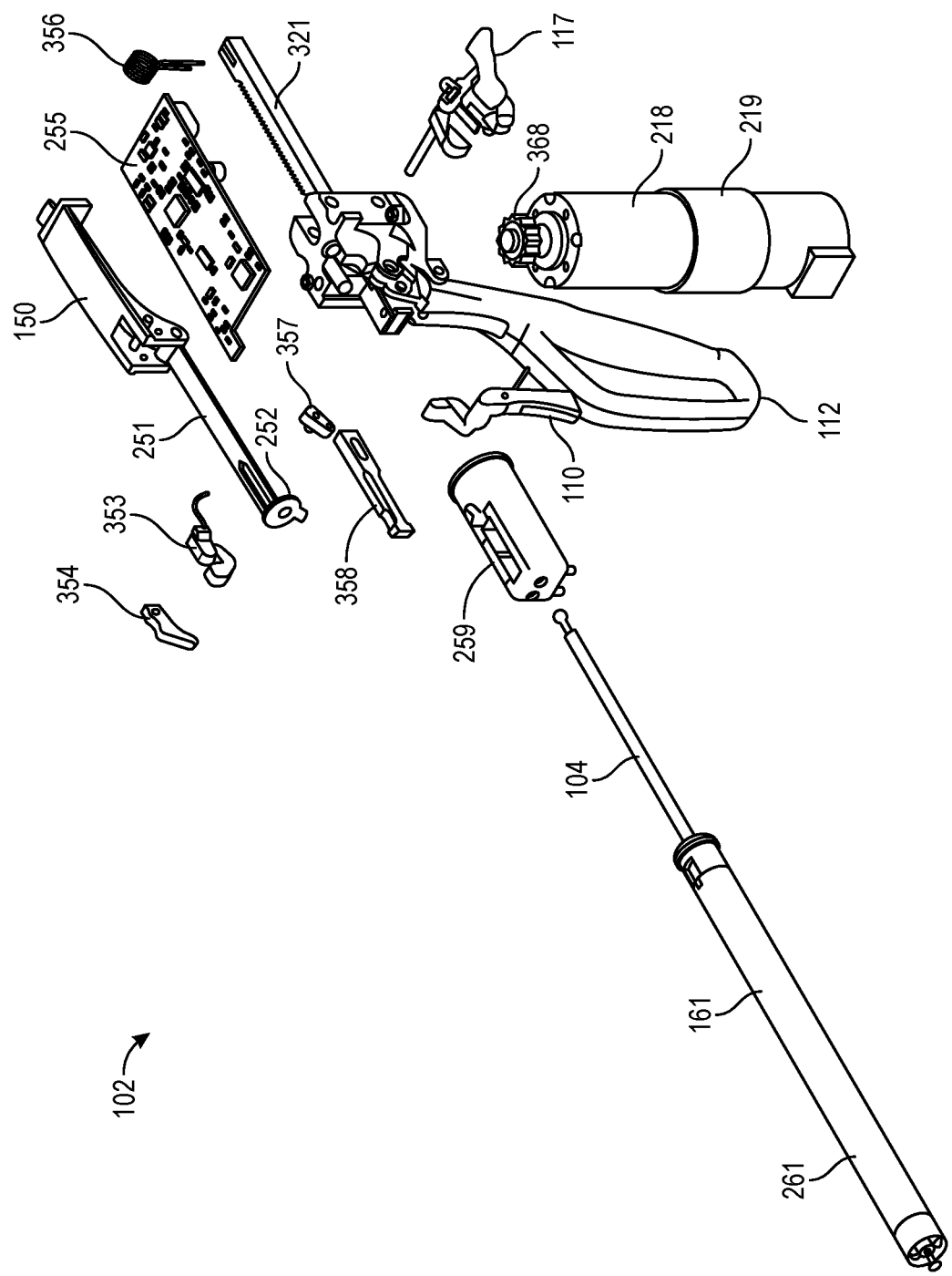
FIG. 3 is another partially schematic, partial exploded view of a portion of the surgical handle assembly of FIG. 2.

FIG. 3 is another partially schematic, partial exploded view of a portion of the surgical handle assembly 102 of FIGS. 1 and 2. In some embodiments, when the selector lever 117 is rotated to the unlocked position, a selector cam can rotate such that a protrusion engages and activates a switch on the circuit board 255. When the switch of the circuit board 255 is activated (e.g., in response to actuation of the power trigger 110), energy can be allowed to flow to the drivetrain 218. In some embodiments, the selector lever 117 can be permitted to rotate to the unlocked position only when the movable handle 112 is moved to its most proximal position and the first elongated member 107 (FIG. 1) and the second elongated member 109 (FIG. 1) of the reloadable cartridge assembly 103 (FIG. 1) are clamped together.

When the selector lever 117 is rotated to the reverse position, the selector cam can rotate a reverse cam and cause a protrusion on the reverse cam to activate another switch on the circuit board 255. In turn, the drivetrain 218 can be controlled to move in reverse such that a gear rack 321 and the drive shaft 104 of the surgical handle assembly 102 are retracted proximally. More specifically, when activated, the drivetrain 218 causes a driving gear 368 to rotate. The driving gear 368 can be configured to cause a driven gear (e.g., not shown in FIG. 3) to rotate and thereby move the gear rack 321 proximally. A proximal end of drive shaft 104 can extend through the articulation lock 259 and be connected to a distal end of the gear rack 321. As shown, a portion of the drive shaft 104 can also be housed within the outer shaft 261 of the elongated body 161.

When the gear rack 321 is fully reversed, a retraction spring 356 can be compressed, and a control system can experience a spike in current as the gear rack 321 is positioned against the retraction spring 356 and/or other components of the motorized surgical handle assembly 102. In some embodiments, the surgical handle assembly 102 can determine that the gear rack 321 is positioned at its proximal-most position based at least in part on the spike in current. After the spike in current, the drivetrain 218 can change direction and rotate the driving gear to unload the retraction spring 356, which can cause the gear rack 321 to move in the distal direction a short distance (e.g., 0.5 mm, 1 mm, 1.2 mm, or 2 mm). As discussed in greater detail below, this process can be used to set or return a blade assembly of the reloadable cartridge assembly 103 (FIG. 1) at a known position, such as a 'zero' or origin position. Additionally, or alternatively, this forward movement can position bosses (e.g., not shown in FIG. 3) of the driving gear 368 between bosses (e.g., not shown in FIG. 3) of the driven gear so that the clamp and unclamp mechanism will work to clamp and unclamp, respectively, the first elongated member 107 (FIG. 1) and the second elongated member 109 (FIG. 1) of the reloadable cartridge assembly 103 (FIG. 1) together.

When the movable handle 112 is moved to the proximal-most position, a frictional force of a friction cam 353 and its associated spring on the movable handle 112 can hold the movable handle 112 in the proximal-most position. A user/physician can open the first elongated member 107 and the second elongated member 109 by moving the movable handle 112 distally manually or by using the reverse function of the selector lever 117.

When the selector lever 117 is rotated to the unlocked position, a surface of the selector cam can rotate against a locking protrusion of the movable handle 112 and lock the movable handle 112 in the proximal position. After the gear rack 321 begins to travel distally, a locking cam can interact with a notch of the movable handle 112 and lock the movable handle 112 in the proximal position.

When a reloadable cartridge assembly, such as the reloadable cartridge assembly 103 of FIG. 1, is attached to the distal end of the surgical handle assembly 102, a bar (not shown) in contact with the distal end of articulation lock 259 can move proximally and cause the articulation lock 259 to move proximally. Proximal movement of the articulation lock 259 can move a bar 358, which can move a cam 357 into contact with (e.g., thereby closing) a switch on the circuit board 255. In turn, the drivetrain 218 can be activated. If no reloadable cartridge assembly is attached to the motorized surgical handle assembly 102, however, the drivetrain 218 will not be activated.

A protrusion on the articulation lock 259 can be configured to interact with an articulation mechanism of the surgical handle assembly 102 such that the articulation knob 122 (e.g., FIGS. 1 and 2) cannot be rotated when a reloadable cartridge assembly is not attached to the surgical handle assembly 102. When (i) a reloadable cartridge assembly is attached to the surgical handle assembly 102, (ii) the movable handle 112 is in the proximal-most position, (iii) the selector lever 117 is switched to an unlocked position, and (iv) a user actuates the power trigger 110 proximally, the power trigger 110 can push an intermediate lever 354 into contact with a switch on the circuit board 255, causing the drivetrain 218 to move the gear rack 321 in a distal direction.

The friction cam 353 is configured to provide friction to the movable handle 112 so that the handle is less likely to move without a user moving it in a proximal or distal direction. The bailout handle 150 includes a 'U'-shaped latch. The 'U'-shaped latch is configured to interact with the first handle half 116-1 (FIG. 2) and the second handle half 116-2 (FIG. 2) to keep the bailout handle 150 secured in the down position. The bottom of the 'U'-shaped latch can interact with a switch on the circuit board 255. When the switch is closed (e.g., pressed), power can be supplied to the circuit board 255. When the bailout handle 150 is lifted and the 'U'-shaped latch is not in contact with the switch (e.g., when the switch is open), no power will flow to the circuit board 255.

Figure 4:
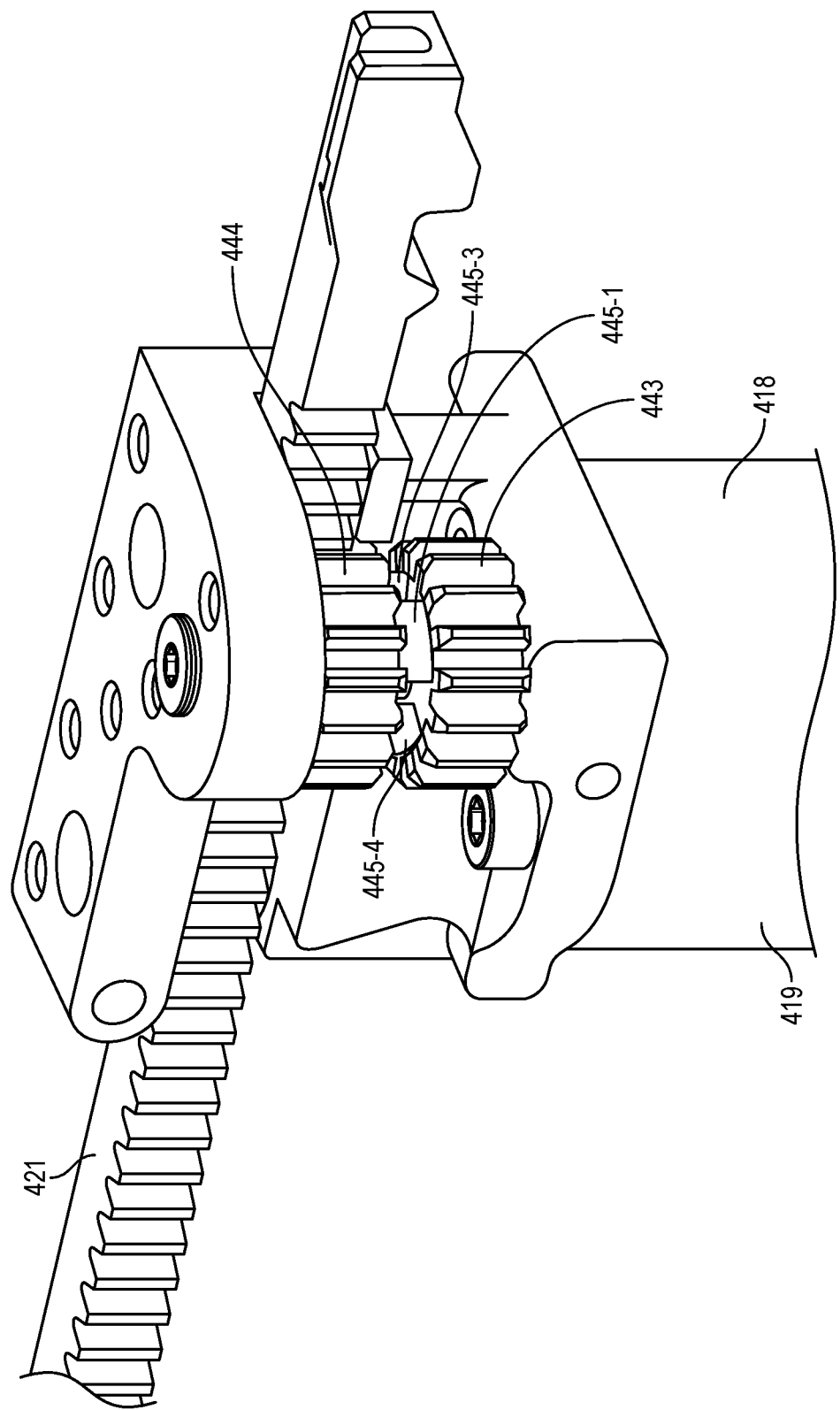
FIG. 4 is a partially schematic diagram of a drivetrain configured in accordance with various embodiments of the present technology.

FIG. 4 is a partially schematic diagram of a portion of a drivetrain 418 configured in accordance with various embodiments of the present technology. It is appreciated that the drivetrain 418 can be an example of the drivetrain 218 of FIGS. 2 and 3, or another drivetrain of the present technology. As shown, the drivetrain 418 is a gear system that includes a driving gear 443 and driven gear 444. An electric motor 419 rotates the driving gear 443 either directly or through one or more other gears (not shown). Using the teeth on its circumferential surface and/or interaction of various bosses (e.g., boss 445-1 on the driving gear 443 with boss 445-3 and/or 445-4 on the driven gear 444), the driving gear 443 rotates the driven gear 444. The driven gear 444 drives a gear rack 421 (e.g., the gear rack 321 of FIG. 3 or another gear rack of the present technology) using teeth on its circumferential surface. In some embodiments, such a driving system can be referred to as a 'rack and pinion' system. More specifically, a rack (e.g., the gear rack 421) can move in response to rotation of a pinion (e.g., the driven gear 444) as the cogs/teeth of the driven gear 444 interact with the cogs/teeth of the gear rack 421. In some embodiments, the driven gear 444 is associated with the gear rack 421 such that rotation of the driven gear 444 causes linear movement of the gear rack 421 in the proximal or distal directions.

Figure 5A:
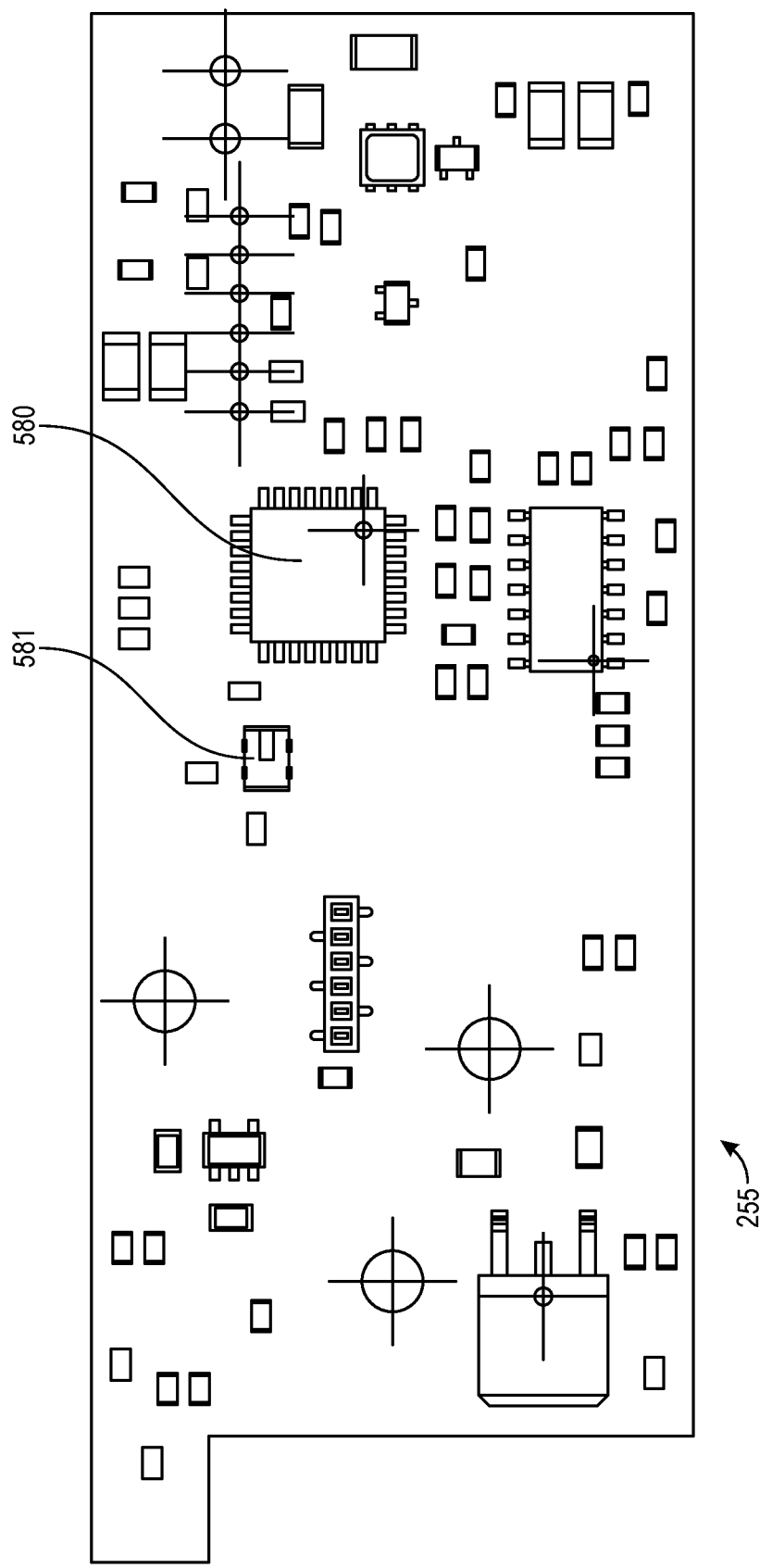
FIGS. 5A and 5B are partially schematic diagrams of a front and a back, respectively, of a circuit board configured in accordance with various embodiments of the present technology.
Figure 5B:
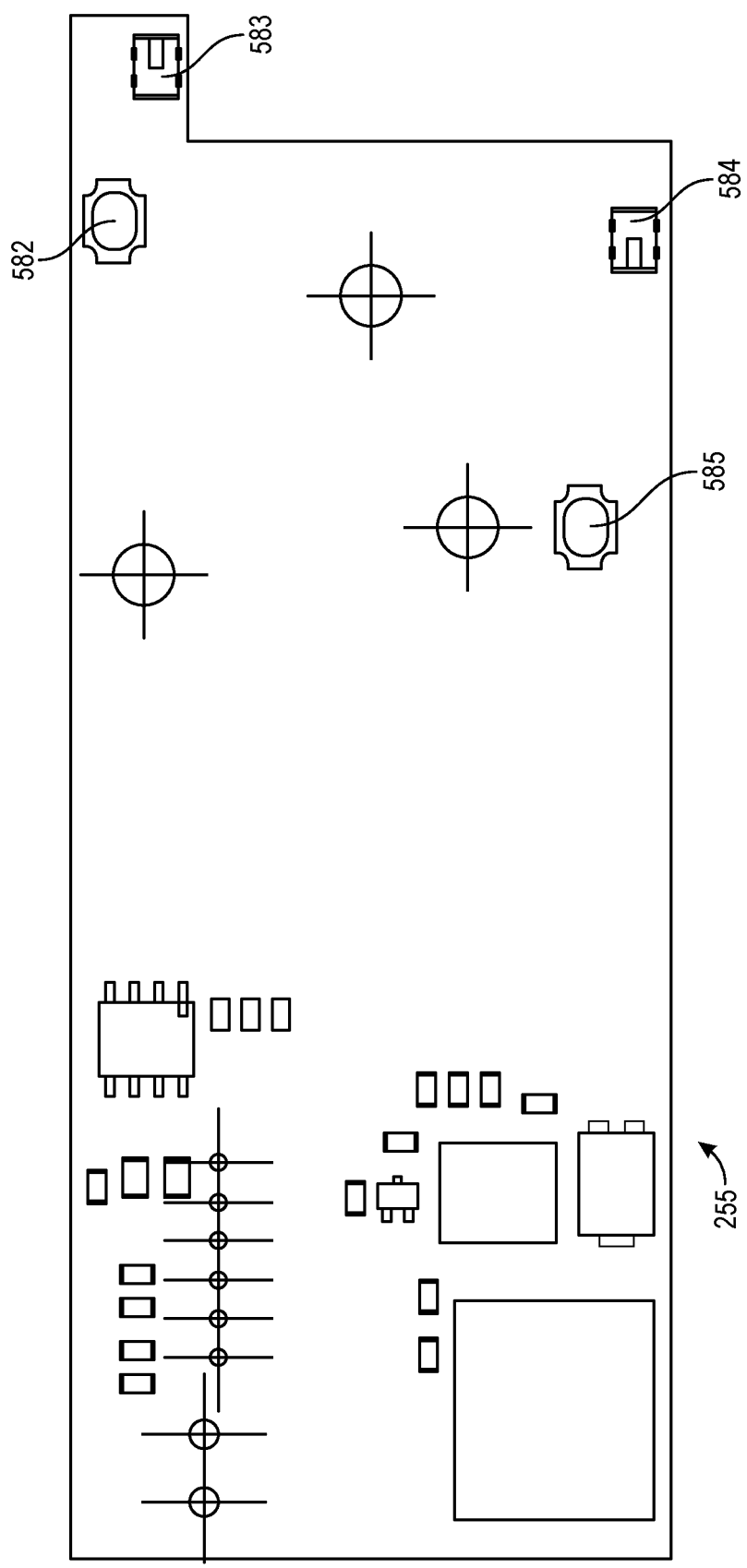

FIGS. 5A and 5B are partially schematic diagrams of a top and a bottom, respectively, of the circuit board 255 of FIGS.

2 and 3. As discussed above, in some embodiments, the surgical handle assembly 102 of FIGS. 1-3 can be controlled via the circuit board 255. Referring to FIG. 5A, the circuit board 255 can include a microcontroller 580 (or microprocessor) for controlling various functions (e.g., one or more of the safety control algorithms disclosed herein) of the surgical handle assembly 102, the electric motor 219 (FIG. 2), a voltage converter, various switches, and/or various other electronics of the system. Additionally, or alternatively, the system 100 (FIG. 1) can include one or more other microcontrollers or microprocessors (e.g., in addition to or in lieu of the microcontroller 580) for controlling the various functions (e.g., one or more of the safety control algorithms disclosed herein) of the surgical handle assembly 102, the electric motor 219 (FIG. 2), the voltage converter, the various switches, and/or the various other electronics of the system. For example, the system 100 can include a microcontroller and/or a microprocessor that resides at a location outside of the surgical handle assembly 102 (FIGS. 1-3), such as in the power source 123 (FIG. 1).

In some embodiments, the microcontroller 580 can run through a series of checks upon start up when the surgical handle assembly 102 is turned on or, in some embodiments, when it is plugged in. For example, the microcontroller 580 can determine whether a reloadable cartridge assembly (e.g., the reloadable cartridge assembly 103 of FIG. 1) is attached to the surgical handle assembly 102 (FIG. 1). If no reloadable cartridge assembly is attached, the microcontroller 580 can instruct the drivetrain 218 (FIGS. 2 and 3) to reverse until the gear rack 321 (FIG. 3) is in the proximal-most position and the retraction spring 356 (FIG. 3) is compressed. In some embodiments, this is called the 'home position.' At this point, upon detecting a current spike, the microcontroller 580 can instruct the drivetrain 218 to rotate the driving gear 443 (FIG. 4) to move the gear rack 321 distally a short distance to unload the retraction spring 356. In some embodiments, the location that is positioned the short distance distal the home position is called the 'loading position.' On the other hand, if upon start up, the microcontroller 580 detects a reloadable cartridge assembly attached to the surgical handle assembly 102, no action is taken in some embodiments.

In some embodiments, when the surgical handle assembly 102 is powered up with no reloadable cartridge assembly attached and the microcontroller 580 instructs the drivetrain 218 to move the gear rack 321 to the loading position, the microcontroller 580 can, upon subsequently detecting that a reloadable cartridge assembly is being attached to the surgical handle assembly 102, instruct the drivetrain 218 to rotate the driving gear 443 a short distance (e.g., approximately 70 degrees) while not moving the driven gear 444 (FIG. 4) or the gear rack 321. This can set the surgical stapler 101 in a clamping or grasping position. More specifically, such movement of the driving gear 443 can cause one or more bosses (e.g., the boss 445-1 of FIG. 4) on the driving gear 443 to be positioned relative to one or more bosses (e.g., the bosses 445-3 and 445-4 of FIG. 4) on the driven gear 444 to allow space for the clamping motion, which moves the gear rack 321 distally without interference from the bosses.

In some embodiments, the system 100 (e.g., the surgical handle assembly 102) includes an encoder for use with the drivetrain 218. The microcontroller 580 can receive information from the encoder to track, for example, a position (e.g., a relative position) of the gear rack 321 and/or a position (e.g., a relative position) of another component attached to the gear rack 321. For example, the microcontroller 580 can receive information from the encoder to track a position of a distal end of a blade assembly and/or another portion of the reloadable cartridge assembly 103 (e.g., along a staple cartridge, the first elongated member 107, and/or the second elongated member 109), such as a distalmost position of an I-beam, a cutting surface of the I-beam, another portion of the I-beam, and/or another component of the reloadable cartridge assembly 103 that is used to expel staples from the staple cartridge. In some embodiments, the microprocessor 580 can zero out the encoder location indicator for the gear rack 321 and/or the other component by moving the gear rack 321 to the home position and/or to the loading position. As discussed in greater detail below, the microcontroller 580 can use the information received from the encoder alone or in combination with other information (e.g., current levels in the drivetrain 218) to, for example, set current limits for distal and/or proximal movement of the gear rack 321, such as using a lookup table (LUT) specifying one or more virtual gears of the electric motor 219. Additionally, or alternatively, the microcontroller 580 can use the encoder information and/or the current information to determine when to switch from a low amp setting to a high amp setting, and/or to determine when the gear rack 321 is properly positioned to allow for actuation of the movable handle 112 to clamp and unclamp the jaws.

As also discussed in greater detail below, the microcontroller 580 can use the encoder information and/or the current information to detect when the I-beam of the reloadable cartridge assembly 103 is at its end of stroke and/or for determining when to stall the electric motor 219 (FIGS. 2 and 3), such as for safety reasons. In some embodiments, the microcontroller 580 may rely on sudden current drops and/or sudden current rises in the drivetrain 218 to detect one or more problems in the system 100. For example, a sudden drop in current in the drivetrain 218 can indicate to the microcontroller 580 that there has been a breakage somewhere in the surgical stapler 101. As another example, a sudden rise in current in the drivetrain 218 can indicate to the microcontroller 280 that the I-beam of the reloadable cartridge assembly 103 has encountered an obstruction (e.g., an engaged lockout mechanism), or is attempting to cut/cause to be stapled tissue that is too thick or tough for the surgical stapler 101.

As still another example, a sudden rise in current in the drivetrain 218 can indicate to the microcontroller 280 that the I-beam of the reloadable cartridge assembly 103 is at its end of stroke. For example, it can be important for the electric motor 219 to quickly (e.g., immediately) stop or stall to cease further distal movement of the gear rack 321 when the I-beam is at the end of its stroke because continued distal movement of the gear rack 321 after the I-beam reaches the end of its stroke can result in damage to the reloadable cartridge assembly 103 and/or inadvertent damage to tissue. Thus, as discussed in greater detail below, the microcontroller 580 can use the encoder information, the current information, and/or other information (e.g., motor speed) to detect obstructions or potential obstructions in the path of the I-beam, such a wall or obstruction at the end of its stroke. Additionally, or alternatively, the microcontroller 580 can use the encoder information, the current information, and/or the other information to (i) distinguish between (a) thick/tough/hard tissue that the surgical stapler 101 can cut and/or staple and (b) an obstruction that the surgical stapler 101 cannot cut and/or staple (e.g., a piece of surgical equipment), and (ii) control the drivetrain 218 appropriately.

Referring again to FIGS. 5A and 5B, the circuit board 255 can include various switches. For example, referring to FIG.

5A, the circuit board 255 can include a switch 581. As discussed above, the 'U'-shaped latch of the bailout handle 150 (FIGS. 1 and 3) can interact with the switch 581. More specifically, when the switch 581 is closed via contact with the 'U'-shaped latch of the bailout handle 150, power can be supplied to the circuit board 255. On the other hand, when the bailout handle 150 is lifted such that the 'U'-shaped latch is not in contact with the switch 581, the switch 581 can be open such that no power flows to the circuit board 255.

Referring now to FIG. 5B, the circuit board 255 can additionally, or alternatively, include switches 582-585. Switch 582 can be a power switch for the drivetrain 218. More specifically, when the power trigger 110 (FIG. 1) is pulled, the power trigger 110 can press a protrusion of an intermediate lever into contact with the switch 582 on the circuit board 255, permitting power to flow to the drivetrain 218 and/or the drivetrain 218 to move the gear rack 321 (FIG. 3) distally. In some embodiments, the power switch 582 can be an open/close switch such that the drivetrain 218 receives relatively constant power when the power trigger 110 is pulled. In other embodiments, the power switch 582 can be a variable switch (e.g., a variable resistor, varistor, potentiometer, or another analog sensor) such the drivetrain 218 receives more power (and therefore runs faster) as the power trigger 110 is squeezed harder or actuated by a greater amount.

Switch 583 of the circuit board 255 can be a reload switch. As discussed above, when a reloadable cartridge assembly (e.g., the reloadable cartridge assembly 103 of FIG. 1) is attached to the surgical handle assembly 102 (FIG. 1), a cam can be pressed into the switch 583 to indicate the attachment. Thus, when no reloadable cartridge assembly is attached to the surgical handle assembly 102, the switch 583 can be open such that the surgical handle assembly 102 is prevented from being electrically activated.

Switch 584 of the circuit board 255 can be a ready-to-fire switch. For example, when the selector lever 117 (FIG. 1) is rotated to the unlocked position, a selector cam can rotate such that a protrusion engages the switch 584 on the circuit board 255. When the switch 584 of the circuit board 255 is activated, the surgical handle assembly 102 can be placed in a ready-to-fire state in which energy can be allowed to flow to the drivetrain 218 (e.g., in response to actuation of the power trigger 110 and/or to move the gear rack 321 distally).

Switch 585 of the circuit board 255 can be a reverse switch. For example, when the selector lever 117 (FIG. 1) is rotated to the reverse position, a cam can rotate a reverse cam and cause a protrusion on the reverse cam to engage the switch 585 on the circuit board 255. In turn, the drivetrain 218 (FIG. 2) can be controlled to move in reverse such that the gear rack 321 (FIG. 3) and the drive shaft 104 (FIGS. 1 and 3) of the surgical handle assembly 102 are retracted proximally.

As discussed above, power can be supplied to the circuit board 255, such as from a battery or another power source (e.g., the power source 123 of FIG. 1). In some embodiments, the drivetrain 218 (FIG. 2) can be provided with 12V for driving the gear rack 321 distally and/or 24V for retracting the gear rack 321 proximally.

Additional details regarding surgical handle assemblies and, in particular, motorized surgical handle assemblies, are provided in U.S. patent application Ser. No. 17/833,302, the disclosure of which is incorporated by reference herein in its entirety.

Figure 6:
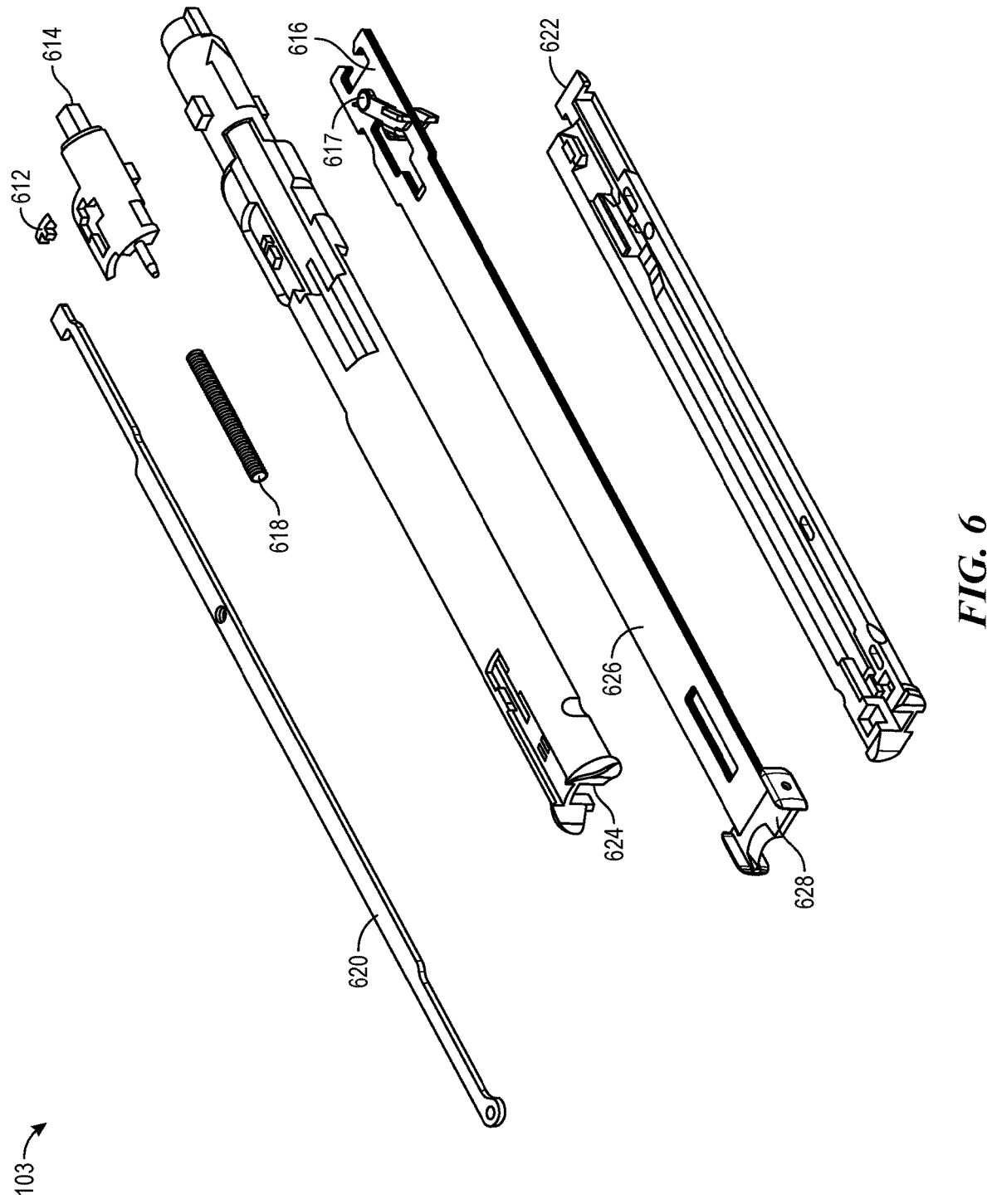
FIG. 6 is a partially schematic exploded view of a portion of a surgical reloadable cartridge assembly configured in accordance with various embodiments of the present technology.

FIG. 6 is a partially schematic exploded view of a portion of the surgical reloadable cartridge assembly 103 of FIG. 1. As shown, the surgical reloadable cartridge assembly 103 can include a blade lock 612, a lock slider 614, a spring 618, an articulation arm 620, a first cover portion 324, a second cover portion 622, and a blade assembly 616. The blade assembly 616 can include a number of leaves 626, an I-beam 628, and a lockout assembly 617 (e.g., a single-use lockout assembly).

The lock slider 614 is configured to engage the blade lock 612 and actuate the blade lock 612 radially from a first position to a second position. The spring 618 can be configured to bias the lock slider 614 in a proximal direction such that the lock slider 614 is engaged with the blade lock 612 and the blade lock 612 is in the first position. The first position, for example, can be a secure position that locks the blade assembly 616. The blade assembly 616 can be locked when the blade lock 612 is between the blade assembly 616 and the lock slider 614. The lock slider 614 can be configured to move proximally to engage the blade lock 612 and actuate the blade lock 612 from the second position to the first position. The blade lock 612 can actuate radially to the second position in response to the lock slider 614 moving in a distal direction when the reloadable cartridge assembly 103 is coupled to a surgical handle assembly (e.g., the surgical handle assembly 102 of FIG. 1). For example, the blade assembly 616 can be unlocked when the lock slider 614 is between the blade assembly 616 and the blade lock 612.

Figure 7:
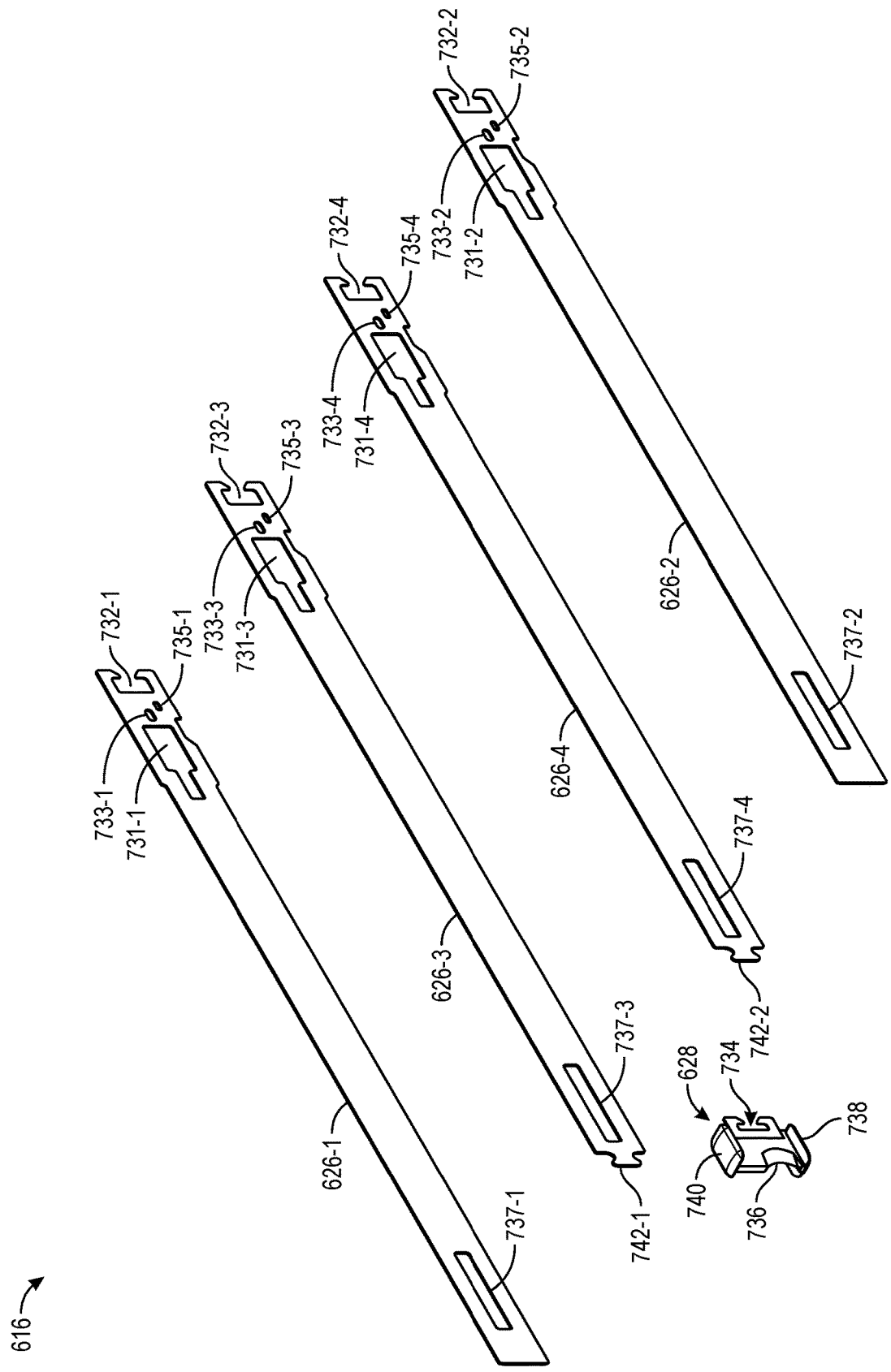
FIG. 7 is a partially schematic exploded view of a blade assembly configured in accordance with various embodiments of the present technology.

FIG. 7 is a partially schematic exploded view of the blade assembly 616 of FIG. 6. As shown, the blade assembly 616 includes a number of outer leaves 626-1 and 626-2, a number of inner leaves 626-3 and 626-4, and the I-beam 628. Each of the leaves 626-1, 626-2, 626-3, and 626-4 can include a number of openings (e.g., to accommodate the lockout assembly 617). For example, the leaves 626-1, 626-2, 626-3, and 626-4 can include a first opening 731-1, 731-2, 731-3, and 731-4, respectively; a second opening 733-1, 733-2, 733-3, and 733-4, respectively; and a third opening 735-1, 735-2, 735-3, and 735-4, respectively. As discussed in greater detail below, the lockout assembly 617 can be used to prevent the reloadable cartridge assembly 103 from being fired more than one time.

Each of the leaves 626-1, 626-2, 626-3, and 626-4 can also include a fourth opening 737-1, 737-2, 737-3, and 737-4, respectively, (e.g., to increase or enhance flexibility of the leaves 626-1, 626-2, 626-3, and 626-4); and/or a slot 732-1, 732-2, 732-3, and 732-4, respectively. The slots 732-1, 732-2, 732-3, and 732-4 can be used to connect the blade assembly 616 to the drive shaft 104 (FIGS. 1-3) of the surgical handle assembly 102 (FIG. 1). The drive shaft 104 can move distally or proximally in response to movement of the movable handle 112 (FIG. 1). The distal end of the inner leaves 626-3 and 626-4 can each include a capture feature 742-1 and 742-2, respectively. The I-beam 628 can include a cutting surface 736, a top portion 740, a bottom portion 738, and a mechanical slot 734. When the blade assembly 616 is assembled, the capture feature 742-1 and the capture feature 742-2 can be positioned within the mechanical slot 734 to form a mechanical interlock.

The top portion 740 and/or the bottom portion 738 of the I-beam 628 can interact with the first elongated member 107 (FIG. 1) and/or the second elongated member 109 (FIG. 1). More specifically, when the blade assembly 616 is moved distally by the drive shaft 104 (FIGS. 1-3), the top portion 740 and/or the bottom portion 738 of the I-beam 628 can cause the first elongated member 107 and the second elongated member 109 to move toward one another and/or to clamp (e.g., tissue). Further distal movement of blade assembly 616 when the first elongated member 107 and the second elongated member 109 are clamped can cause staples to be ejected from a staple cartridge (e.g., of the first elongated member 107) and toward an anvil (e.g., of the second elongated member 109) such that the staples are bent into a tissue holding configuration. Proximal movement of blade assembly 616 by the drive shaft can cause the first elongated member 107 and the second elongated member 109 to move away from one another and/or to unclamp.

The capture feature 742-1 and/or the capture feature 742-2 can be 'T'-shaped, and the mechanical slot 734 can have a complimentary 'T' shape. The capture feature 742-1, the capture feature 742-2, and/or the mechanical slot 734 can have different shapes (e.g., besides 'T' shapes) in other embodiments of the present technology. For example, other shapes such as dove tails, stars, ovals, and circles can be used. The capture features 742-1 and 742-2 and the mechanical slot 734 may be of complimentary shapes such that the capture features 742-1 and 742-2 fit within the mechanical slot 734 to form an interlock. The shape can be such that when tension is placed on the proximal end of an inner leaf 626-3 and the inner leaf 626-4, the inner leaf 626-3 and the inner leaf 626-4 will tension the I-beam 628 and will not be pulled out of the mechanical slot 734. The proximal end of the shape of the mechanical slot 734 can be open to allow the capture feature 742-1 and 742-2 to be positioned within the shaped opening of the mechanical slot 734.

The two outer leaves 626-1 and 626-2 can be positioned along and outside of the inner leaves 626-3 and 626-4, and can be welded or secured to the I-beam 628. In other words, only the inner leaves 626-3 and 626-4 are secured directly to the I-beam 628 in some embodiments (e.g., to provide greater flexibility). In other embodiments, all or a subset of the leaves 626-1 626-2, 626-3, and/or 626-4 can be attached directly to the I-beam 628.

Figure 8A:
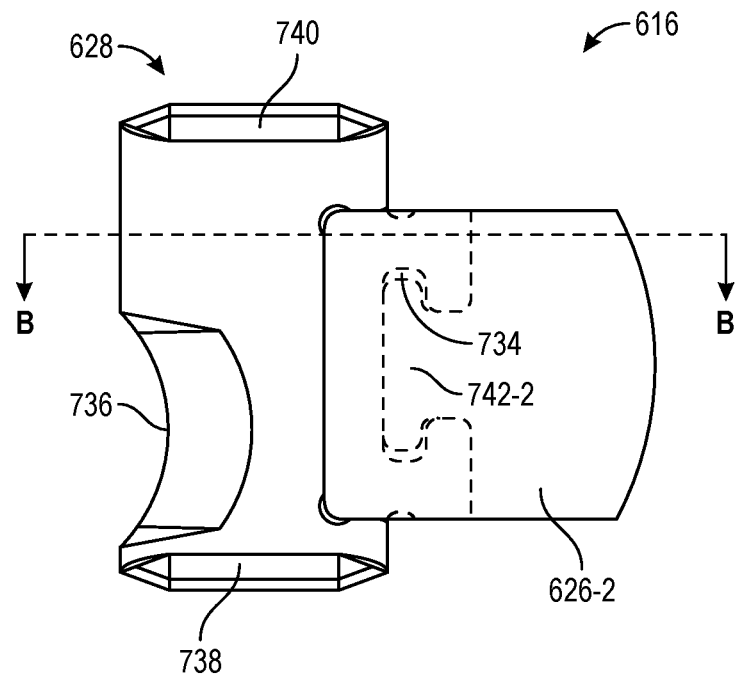
FIG. 8A is a partially schematic diagram of a distal end of the blade assembly of FIG. 6.
Figure 8B:
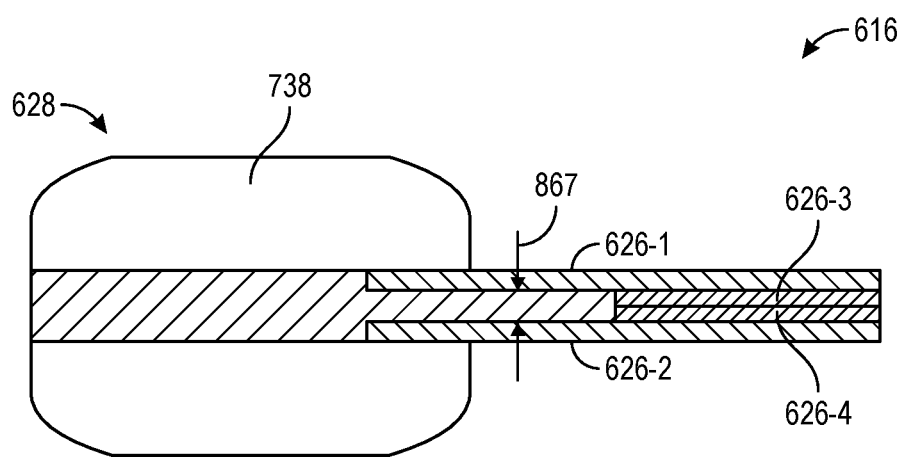
FIG. 8B is a partially schematic, cross-sectional view of the distal end of the blade assembly of FIG. 6.

FIG. 8A is a partially schematic diagram of a distal end of the blade assembly 616 of FIGS. 6 and 7, and FIG. 8B is a partially schematic, cross-sectional view of the distal end of the blade assembly 616 taken along the line B-B shown in FIG. 8A. Referring first to FIG. 8A, the distal end of the blade assembly 616 includes (i) the I-beam 628 having the cutting surface 736, the top portion 740, and the bottom portion 738, and (ii) the leaf 626-2. Shown by the hidden (e.g., dashed or broken) lines in FIG. 8A is the mechanical slot 734 and the capture feature 742-2 of the inner leaf 626-4.

Referring now to FIG. 8B, the central body of the I-beam 628 and the distal ends of the leaves 626-1, 626-2, 626-3, and 626-4 are shown. When the blade assembly 616 is in an assembled state, the capture feature 742-2 of the inner leaf 626-4 is fitted in the mechanical slot 734. A thickness 867 of the mechanical slot 734 is approximately equal to or slightly larger than a total thickness of the number of inner leaves 626-3 and 626-4.

As discussed in greater detail below, the distal end of each of the outer leaves 626-1 and 626-2 can fit within a corresponding notch (not shown in FIGS. 8A and 8B) and/or can be welded or secured to the I-beam 628. In some embodiments, the distal end of each of the outer leaves 626-1 and 626-2 can be laser welded to the I-beam 628 in its corresponding notch. In some embodiments, each of the outer leaves 626-1 and 626-2 can additionally, or alternatively, be spot or laser welded to the body surrounding the mechanical slot 734. The depth of the notches can be selected so that outer edges of the outer leaves 626-1 and 626-2 are approximately equal to a thickness of a middle portion (e.g., not shown in FIGS. 8A and 8B) of the I-beam 628 when the blade assembly 616 is in an assembled state.

Figure 9A:
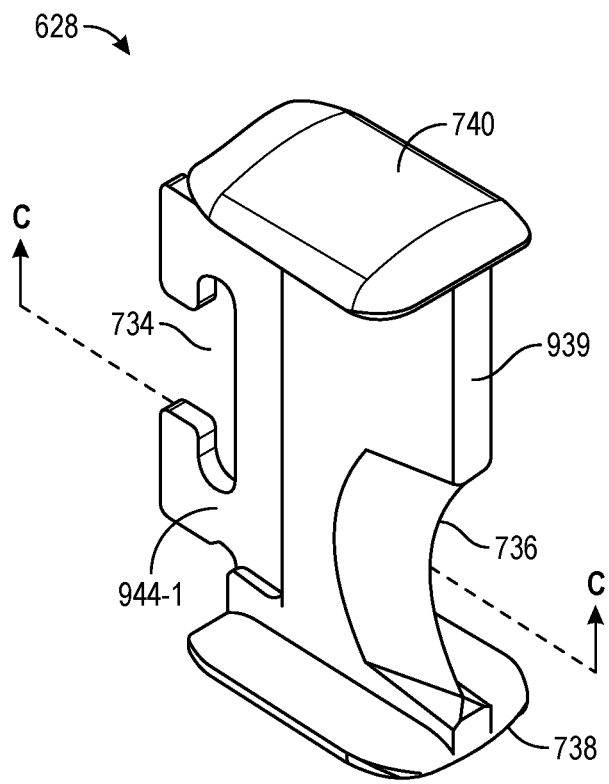
FIG. 9A is a partially schematic perspective view of an I-beam of the blade assembly of FIG. 6.
Figure 9B:
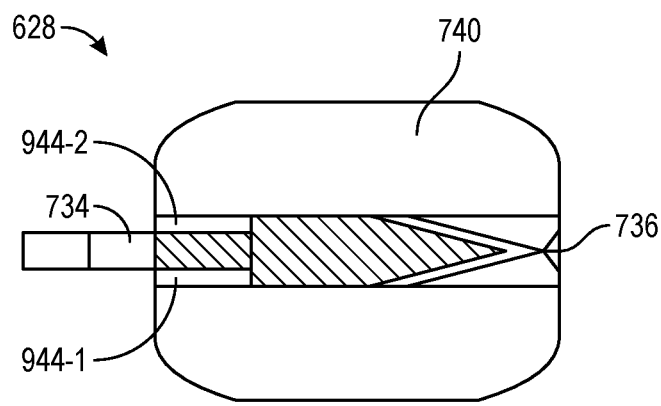
FIG. 9B is a partially schematic cross-sectional view of the I-beam of the blade assembly of FIG. 9A.

FIG. 9A is a partially schematic perspective view of the I-beam 628 of the blade assembly 616 of FIG. 6, and FIG. 9B is a partially schematic cross-sectional view of the I-beam 628 of the blade assembly 616 taken along line C-C shown in FIG. 9A. Referring first to FIG. 9A, the I-beam 628, including the top portion 740, the bottom portion 738, the cutting surface 736, the mechanical slot 734, and a middle portion 939 having a notch 944-1, is shown. Referring now to FIG. 9B, the I-beam 628 can additionally include a notch 944-2. In some embodiments, an outer leaf (e.g., the outer leaf 626-1 of FIG. 6) can be welded or secured within the notch 944-1, and another outer leaf (e.g., the outer leaf 626-2 of FIG. 6) can be welded or secured within the notch 944-2. The assembled blade assembly 616 can then be used in a surgical reloadable cartridge assembly, such as the surgical reloadable cartridge assembly 103 of FIG. 1.

Figure 10:
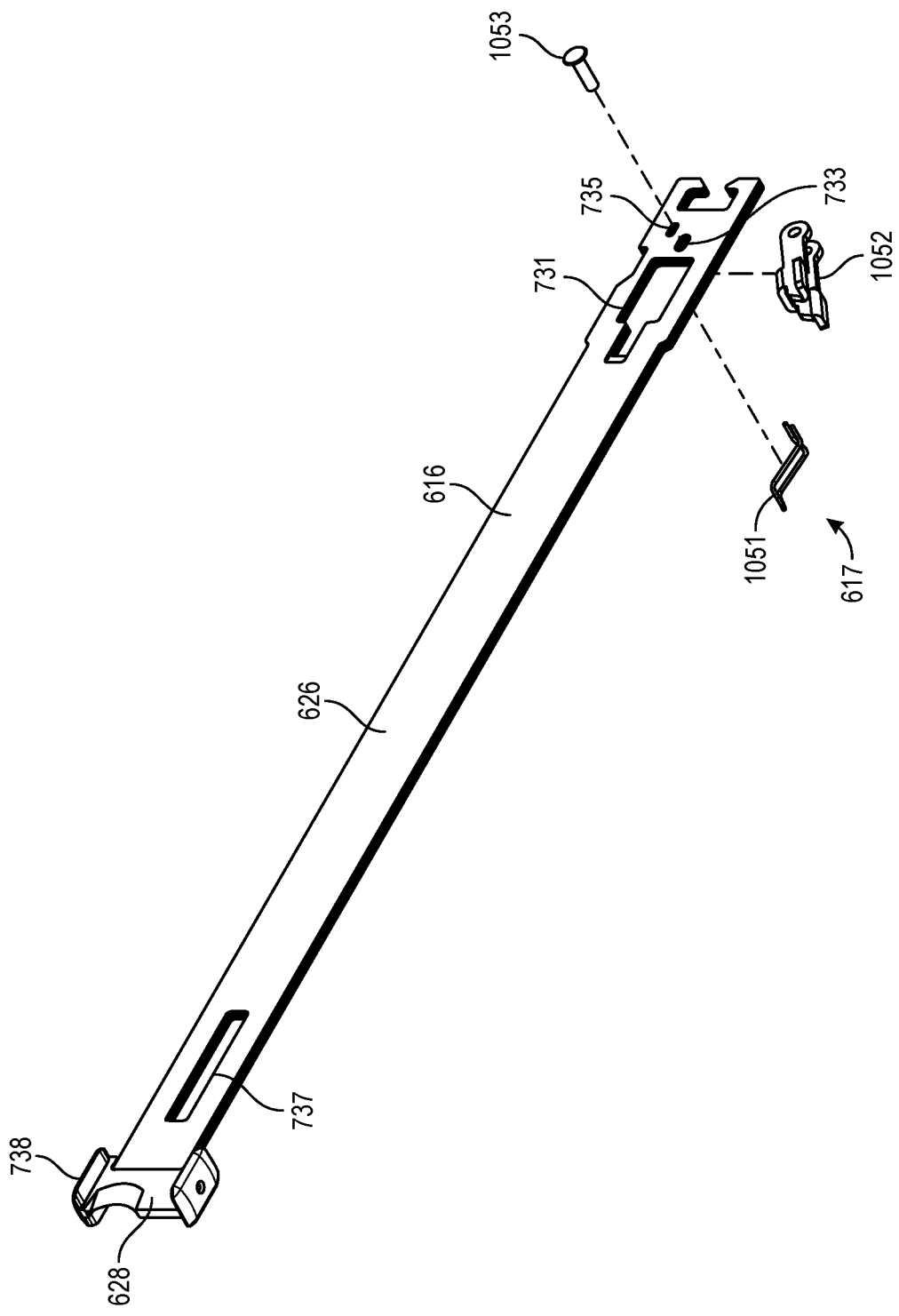
FIG. 10 is a partially schematic, partial exploded view of a lockout assembly configured in accordance with various embodiments of the present technology.

FIG. 10 is a partially schematic exploded view of the lockout assembly 617 about the blade assembly 616 of FIG. 6. As shown, the lockout assembly 617 includes a mechanical latch 1052 (or lever), a pin 1053, and a spring 1051 (e.g., a wire spring). When the lockout assembly 617 is installed on the blade assembly 616 and is in an assembled state, the mechanical latch 1052 is at least partially positioned within the first openings 731 in the leaves 626 and is pivotably held in place at one end using the pin 1053 that extends through the second openings 733 in the leaves 626. Furthermore, the spring 1051 is installed in the third openings 735 of the leaves 626 in such a manner that it engages with the mechanical latch 1052 and biases an unpinned end of the mechanical latch 1052 in a direction (e.g., a direction that extends toward a top of the leaves 626, such as toward a side of the leaves 626 opposite the bottom portion 738 of the I-beam 628).

Figure 11A:
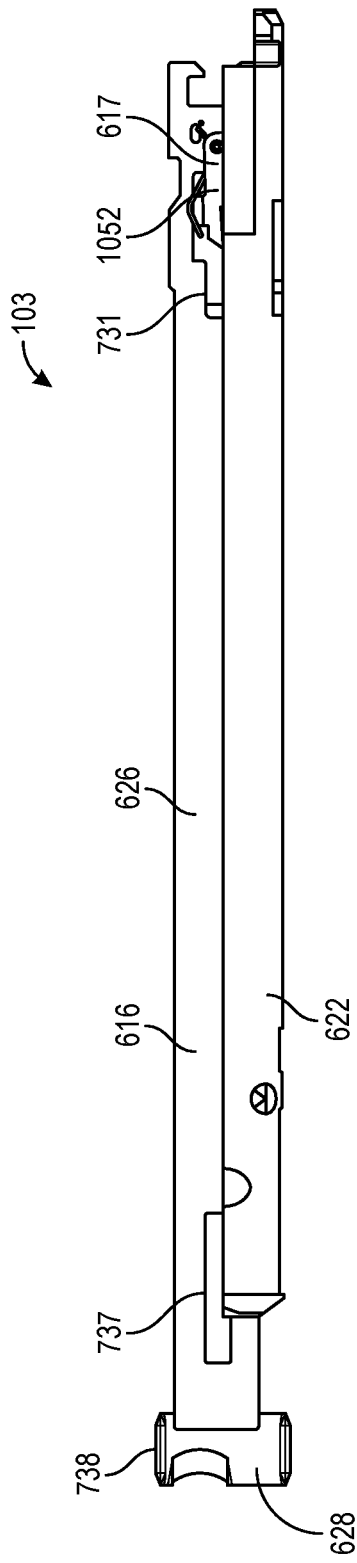
FIG. 11A is a partially schematic side view of a portion of the surgical reloadable cartridge assembly of FIG. 6 illustrating the lockout assembly of FIG. 10 in a first state in accordance with various embodiments of the present technology.
Figure 11B:
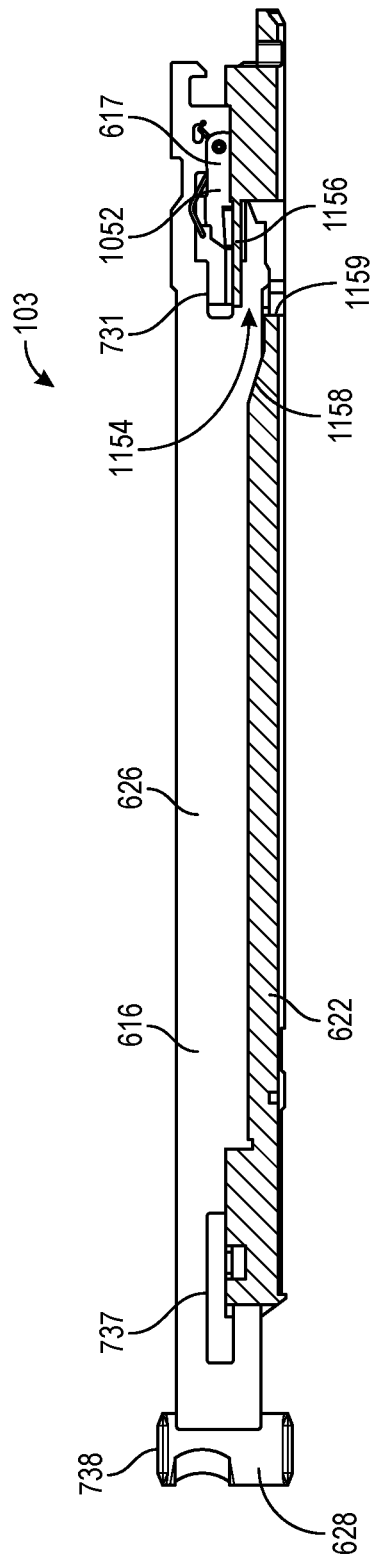
FIG. 11B is a partially schematic, cross-sectional side view of the portion of the surgical reloadable cartridge assembly of FIG. 6 while the lockout assembly is in the first state as shown in FIG. 11A.

FIGS. 11A and 11B are a partially schematic side view and a partially schematic cross-sectional side view, respectively, of the second cover portion 622 of FIG. 6 engaged with the blade assembly 616 of FIG. 6 while the lockout assembly 617 is in a first state (e.g., an unlocked state). As best shown in FIG. 11B, the second cover portion 622 includes a ledge 1156 (e.g., a shelf, platform, lip, block). Beneath the ledge 1156 in FIGS. 11A and 11B (e.g., on a side of the ledge 1156 opposite the mechanical latch 1052 of the lockout assembly 617) is a cavity 1154 that, as discussed in greater detail below, is configured to receive the mechanical latch 1052 after the blade assembly 616 is advanced distally relative to the second cover portion 622 beyond a threshold amount and then subsequently retracted proximally. The second cover portion 622 also includes a sloped or tapered surface 1158 that slopes toward the cavity 1154. The second cover portion 622 can further include a lip 1159 (e.g., an edge, step, surface, block) at an end of the tapered surface 1158 (e.g., serving as a sidewall of the cavity 1154). As discussed in greater detail below, the lip 1159 can prevent distal movement of the blade assembly 616 relative to the second cover portion 622 after the mechanical latch 1052 has been fully captured within the cavity 1154.

In the first state illustrated in FIGS. 11A and 11B, the mechanical latch 1052 is contacting (e.g., abutting, resting upon) the ledge 1156. More specifically, although the spring 1051 (FIG. 10) of the lockout assembly 617 is biasing the mechanical latch 1052 toward the cavity 1154, the ledge 1156 prevents the mechanical latch 1052 from pivoting about the pin 1053 (FIG. 10) and toward the tapered surface 1158 and the cavity 1154. In this first state, the reloadable cartridge assembly 103 is therefore permitted to clamp and/or unclamp the first elongated member 107 (FIG. 1) and the second elongated member 109 (FIG. 1) without locking out the reloadable cartridge assembly 103. As used herein, the terms 'locking out' or 'locked out' or 'lockout' refer to a state of the system 100 in which the blade assembly 616 of the reloadable cartridge assembly 103 is prevented from being advanced distally to or beyond a given point, such as a point at which the surgical stapler 101 is initially expected to begin cutting, stapling, or otherwise acting upon tissue clamped between the first elongated member 107 and the second elongated member 109.

Figure 12A:
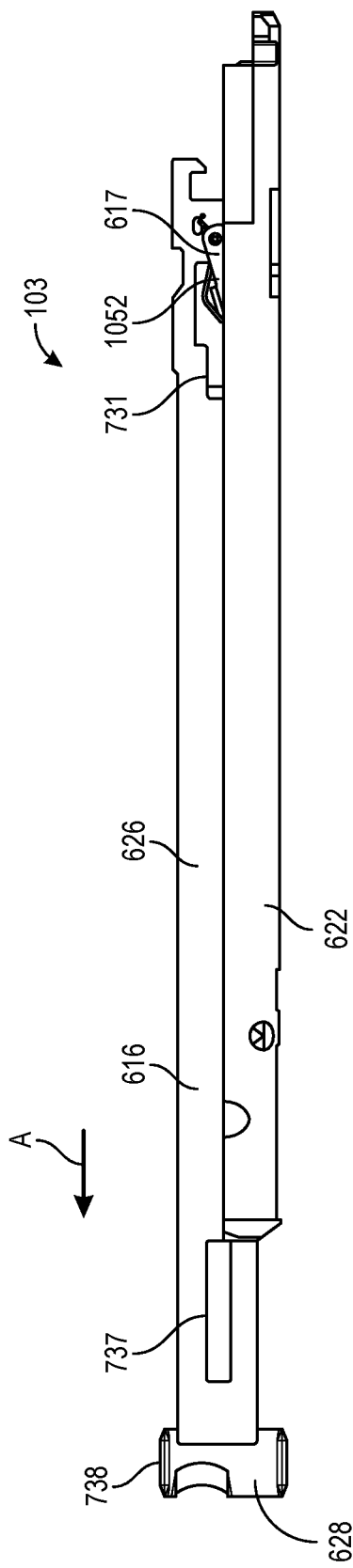
FIG. 12A is a partially schematic side view of a portion of the surgical reloadable cartridge assembly of FIG. 6 illustrating the lockout assembly of FIG. 10 in a second state in accordance with various embodiments of the present technology.
Figure 12B:
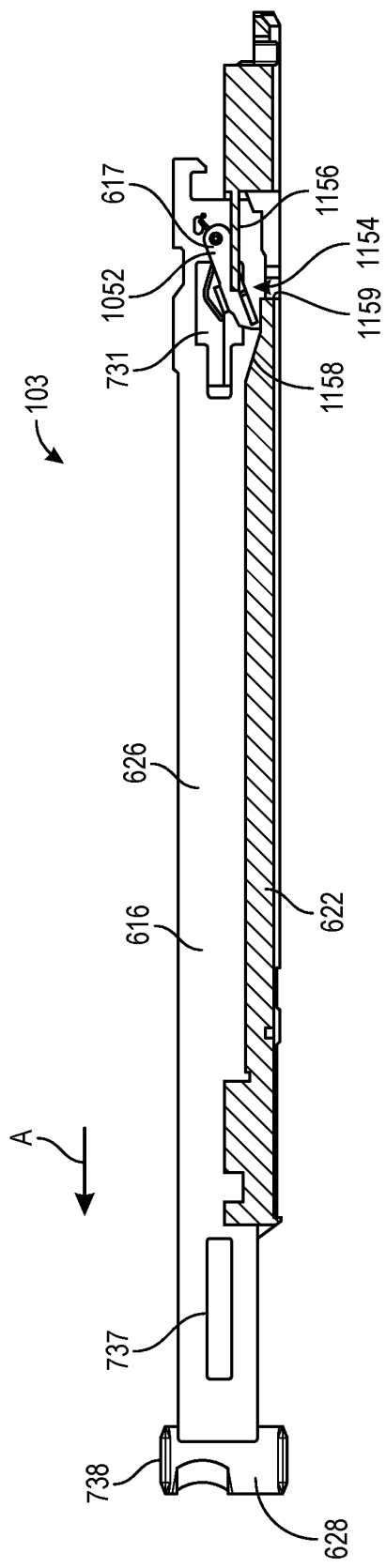
FIG. 12B is a partially schematic, cross-sectional side view of the portion of the surgical reloadable cartridge assembly of FIG. 6 while the lockout assembly is in the second state as shown in FIG. 12A.

FIGS. 12A and 12B are a partially schematic side view and a partially schematic cross-sectional side view, respectively, of the second cover portion 622 of FIG. 6 engaged with the blade assembly 616 of FIG. 6 while the lockout assembly 617 is in a second state (e.g., a transition state). In comparison with FIGS. 11A and 11B, FIGS. 12A and 12B illustrate the blade assembly 616 positioned more distal relative to the second cover portion 622. In other words, the blade assembly 616 has been advanced distally relative to the second cover portion 622 generally along or parallel to arrow A. More specifically, as best shown in FIG. 12B, the blade assembly 616 has been advanced distally by an extent that allowed the mechanical latch 1052 to clear the ledge 1156. At the point where the mechanical latch 1052 clears the ledge 1156, the ledge 1156 no longer prevents rotation of the mechanical latch 1052, and the biasing provided by the spring 1051 (FIG. 10) can pivot the mechanical latch 1052 toward the tapered surface 1158 and the cavity 1154, thereby moving the lockout assembly 617 to the second state.

As shown in FIG. 12B, as the mechanical latch 1052 pivots toward the tapered surface 1158 and the cavity 1154, the mechanical latch 1052 can contact the tapered surface 1158, which can prevent the spring 1051 from rotating the mechanical latch 1052 fully into the cavity 1154. Thus, while the lockout assembly 617 is in the second state shown in FIGS. 12A and 12B, the blade assembly 616 can be permitted to continue to move distally in a direction generally along or parallel to the arrow A (e.g., such that the mechanical latch 1052 moves up the tapered surface 1158 in a direction generally away from the cavity 1154). The blade assembly 616 can also be permitted to move proximally in a direction generally opposite to the arrow A (e.g., such that the mechanical latch 1052 moves down the tapered surface 1158 in a direction generally toward the cavity 1154). As discussed in greater detail below, once the mechanical latch 1052 clears the ledge 1156, the lockout assembly 617 can be transitioned to a third state (e.g., a locked or lockout state) by moving the blade assembly 616 proximally relative to the second cover portion 622 such that the mechanical latch 1052 falls off the end of the tapered surface 1158 and into the cavity 1154.

In some embodiments, the reloadable cartridge assembly 103 can be designed such that the location at which the mechanical latch 1052 clears the ledge 1156 corresponds to one or more other functions or features of the reloadable cartridge assembly 103. For example, the location can correspond to a point at or before which the blade assembly 616 or another component of the reloadable cartridge assembly 103 is expected to initially engage with (e.g., contact, cut, staple) tissue clamped between the first elongated member 107 (FIG. 1) and the second elongated member 109 (FIG. 1). As a specific example, the location can correspond to a point at which the blade assembly 616 (e.g., the I-beam 628) extends distally beyond the stabilizing bracket 108 (FIG. 1). In these and other embodiments, the location can correspond to a point at or before which the blade assembly 616 is used to initially expel staples (e.g., from the first elongated member 107).

Figure 13A:
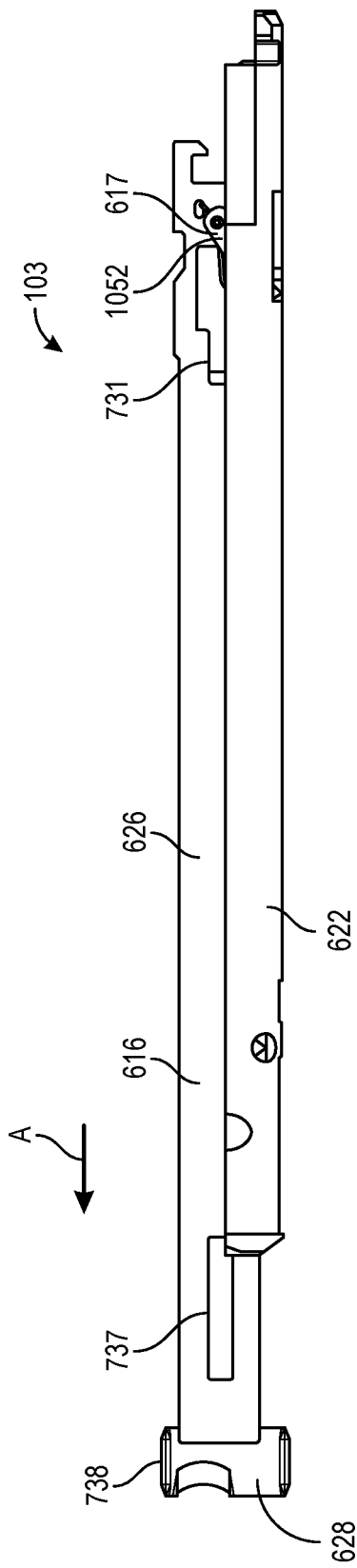
FIG. 13A is a partially schematic side view of a portion of the surgical reloadable cartridge assembly of FIG. 6 illustrating the lockout assembly of FIG. 10 in a third state in accordance with various embodiments of the present technology.
Figure 13B:
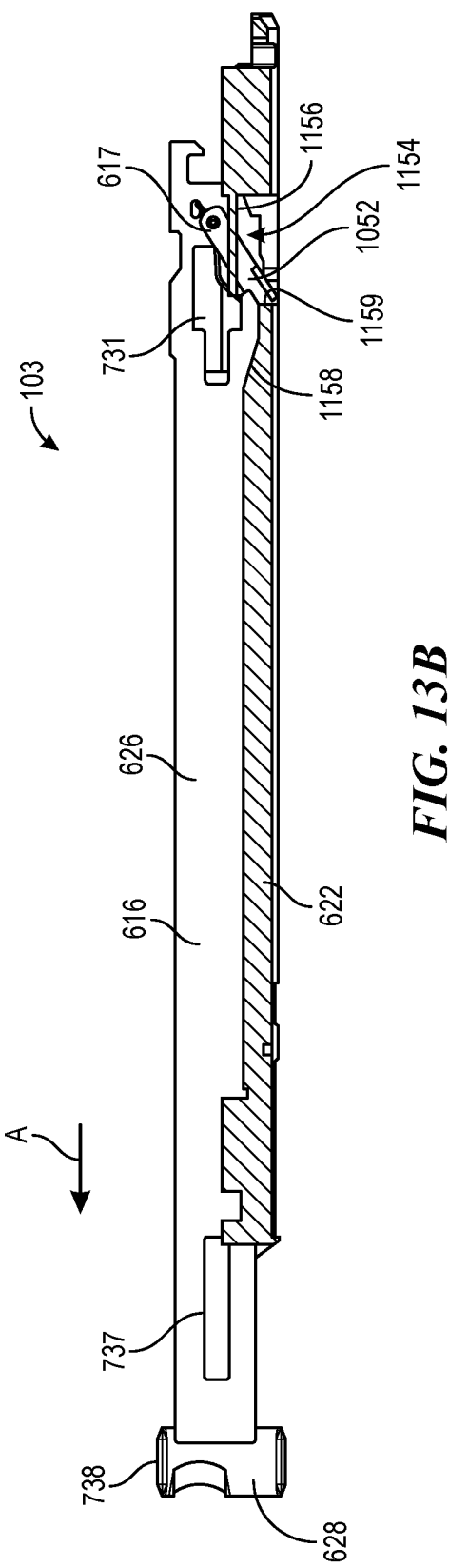
FIG. 13B is a partially schematic, cross-sectional side view of the portion of the surgical reloadable cartridge assembly of FIG. 6 while the lockout assembly is in the third state as shown in FIG. 13A.

FIGS. 13A and 13B are a partially schematic side view and a partially schematic cross-sectional side view, respectively, of the second cover portion 622 of FIG. 6 engaged with the blade assembly 616 of FIG. 6 while the lockout assembly 617 is in a third state (e.g., a locked or lockout state). In comparison with FIGS. 12A and 12B, FIGS. 13A and 13B illustrate the blade assembly 616 positioned more proximal relative to the second cover portion 622 such that the mechanical latch 1052 is fully captured within the cavity 1154. In other words, as best shown in FIG. 13B, after the blade assembly 616 was placed in the second state shown in FIGS. 12A and 12B, the blade assembly 616 was retracted proximally such that the mechanical latch 1052 (i) moved down the tapered surface 1158 and (ii) fell off the end of the tapered surface 1158 and into the cavity 1154. Once the mechanical latch 1052 is positioned within the cavity 1154 as shown in FIG. 13B, attempting to move the blade assembly 616 distally along or generally parallel to the arrow A can bring the mechanical latch 1052 into contact with the lip 1159. Thus, the lip 1159 can prevent distal movement of the blade assembly 616, at least when the mechanical latch 1052 is in contact with the lip 1159. Therefore, when the lockout assembly 617 is in the third state, the first elongated member 107 (FIG. 1) and the second elongated member 109 (FIG. 1) of the reloadable cartridge assembly 103 (FIG. 1) can still be used to clamp and unclamp tissue, but distal movement of the blade assembly 616 beyond the point at which the mechanical latch 1052 contacts the lip 1159 is not permitted. Stated another way, when the lockout assembly 617 is in the third state, the system 100 (e.g., the reloadable cartridge assembly 103 and/or the surgical handle assembly 102) can be locked out. As discussed in greater detail below, while the lockout assembly 617 is in the third state, attempts to move the blade assembly 616 distally beyond the point at which the mechanical latch 1052 contacts the lip 1159 can cause the electric motor 219 (FIG. 2) of the surgical handle assembly 102 (FIG. 1) to stall.

In some embodiments, the reloadable cartridge assembly 103 can be designed such that the location at which the mechanical latch 1052 falls off the end of the tapered surface 1158 and into the cavity 1154 to transition the lockout assembly 617 to the third state corresponds to one or more other functions or features of the reloadable cartridge assembly 103. For example, the location can correspond to a point that is positioned proximal to the location at which the mechanical latch 1052 clears the ledge 1156 to transition the lockout assembly 617 to the second state. In other words, the location at which the mechanical latch 1052 falls off the end of the tapered surface 1158 and into the cavity 1154 can be positioned such that the lockout assembly 617 is moved to the third state when it is likely that the blade assembly 616 has already been used to cut tissue and/or expel staples (e.g., from the first elongated member 107). Thus, the third state of the lockout assembly 617 is expected to prevent firing of the blade assembly 616 in situations in which (i) tissue clamped between the first elongated member 107 and the second elongated member 109 is cut without being stapled (e.g., because staples have already or previously been expelled from at least a portion of the first elongated member 107) and/or (ii) at least part of the tissue clamped between the first elongated member 107 and the second elongated member 109 may have already been cut and/or stapled such that at least the part of the tissue may not currently be adequately or securely held in place by the clamping force of the first elongated member 107 and the second elongated member 109.

Additional details regarding blade assemblies and, in particular, blade assemblies for surgical reloadable cartridge assemblies, are provided in U.S. patent application Ser. No. 17/669,683, the disclosure of which is incorporated by reference herein in its entirety.

A brief summary of basic operation of the system 100 (FIG. 1) is provided here for the sake of clarity and understanding. The reloadable cartridge assembly 103 can be releasably attached to the surgical handle assembly 102, and the selector lever 117 can be positioned in the locked position. Thereafter, a user can actuate the movable handle 112 proximally to clamp the first elongated member 107 and the second elongated member 109 together (e.g., to grip tissue) and/or can actuate the movable handle 112 distally to unclamp the first elongated member 107 and the second elongated member 109 (e.g., to release tissue). Once the first elongated member 107 and the second elongated member 109 are clamped together, a user can transition the selector lever 117 to the unlocked position and can actuate the power trigger 110 to move the gear rack 321 distally using the electric motor 219 of the drivetrain 218. Distal movement of the gear rack 321 can move the blade assembly 616 of the reloadable cartridge assembly 103 distally. Assuming the lockout assembly 617 of the reloadable cartridge assembly 103 has not previously been transitioned to the third state, the blade assembly 616 can be used to cut tissue and/or deliver some or all of the staples in a staple cartridge (e.g., in the first elongated member 107). More specifically, distal movement of the gear rack 321 causes the I-beam 628 of the blade assembly 616 to advance through the elongated member first elongated member 107 and the second elongated member 109. As the I-beam 628 advances through the first elongated member 107 and the second elongated member 109, the I-beam 628 can drive staples from the staple cartridge, through tissue clamped between the first elongated member 107 and the second elongated member 109, and against an anvil to form the driven staples into a tissue holding configuration. The cutting surface 736 of the I-beam 628 may also be used so that stapled tissue is cut.

At any time during the procedure, including immediately after actuating or locking the movable handle 112, before or after actuating the power trigger 110, before or after delivering all or a subset of the staples in the staple cartridge, and/or before or after cutting tissue, a user may desire to unclamp the elongated members 107 and 109 and/or retract the I-beam 628. To do this, the user can transition the selector lever 117 to the reverse position. When set to the reverse (e.g., retract) position, the selector lever 117 can cause the electric motor 219 to retract or move the gear rack 321 proximally, thereby moving the blade assembly 616 attached to the gear rack 321 proximally. As the blade assembly 616 is moved proximally, the I-beam 628 also moves proximally and allows the first elongated member 107 and the second elongated member 109 to separate from one another. When the gear rack 321 is fully reversed, a spike in current can occur as the gear rack 321 is positioned against the retraction spring 356, which can indicate to the system 100 that the gear rack 321 is positioned at its proximal-most position. Thereafter, the drivetrain 218 can change direction move the gear rack 321 in the distal direction a short distance. At this point, the movable handle 112 is permitted to spring to its distal position, and/or the user can either again clamp the elongated members 107 and 109 together or replace the reloadable cartridge assembly 103.

Assuming that the blade assembly 616 was advanced distally far enough to transition the lockout assembly 617 to the second state, the lockout assembly 617 can be transitioned to the third state as the blade assembly 616 is moved proximally. In the third state, lockout assembly 617 prevents subsequent distal movement of the blade assembly 616 that would move the mechanical latch 1052 beyond the lip 1159. Thus, the lockout assembly 617 in the third state prevents intentional or accidental reuse of the reloadable cartridge assembly 103.

2. Associated Methods

A microcontroller or microprocessor (e.g., the microcontroller 580 of the circuit board 255 of FIG. 5A and/or one or more other microcontrollers/microprocessors of the system 100 of FIG. 1) can be used to control and/or automate various aspects or functions of a surgical stapler. Two such aspects/functions are (i) detecting obstacles in the cutting/stapling path of the surgical stapler and (ii) setting and controlling a virtual gear of an electric motor of a surgical handle assembly (e.g., to control tissue cutting and/or stapling speed of the surgical stapler), such as using a lookup table and/or based on encoder information provided to the microcontroller indicating a current position of, for example, an I-beam of a reloadable cartridge assembly.

FIG. 14 is a lookup table 1410 ("the LUT 1410") defining a plurality of virtual gears for an electric motor (e.g., the electric motor 219 of FIG. 2) in accordance with various embodiments of the present technology. In the illustrated embodiment, the LUT 1410 defines seven virtual gears for the electric motor. Each of the virtual gears represents a pairing of a current limit (e.g., in milliamps) for a drivetrain (e.g., the drivetrain 218 of FIG. 2) and a target speed (e.g., a speed limit) for the electric motor (e.g., in pulse width modulation (PWM) level counter control register (CCR) values that can, for example, be pushed from a microcontroller to a motor driver chip). In some embodiments, as the virtual gears for the electric motor increase, the current limits for the drivetrain that are included in the LUT 1410 can also increase. Thus, the current limits (e.g., current limit A through current limit G) in the LUT 1410 can be listed in a generally ascending order from, for example, virtual gear one to virtual gear seven. In these and other embodiments, as the virtual gears of the electric motor increase, the target speeds for the electric motor that are included in the LUT 1410 can decrease. Thus, the target speeds (e.g., speed limit G through speed limit A) in the LUT 1410 can be listed in a generally descending order from, for example, virtual gear one to virtual gear seven. In other words, the current limits included in the LUT 1410 can have a generally inverse relationship with the target speeds included in the LUT 1410 such that (a) lower target speeds for the electric motor are permitted (or are paired with) higher current limits in the drivetrain and/or (b) higher target speeds for the electric motor are permitted (or are paired with) lower current limits in the drivetrain.

Although shown with seven virtual gears in FIG. 14, the LUT 1410 can include a different number of virtual gears (e.g., less than seven virtual gears or more than seven virtual gears) in other embodiments of the present technology. In these and other embodiments, the current limits included in the LUT 1410 can be ordered in a different order (e.g., a non-ascending order, such as a descending order), and/or two or more of the current limits included in the LUT 1410 for different virtual gears can be the same (e.g., equivalent to one another). In these and still other embodiments, the target speeds included in the LUT 1410 can be ordered in a different order (e.g., a non-descending order, such as an ascending order), and/or two or more of the target speeds included in the LUT 1410 for different virtual gears can be the same (e.g., equivalent to one another).

As discussed in greater detail below, a microcontroller (e.g., the microcontroller 580 of FIG. 5A) can utilize the LUT 1410 to set a virtual gear of an electric motor (and therefore current limits for a corresponding drivetrain and target speeds for the electric motor). For example, the microcontroller can set an electric motor to one or more specific virtual gears based at least in part on a position of a gear rack (e.g., the gear rack 321 of FIG. 3) and/or another component (e.g., the I-beam 628 of the blade assembly 616) that is moved or controlled by the electric motor. More specifically, the microcontroller can track the position of (e.g., a portion of) the gear rack and/or the other component using encoder information provided to the microcontroller by an encoder of a corresponding surgical stapling system.

Figure 15:
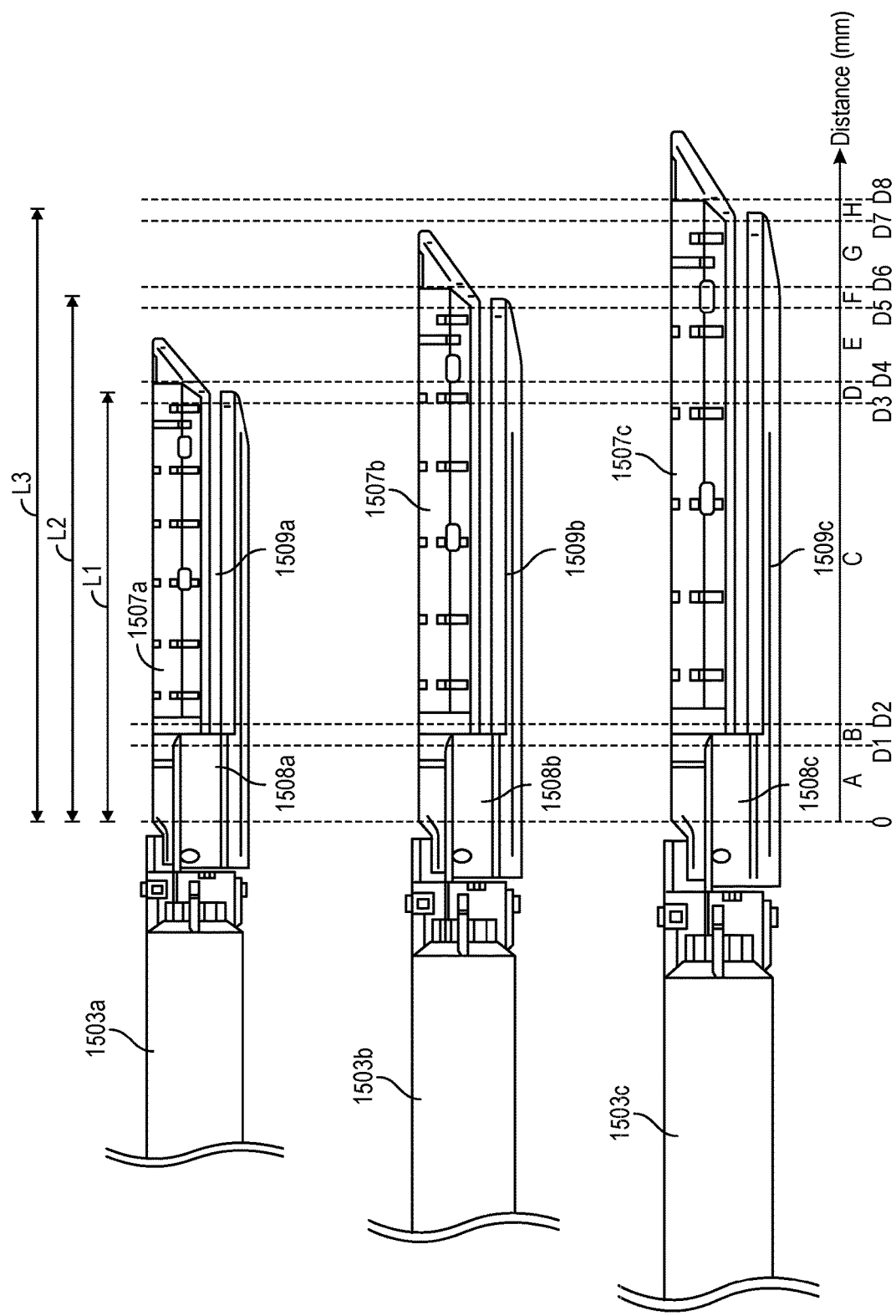
FIG. 15 is a partially schematic diagram illustrating three surgical reloadable cartridge assemblies of differing lengths, each configured in accordance with various embodiments of the present technology.

FIG. 15 is a partially schematic diagram illustrating three surgical reloadable cartridge assemblies 1503*a*, 1503*b*, and 1503*c* configured in accordance with various embodiments of the present technology. Referring first to the surgical reloadable cartridge assembly 1503*c* for the sake of example and clarity, an encoder can track the position of an I-beam (not shown) of the surgical reloadable cartridge assembly 1503*c* along a first elongated member 1507*c* and/or a second elongated member 1509*c* of the surgical reloadable cartridge assembly 1503*c*, and/or relative to an initial position or an initial location of the I-beam (or some other reference point). The initial position/location of the I-beam (shown aligned with an origin of a distance axis illustrated in FIG. 15) can correspond to a position at which the I-beam is located when (a) the surgical reloadable cartridge assembly 1503*c* is releasably attached to a surgical handle assembly (e.g., the surgical handle assembly 102 of FIG. 1) and (b) the surgical handle assembly 102 moves a gear rack (e.g., the gear rack 321 of FIG. 3) to the home position (e.g., to zero out the encoder).

As shown in FIG. 15, distance D8 represents a maximum distance away from the initial position that the I-beam is expected or permitted to travel before reaching an end of its stroke. In some embodiments, the distance D8 can represent a maximum stroke length for strokes of (e.g., blade assemblies, I-beams, and/or other components of) all reloadable cartridge assemblies that are compatible with a surgical handle assembly controlled by the microcontroller. In these and other embodiments, the distance D8 can represent a maximum stroke length for strokes of (e.g., blade assemblies, I-beams, and/or other components of) particular reloadable cartridge assemblies that include the surgical reloadable cartridge assembly 1503*c*. In other words, the microcontroller may know or expect that the blade assembly, I-beam, or another component of the surgical reloadable cartridge assembly 1503*c* will have a stroke with a stroke length L3 that is less than or equal to the maximum distance D8, and may expect that encoder information provided to the microcontroller by the encoder will indicate one or more positions for the I-beam between the initial position and the maximum distance D8. Stated another way, the microcontroller can use encoder information to track a position of a component of the surgical stapler relative to (or along) a maximum stroke for one or more reloadable cartridge assemblies.

The range of potential position values that can be indicated in the encoder information for an I-beam of a reloadable cartridge assembly (e.g., the maximum stroke length for the reloadable cartridge assembly) can be broken into a plurality of zones or regions. In the illustrated example, the range of potential position values for the I-beam of the surgical reloadable cartridge assembly 1503*c* is broken into eight different zones that are labeled zone A through zone H.

Referring first to zone B, the surgical reloadable cartridge assembly 1503*c* can include a lockout assembly (e.g., similar to the lockout assembly 617 of FIGS. 6 and 10-13B) that, when transitioned to a lockout state (e.g., a third state) via prior use of the surgical reloadable cartridge assembly 1503*c*, can prevent the I-beam from advancing distally along the first elongated member 1507*c* and the second elongated member 1509*c* beyond a given point. In some embodiments, the position of a lockout mechanism (e.g., the mechanical latch 1052 of FIG. 10) of the lockout assembly relative to the initial position of the I-beam may be known in advance. As a specific example, the microcontroller may know that, assuming the lockout assembly has been triggered to place the lockout assembly in the lockout state, the I-beam will encounter (either directly or indirectly, such as through the leaves of the blade assembly) a lockout obstacle posed by the lockout mechanism—and therefore be prevented from advancing further distally—when the I-beam is positioned approximately 1 cm from the initial position. Due to manufacturing and/or mechanical tolerances, the actual location the I-beam encounters the lockout obstacle may be slightly before or slightly after the 1 cm anticipated location of the lockout mechanism. Therefore, to account for manufacturing and/or mechanical tolerances, the microcontroller can be provided a minimum distance D1 away from the initial position and a maximum distance D2 away from the initial position that the I-beam is expected to encounter a lockout obstacle (assuming the lockout assembly has been fired) as it is advanced distally from zone A. The range of potential position values for the I-beam that can be indicated in the encoder information while the I-beam is positioned between the distance D1 and the distance D2 away from the initial position can therefore define or correspond to zone B shown in FIG. 15. In other words, zone B can correspond to a range of potential positions for the I-beam in which the microcontroller (a) can expect the I-beam to encounter a lockout obstacle and/or (b) can detect or observe resistance (referred to herein as 'lockout resistance') to further distal movement of the I-beam due to a triggered lockout assembly.

Zone A shown in FIG. 15 can therefore correspond to a range of potential positions for the I-beam (between the initial position and the distance D1 away from the initial position) in which the microcontroller does not expect to detect or observe lockout resistance. Additionally, or alternatively, zone A can correspond to a range of potential positions for the I-beam in which the I-beam is not expected to engage with (e.g., contact, cut, or cause to be stapled) tissue clamped between the first elongated member 1507*c* and the second elongated member 1509*c*. In these and other embodiments, zone A can correspond to a range of potential positions for the I-beam in which the I-beam is not expected to encounter hazardous obstacles to distal movement of the I-beam. For example, zone A can correspond to a range of potential positions for the I-beam in which the I-beam has yet to distally clear a distal end portion of a stabilizing bracket 1508*c* of the surgical reloadable cartridge assembly 1503*c*. In some embodiments, the microcontroller can assume that all or a subset of resistance to distal movement of the I-beam observed while the encoder information indicates that the I-beam is positioned in zone A corresponds to characteristics of tissue clamped between the first elongated member 1507c and the second elongated member 1509c.

Referring now to zone H shown in FIG. 15, the microcontroller can expect that the length L3 of the stroke for the I-beam of the surgical reloadable cartridge assembly 1503c is less than or equal to the maximum distance D8. In other words, the microcontroller can expect that the I-beam will encounter its end of stroke (also referred to herein as an 'end-of-stroke obstruction' or an 'EOS obstruction') when or before the I-beam is positioned the distance D8 away from the initial position. In some embodiments, to account for manufacturing and/or mechanical tolerances, the microcontroller can be provided a distance D7 shown in FIG. 15 that represents a minimum distance from the initial position at which the I-beam is expected to encounter its end of stroke. Therefore, the range of potential positions values that can be indicated in encoder information while the I-beam is positioned between the distance D7 and the maximum distance D8 away from the initial position can define or correspond to zone H. In other words, zone H can correspond to a range of potential positions for the I-beam in which the microcontroller (a) can expect the I-beam to encounter an EOS obstruction and/or (b) can expect to detect or observe resistance (referred to herein as 'EOS resistance') to further distal movement of the I-beam due to the I-beam reaching its end of stroke.

As shown in FIG. 15, the surgical reloadable cartridge assemblies 1503a and 1503b have lengths that are shorter than the length of the surgical reloadable cartridge assembly 1503c. For example, each of the surgical reloadable cartridge assemblies 1503a, 1503b, and 1503c can include one or more rows of staples having a linear length (e.g., between approximately 30 mm and approximately 60 mm). As a specific example, the surgical reloadable cartridge assembly 1503a can include one or more rows of staples having a linear length of approximately 30 mm; the surgical reloadable cartridge assembly 1503b can include one or more rows of staples having a linear length of approximately 45 mm; and the surgical reloadable cartridge assembly 1503c can include one or more rows of staples having a linear length of approximately 60 mm. As such, a stroke length L2 of an I-beam of the surgical reloadable cartridge assembly 1503b is expected to be shorter than the stroke length L3 of the I-beam of the surgical reloadable cartridge assembly 1503c. In other words, the I-beam of the surgical reloadable cartridge assembly 1503b can encounter its end of stroke and/or an EOS obstruction a shorter distance away from the initial position than the I-beam of the surgical reloadable cartridge assembly 1503c. Thus, zone F can correspond to a range of potential positions for the I-beam of the surgical reloadable cartridge assembly 1503b at which the microcontroller (a) can expect the I-beam to encounter an EOS obstruction and/or (b) can expect to detect or observe EOS resistance to further distal movement of the I-beam due to the I-beam reaching its end of stroke. As shown, zone F is inclusive of potential position values that can be indicated in encoder information when the I-beam is positioned between the distance D5 and the distance D6 away from the initial position.

Similarly, a stroke length L1 of an I-beam of the surgical reloadable cartridge assembly 1503a is expected to be shorter than (i) the stroke length L2 of the I-beam of the surgical reloadable cartridge assembly 1503b and (ii) the stroke length L3 of the I-beam of the surgical reloadable cartridge assembly 1503c. In other words, the I-beam of the surgical reloadable cartridge assembly 1503a can encounter its end of stroke and/or an EOS obstruction a shorter distance away from the initial position than the I-beams of the surgical reloadable cartridge assemblies 1503b and 1503c. Thus, zone D can correspond to a range of potential positions for the I-beam of the surgical reloadable cartridge assembly 1503a at which the microcontroller (a) can expect the I-beam to encounter an EOS obstruction and/or (b) can expect to detect or observe EOS resistance to further distal movement of the I-beam due to the I-beam reaching its end of stroke. As shown, zone D is inclusive of potential position values that can be indicated in encoder information when the I-beam is positioned between the distance D3 and the distance D4 away from the initial position.

Zone C (illustrated in FIG. 15 as inclusive of potential position values that can be indicated in encoder information when the I-beams of the surgical reloadable cartridge assemblies 1503a, 1503b, and 1503c are positioned between the distance D2 and the distance D3 away from the initial position) can therefore represent a range of potential positions for the I-beams in which the microcontroller does not expect the I-beams to encounter obstacles and/or resistance to distal movement (e.g., other than from tissue clamped between the first elongated members 1507a, 1507b, and 1507c and the second elongated members 1509a, 1509b, and 1509c, respectively). For example, when encoder information related to the position of the I-beam of the surgical reloadable cartridge assembly 1503c indicates that the I-beam is positioned in zone C, the microcontroller can assume (i) that the lockout assembly of the surgical reloadable cartridge assembly 1503c had not previously been triggered (e.g., indicating that the surgical reloadable cartridge assembly 1503c has not previously been used or fired), (ii) that the I-beam will likely not encounter (either directly or indirectly) a lockout obstacle, (iii) that resistance feedback provided to the microcontroller while the I-beam is in zone C will likely not include a lockout resistance component, (iv) that the I-beam is unlikely to reach its end of stroke and encounter an EOS obstacle while positioned within zone C, and/or (v) that resistance feedback provided to the microcontroller while the I-beam is in zone C will likely not include an EOS resistance component. Similarly, zones E and G (illustrated in FIG. 15 as inclusive of potential position values the can be indicated in encoder information when the I-beams of the surgical reloadable cartridge assemblies 1503a, 1503b, and 1503c are positioned between (i) the distance D4 and the distance D5 away from the initial position and (ii) the distance D6 and the distance D7 away from the initial position, respectively) can represent ranges of potential position values for the I-beams in which the microcontroller does not expect the I-beams to encounter obstacles and/or resistance to distal movement (e.g., other than from tissue clamped between the first elongated members 1507a, 1507b, and 1507c and the second elongated members 1509a, 1509b, and 1509c, respectively).

In some embodiments, the stroke length for an I-beam of a surgical reloadable cartridge assembly may not be known to the microcontroller. For example, a microcontroller may not know (or may be agnostic to) which of the surgical reloadable cartridge assemblies 1503a, 1503b, and/or 1503c is currently attached to a corresponding surgical handle assembly. Therefore, as discussed in greater detail below, the microcontroller can (at least initially) use the same zones A-H (e.g., based on a maximum stroke length) to control the virtual gear of an electric motor, current limits for a corresponding drivetrain, and/or target speeds for the electric motor, regardless of which reloadable cartridge assembly is currently attached to a surgical handle assembly controlled by the microcontroller.

As a specific example, consider a scenario in which the surgical reloadable cartridge assembly 1503b is attached to a surgical handle assembly controlled by the microcontroller. The microcontroller may not know (or may be agnostic to) the stroke length L2 of the I-beam of the surgical reloadable cartridge assembly 1503b. Stated another way, the microcontroller may not know (or may be agnostic to) whether the surgical reloadable cartridge assembly 1503a, the surgical reloadable cartridge assembly 1503b, or the surgical reloadable cartridge assembly 1503c is installed on the surgical handle assembly. As such, the microcontroller may not know whether the I-beam is likely to reach its end of stroke and encounter an EOS obstacle in zone D, zone F, or zone H. Thus, in this scenario, the microcontroller can initially operate under the assumption that the I-beam for the surgical reloadable cartridge assembly 1503b will reach its end of stroke when the encoder information indicates that the I-beam is positioned within zone D.

Continuing with this example, zones A, B, and C in FIG. 15 are the same for each of the surgical reloadable cartridge assemblies 1503a, 1503b, and 1503c. For example, the I-beams for each of the surgical reloadable cartridge assemblies 1503a, 1503b, and 1503c can be expected to travel a same or similar distance across zone A before entering zone B and before the I-beam becomes likely to encounter a lockout obstacle posed by a lockout mechanism of a triggered lockout assembly. Stated another way, the positioning of the lockout mechanism of the lockout assembly can be positioned in a generally same or similar position in each of the surgical reloadable cartridge assemblies 1503a, 1503b, and 1503c. As such, in some embodiments, the microcontroller can control the virtual gears, current limits, and/or target speeds for zones A-C in generally the same manner for all of the surgical reloadable cartridge assemblies 1503a, 1503b, and 1503c.

As discussed above, when encoder information received at the microcontroller indicates that the I-beam for the surgical reloadable cartridge assembly 1503b is positioned within zone D, the microcontroller can control the virtual gears, current limits, and/or target speeds under the assumption that the I-beam is likely to encounter an EOS obstacle at some location within zone D. As shown in FIG. 15, however, the I-beam for the surgical reloadable cartridge assemblies 1503b is unlikely to encounter an EOS obstacle until the I-beam is positioned within zone F. Thus, when encoder information received at the microcontroller indicates that the I-beam has been advanced distally beyond the maximum distance (e.g., distance D4) away from the initial position for zone D, the microcontroller (i) can determine that the stroke length of the stroke for the I-beam of the surgical reloadable cartridge assemblies 1503b is longer than the stroke length L1 and/or (ii) can, at least while the encoder information indicates that the I-beam for the surgical reloadable cartridge assembly 1503b is positioned within zone E, control the virtual gears, current limits, and/or target speeds in a manner generally similar to how the microcontroller controls the virtual gears, current limits, and/or target speeds, respectively, when the encoder information indicates the I-beam is positioned within zone C. As the encoder information indicates that the I-beam has been distally advanced into zone F, the microcontroller can again control the virtual gears, current limits, and/or target speeds under the assumption that the I-beam is likely to encounter an EOS obstacle at some location within zone F. In this example, because the I-beam of the surgical reloadable cartridge assemblies 1503b will reach its end of stroke within zone F, the microcontroller will not make use of zones G and H while the surgical reloadable cartridge assemblies 1503b is attached to the surgical handle assembly controlled by the microcontroller.

In some embodiments, the stroke length (e.g., the maximum stroke length) for the stroke of (e.g., a blade assembly, an I-beam, or another component of) a surgical reloadable cartridge assembly may be made known to the microcontroller. For example, the microcontroller can be provided (e.g., preprogrammed with) a stroke length for the reloadable cartridge assembly before, during, or after attaching the reloadable cartridge assembly to a surgical handle assembly controlled by the microcontroller. In these and other embodiments, the microcontroller can detect or identify a stroke length for a reloadable cartridge assembly, such as by reading identification information on or from (e.g., a chip) of the reloadable cartridge assembly before, during, or after attaching the reloadable cartridge assembly to a surgical handle assembly controlled by the microcontroller.

Figure 16:
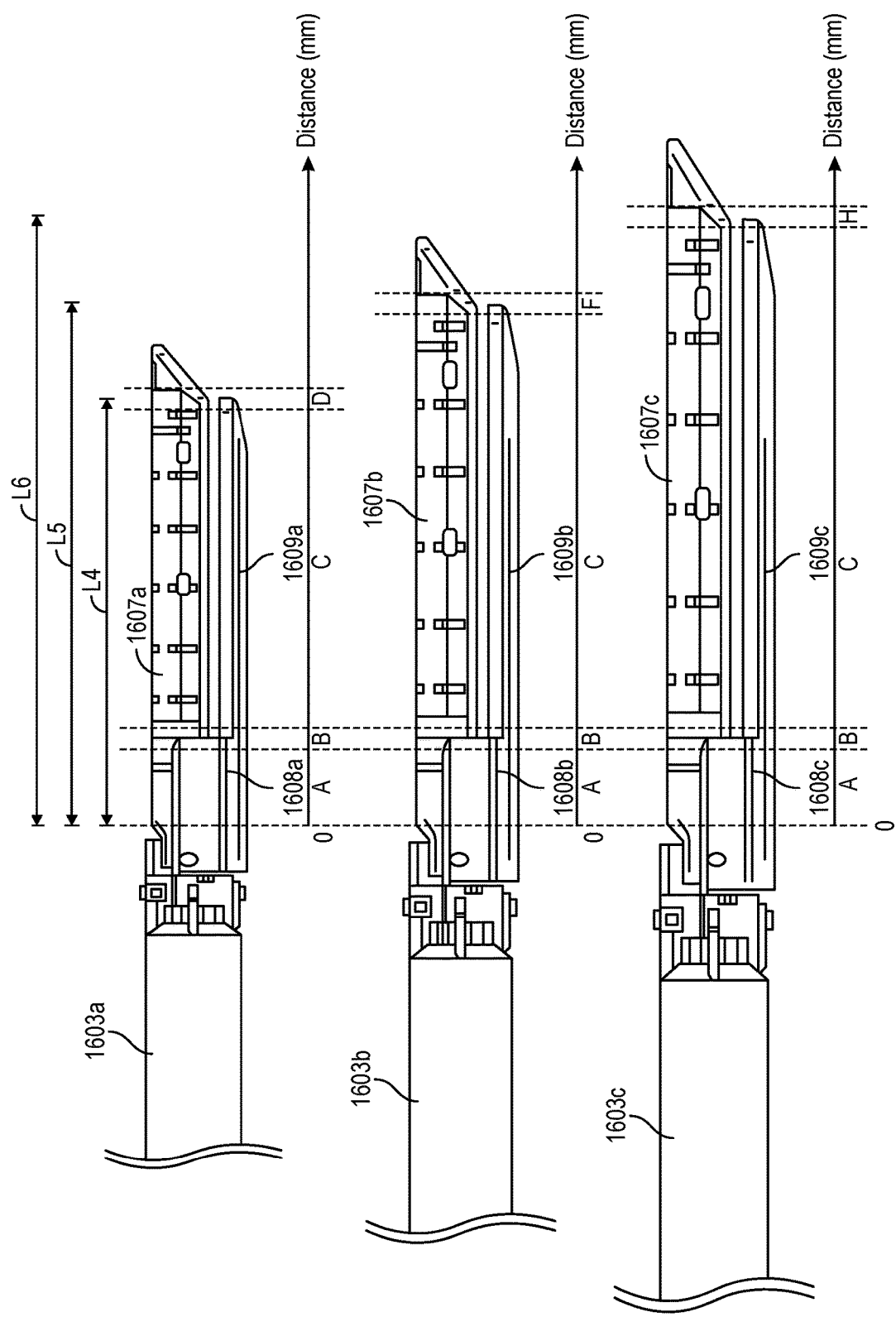
FIG. 16 is a partially schematic diagram illustrating three surgical reloadable cartridge assemblies of differing lengths, each configured in accordance with various embodiments of the present technology.

In some embodiments, when the stroke length for a surgical reloadable cartridge assembly is known to the microcontroller, the microcontroller can employ zones corresponding or unique to that stroke length to control the virtual gears of an electric motor, current limits for a corresponding drivetrain, and/or target speeds for the electric motor. Stated another way, the microcontroller can track a position of a component of the surgical stapler relative to (or along) the known stroke length for a reloadable cartridge assembly. For example, FIG. 16 is a partially schematic diagram illustrating three surgical reloadable cartridge assemblies 1603a, 1603b, and 1603c of differing lengths and corresponding deployment zones. The reloadable cartridge assemblies 1603a, 1603b, and 1603c can be generally similar to the surgical reloadable cartridge assemblies 1503a, 1503b, and 1503c, respectively, of FIG. 15. Therefore, similar reference numbers are used across FIGS. 15 and 16 to denote identical or at least generally similar components. The I-beam of the surgical reloadable cartridge assembly 1603a has a stroke with a stroke length L4, the I-beam of the surgical reloadable cartridge assembly 1603b has a stroke with a stroke length L5, and the I-beam of the surgical reloadable cartridge assembly 1603c has a stroke with a stroke length L6.

As shown in FIG. 16, because the microcontroller is provided the anticipated stroke length for a given I-beam in advance, the microcontroller can use zones corresponding to the known anticipated stroke length. For example, for the surgical reloadable cartridge assembly 1603a, the microcontroller can utilize zones A-D. Zones beyond zone D may not be defined or utilized by the microcontroller, at least while the surgical reloadable cartridge assembly 1603a is attached to the surgical handle assembly controlled by the microcontroller. As another example, for the surgical reloadable cartridge assembly 1603b, the microcontroller can utilize zones A-C and F. Zone D, zone E, and zones beyond zone F may not be defined or utilized by the microcontroller, at least while the surgical reloadable cartridge assembly 1603b is attached to the surgical handle assembly controlled by the microcontroller. As still another example, for the surgical reloadable cartridge assembly 1603c, the microcontroller can utilize zones A-C and H. Zones D-G and zones beyond zone H may not be defined or utilized by the microcontroller, at least while the surgical reloadable cartridge assembly 1603c is attached to the surgical handle assembly controlled by the microcontroller.

As also shown in FIG. 16, zones used by the microcontroller can have different sizes or different potential position value ranges depending on the known anticipated stroke length for an I-beam of a given reloadable cartridge assembly. For example, the range of potential position values that can be included in encoder information for zone C when the surgical reloadable cartridge assembly 1603c is installed can be larger than the range of potential position values that can included in encoder information for zone C when the surgical reloadable cartridge assembly 1603a or the reloadable cartridge assembly 1603b is installed. As another example, although the zones A and B are shown as generally the same size and as being positioned at generally the same locations relative to the initial positions across the surgical reloadable cartridge assemblies 1603a, 1603b, and 1603c, the sizes and/or positions of the zones A and/or B can vary across the surgical reloadable cartridge assemblies 1603a, 1603b, and 1603c in other embodiments. As still another example, although the zones D, F, and H are shown as generally the same size as one another and as zone B, the sizes the zones D, F, and/or H can vary from one another and/or from zone B across the surgical reloadable cartridge assemblies 1603a, 1603b, and 1603c in other embodiments.

As discussed above, a microcontroller (e.g., the microcontroller 580 of the circuit board 255 of FIG. 5A and/or one or more other microcontrollers/microprocessors of the system 100 of FIG. 1) can be used to control and/or automate various aspects or functions of a surgical stapler, such as (i) detecting obstacles in the cutting/stapling path of the surgical stapler and/or (ii) setting and controlling a virtual gear of an electric motor of a surgical handle assembly (e.g., to control tissue cutting and/or stapling speed of the surgical stapler). For example, when an I-beam of a reloadable cartridge assembly encounters a lockout obstacle posed by a triggered lockout assembly and/or when the I-beam reaches its end of stroke, continued attempts to advance the I-beam distally can result in damage to the reloadable cartridge assembly and/or inadvertent damage to tissue. Thus, it can be important for the microcontroller to, while the I-beam is being advanced distally to cut and/or staple tissue, distinguish between resistive feedback from tissue (through which the I-beam can pass by cutting and/or stapling the tissue) and resistive feedback from obstructions (through which the I-beam cannot pass without hazard) such as an engaged single-use lockout mechanism, a surgical instrument in the path of the stapler, and/or an end of stapler stroke.

Figure 17:
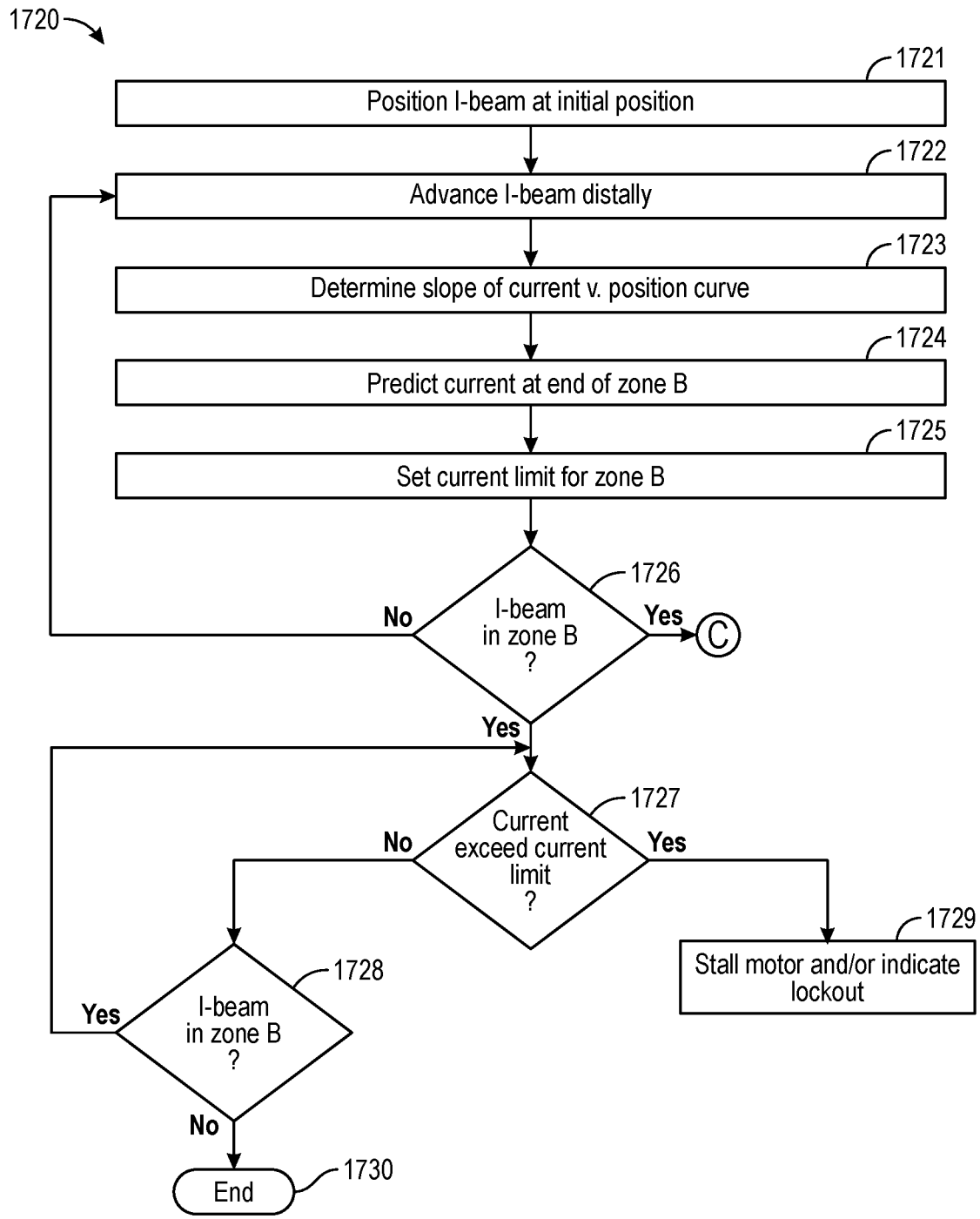
FIG. 17 is a flow diagram illustrating a single use lockout method in accordance with various embodiments of the present technology.

FIG. 17 is a flow diagram illustrating a method 1720 in accordance with various embodiments of the present technology. In some embodiments, the method 1720 can be employed while an electric motor of a surgical handle assembly is used to distally advance an I-beam of an attached reloadable cartridge assembly, for example, through zones A and/or B of FIGS. 15 and 16. In these and other embodiments, the method 1720 can be employed to distinguish between (i) resistive feedback from tissue clamped between a first elongated member and a second elongated member of the reloadable cartridge assembly and through which the I-beam can be advanced (e.g., to cut and staple the tissue) and (ii) resistive feedback corresponding to a lockout obstacle (e.g., beyond which there is a risk of cutting tissue without stapling, such as because the reloadable cartridge assembly has been previously used or fired). In these and still other embodiments, the method 1720 can be used to set (e.g., dynamically set) a virtual gear of an electric motor, a target speed for the electric motor, and/or a current limit for a corresponding drivetrain (e.g., for use while the I-beam is advanced through zone B and/or another zone in which it is likely or expected that the I-beam can encounter an obstacle). Additionally, or alternatively, the method 1720 can be employed to detect when (i) a lockout assembly has previously been triggered and/or (ii) a lockout mechanism (e.g., a mechanical latch) of the lockout assembly is preventing or hindering further distal movement of the I-beam. In these and other embodiments, the method 1720 can be employed to determine when to stall the electric motor and/or abort firing the reloadable cartridge assembly.

The method 1720 is illustrated as a set of steps or blocks 1721-1730. All or a subset of one or more of the blocks 1721-1730 can be executed by various components of a surgical stapling system, such as by a surgical handle assembly and/or a reloadable cartridge assembly. For example, all or a subset of one or more of the blocks 1721-1730 can be executed by a microcontroller, an electric motor, a drivetrain, a gear rack, a drive shaft, a blade assembly, an I-beam, a first elongated member, and/or a second elongated member. Furthermore, all or a subset of one or more of the blocks 1721-1730 can be executed by a user or operator of the surgical stapling system. Moreover, all or a subset of one or more of the blocks 1721-1730 can be executed in accordance with the discussion above.

Figure 18A:
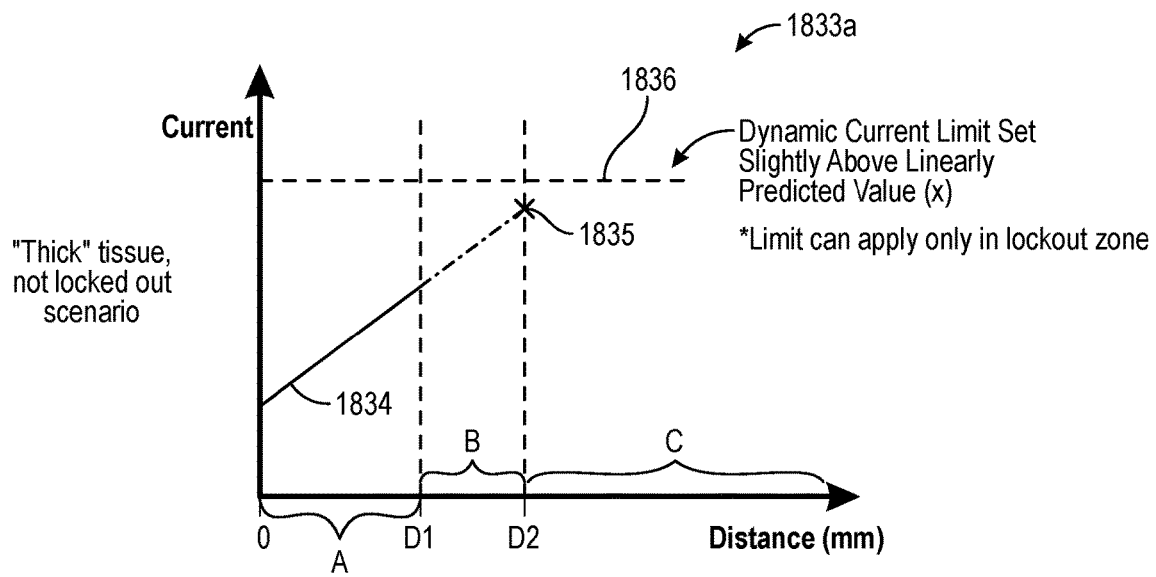
FIGS. 18A and 18B are plots illustrating a dynamic setting of a current limit for thick tissue in accordance with various embodiments of the present technology.
Figure 18B:
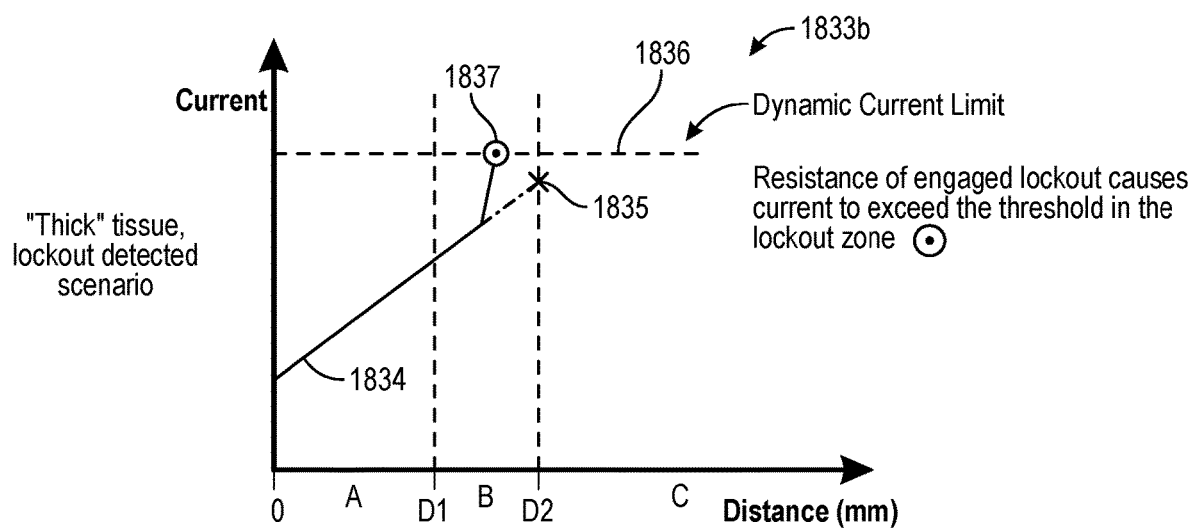
Figure 19A:
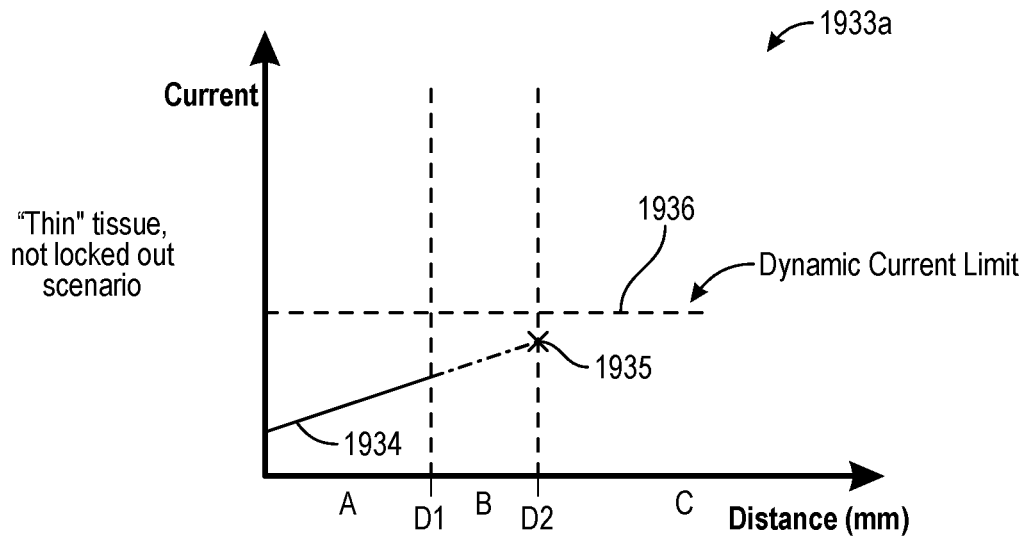
FIGS. 19A and 19B are plots illustrating a dynamic setting of a current limit for thin tissue in accordance with various embodiments of the present technology.
Figure 19B:
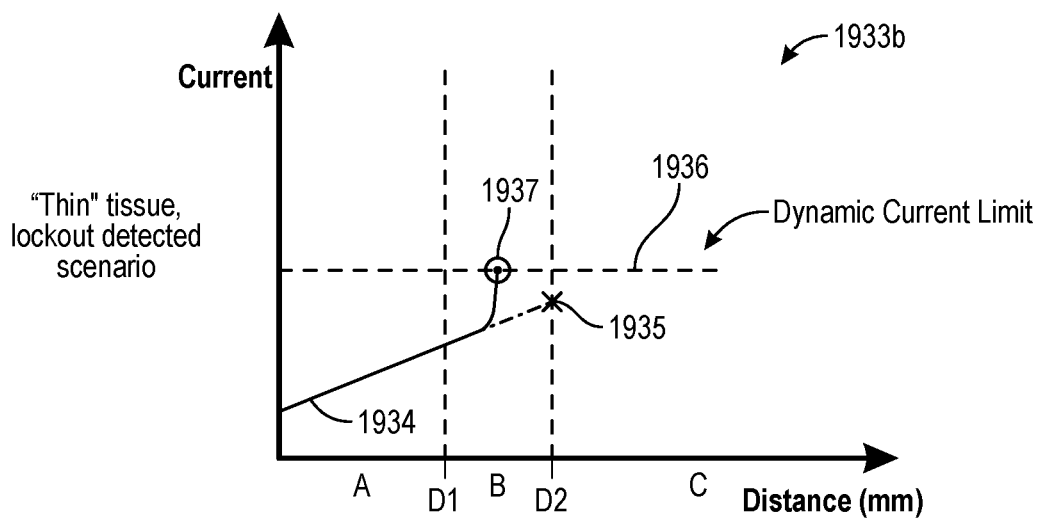

The method 1720 is discussed in detail below with repeated reference to zones A and B of FIGS. 15 and 16, and to FIGS. 18A-19B. FIGS. 18A and 18B are plots 1833a and 1833b, respectively, illustrating a dynamic setting of a current limit for thick tissue in accordance with various embodiments of the present technology. FIGS. 19A and 19B are plots 1933a and 1933b, respectively, illustrating a dynamic setting of a current limit for thin tissue in accordance with various embodiments of the present technology.

The method 1720 can begin at block 1721 by positioning an I-beam (e.g., of a reloadable cartridge assembly attached to a surgical handle assembly controlled by a microcontroller) at an initial position. As discussed above, the initial position of the I-beam can correspond to a location at which the I-beam is positioned when (a) the surgical reloadable cartridge assembly is releasably attached to the surgical handle assembly and (b) the surgical handle assembly moves a gear rack to the home position. Thus, positioning the I-beam at the initial position can include retracting a gear rack until the gear rack is in its proximal-most position. In some embodiments, positioning the I-beam at the initial position can include zeroing out encoder information captured or generated by an encoder of the system. As discussed above, the encoder information can indicate a position of the I-beam, such as relative to the initial position. In some embodiments, positioning the I-beam at the initial position can include advancing the gear rack and/or the I-beam distally by a small amount (e.g., after moving the gear rack to the proximal-most position) to position the gear rack at the loading position.

At block 1722, the method can continue by advancing the I-beam distally. Advancing the I-beam distally can include clamping the first elongated member and the second elongated member together (e.g., such that the first elongated member and the second elongated member clamp down on and hold tissue between the first elongated member and the second elongated member). Advancing the I-beam distally can include advancing the I-beam distally using a drivetrain, electric motor, gear rack, and/or drive shaft of the surgical handle assembly and/or a blade assembly of the reloadable cartridge assembly. Advancing the I-beam distally can include setting and/or controlling (e.g., updating, adjusting, changing) a virtual gear of the electric motor, such as using a LUT (e.g., the LUT 1410 of FIG. 14) and/or in accordance with or in a manner generally similar to the method 2150 described in greater detail below with reference to FIG. 21. Advancing the I-beam distally can include setting and/or controlling (e.g., updating, adjusting, changing) a current limit for the drivetrain and/or a target speed for the electric motor. Advancing the I-beam distally can include (e.g., continuously or periodically) tracking a position (e.g., a current position) of the I-beam, such as using encoder information generated by and/or received from the encoder. In these and other embodiments, advancing the I-beam distally can include tracking and/or recording the position of the I-beam over time, tracking and/or recording measurements of current observed in the drivetrain over time, and/or tracking and/or recording speeds of the electric motor over time. Advancing the I-beam distally can include advancing the I-beam distally through zone A and/or zone B.

At blocks 1723-1725, the method 1720 can continue by (a) determining a slope (e.g., a rate of change) of current observed in the drivetrain versus position of the I-beam (block 1723); (b) predicting current observed in the drivetrain when the I-beam reaches an end of (or some other point within) zone B (block 1724); and (c) setting a current limit for current in the drivetrain for when the I-beam is distally advanced through zone B (block 1725). For example, the method 1720 can track current observed in the drivetrain versus the position of the I-beam as the I-beam is advanced distally across zone A.

It is expected that a slope of a resulting curve (determined at block 1723) can depend at least in part on characteristics of tissue clamped between the first elongated member and the second elongated member. More specifically, current observed in the drivetrain at a given time can provide an indication of an amount of resistance encountered to distal movement of the I-beam at that given time. Thus, higher current values in the drivetrain can indicate higher resistances encountered to distal movement of the I-beam, and lower current in the drivetrain can indicate lower resistances encountered to distal movement of the I-beam. As discussed above with reference to FIG. 15, it is expected that resistance observed while the I-beam is advanced distally across zone A can largely or solely be attributed to resistance supplied by tissue clamped between the first elongated member and the second elongated member (e.g., because the I-beam has yet to be advanced distally far enough to clear a distal end of a stabilizing bracket of the reloadable cartridge assembly and/or to encounter obstacles or other potential sources of resistance). As such, it is expected that a slope of a curve representing current in the drivetrain versus the position of the I-beam as the I-beam is advanced distally across zone A will be positively correlated with an amount of tissue and/or the thickness (or density) of the tissue clamped between the first elongated member and the second elongated member. In other words, it is expected that the slope of the curve determined at block 1723 will be greater or steeper when a larger amount of tissue and/or when thicker/denser tissue is clamped between the first elongated member and the second elongated member. Stated another way, it is expected that the slope of the curve determined at block 1723 will be lesser or flatter when a smaller amount of tissue and/or when thinner/less dense tissue is clamped between the first elongated member and the second elongated member. Therefore, it is expected that the slope of the curve determined at block 1723 as the I-beam is advanced distally across zone A will provide a baseline indication of an amount of resistance to distal movement of the I-beam provided by the tissue.

Because the resistance supplied by the tissue is expected to increase as the I-beam comes into contact with the tissue, begins to cut the tissue, and/or causes the tissue to be stapled, such a baseline can be helpful in later distinguishing between resistance provided by the tissue and resistance provided by another source, such as an obstacle encountered by the I-beam. In particular, the method 1720 can, at block 1724, predict a current level that will be observed in the drivetrain when the I-beam reaches an end of (or some other point within) zone B. The predicted current value can be based at least in part on the slope determined at block 1723. For example, using the slope, the method 1720 can (e.g., linearly) extrapolate the curve used at block 1723 and/or perform another suitable analysis (e.g., a curve fit) to calculate the predicted current level.

Once the predicted current level is calculated/obtained, the method 1720 can (at block 1725) set a current limit for the drivetrain for when the I-beam is advanced distally across zone B. The current limit can depend at least in part on the predicted current value. For example, the current limit can be set equal to the predicted current value or can be set a threshold amount (e.g., 20 percent, 15 percent, 10 percent, 5 percent, and/or another suitable percentage or amount) above the predicted current value. In some embodiments, the threshold amount can account for an anticipated margin of error in the prediction and/or for moderate deviation from the extrapolation of the curve at block 1724 that still remains indicative of resistance supplied mostly or solely by tissue.

In these and other embodiments, the current limit can be set to a current limit specified in a LUT (e.g., the LUT 1410 of FIG. 14). For example, the method 1720 can set the current limit at block 1725 to a current limit in the LUT that is the closest, the second to closest, the third to closest, etc. to the predicted current level from block 1724 from among the current limits in the LUT that exceed the predicted current level from block 1724. In some embodiments, the method 1720 may also set a target speed for the electric motor to a target speed that is paired in the LUT with the current limit selected at block 1725.

Dynamically setting the current limit for the drivetrain in this manner at block 1725 is expected to reduce the number of false positives, defined as stalling the electric motor and/or providing an indication of lockout based on incorrectly determining that a lockout assembly has been previously fired/engaged. After setting the current limit at block 1725, the method 1720 can proceed to block 1726.

Referring to the plot 1833*a* of FIG. 18A for the sake of example and clarity, a curve 1834 is shown that represents current observed in the drivetrain as the I-beam is advanced distally across zone A. A prediction 1835 of current that will be observed in the drivetrain when the I-beam is advanced distally to the end of zone B can be calculated/obtained using the slope of the curve 1834 from zone A and/or by extrapolating the curve 1834 across zone B. In turn, a current limit 1836 can be set a threshold amount above the prediction 1835. As discussed in greater detail below, the current limit 1836 can be a limit for current in the drivetrain as the I-beam is advanced distally across zone B, and can be used to detect engagement with a lockout mechanism of a lockout assembly of the reloadable cartridge assembly.

Referring now to the plot 1933*a* of FIG. 19A for the sake of comparison with the plot 1833*a* of FIG. 18A, a curve 1934 is shown in FIG. 19A that represents current observed in the drivetrain as the I-beam is advanced distally across zone A with different tissue clamped between the first elongated member and the second elongated member. As can be seen by comparing the plot 1833*a* (FIG. 18A) with the plot 1933*a* (FIG. 19A), the slope of the curve 1934 in FIG. 19A is less than/flatter than the slope of the curve 1834 of FIG. 18A. This can indicate that a lesser amount of tissue and/or thinner/less dense tissue is clamped between the first elongated member and the second elongated member when generating the curve 1934 than is clamped between the first elongated member and the second elongated member when generating the curve 1834 of FIG. 18A. As such, it is expected that the tissue clamped between the first elongated member and the second elongated member when generating the curve 1934 will provide less resistance to distal movement of the I-beam across the zone B than the resistance provided by the tissue corresponding to the plot 1833*a* of FIG. 18A. Indeed, this can be seen by (i) the fact that a prediction 1935 (FIG. 19A) of current that will be observed in the drivetrain when the I-beam is advanced distally to the end of zone B is less than the prediction 1835 (FIG. 18A), and (ii) the fact that a current limit 1936 (FIG. 19A) set for the drivetrain based at least in part on the slope of the curve 1934 and the prediction 1935 is lower than the current limit 1836 (FIG. 18A).

Referring again to FIG. 17, the method 1720 can continue at block 1726 by determining whether the I-beam is currently positioned within zone B (e.g., of FIGS. 15 and/or 16). In some embodiments, determining whether the I-beam is currently positioned within zone B includes monitoring encoder information generated by and/or received from the encoder and/or determining a position (e.g., a current position) of the I-beam based at least in part on the encoder information. In the event the I-beam is not currently positioned within zone B (block 1726: No), the method 1720 can return to one or more of blocks 1722-1725. For example, the method 1720 can return to block 1722 to continue to advance the I-beam distally. Additionally, or alternatively, the method 1720 can return to block 1723, block 1724, and/or block 1725 to, for example, determine an updated slope value for the current v. position curve, an updated prediction of the current that will be observed in the drivetrain when the I-beam reaches the end of (or another point within) zone B, and/or an updated current limit, respectively. On the other hand, in the event that the I-beam is currently positioned within zone B (block 1726: Yes), the method 1720 can proceed to block 1727. In some embodiments, in the event that the I-beam is currently positioned within zone B (block 1726: Yes), the method 1720 can additionally, or alternatively, proceed to block 2371 of method 2370 discussed in greater detail below with reference to FIG. 23.

At block 1727, the method 1720 can continue by determining whether current observed in the drivetrain while advancing the I-beam across zone B exceeds (or meets) the current limit set at block 1725. In the event the method 1720 determines that the current observed in the drivetrain does not exceed the current limit (block 1727: No), the method 1720 can proceed to block 1728 to again determine whether the I-beam is currently positioned within zone B. If, at block 1728, the method 1720 determines that the I-beam is still within zone B (block 1728: Yes), the method 1720 can return to block 1727. On the other hand, in the event the method 1720 determines that the I-beam is not (block 1728: No) currently within zone B (e.g., indicating that the I-beam has been fully advanced distally across zone B or that the I-beam has been retracted proximally back into zone A), the method 1720 can proceed to block 1730 to terminate.

In some embodiments, the method 1720 can optionally determine whether the I-beam is currently positioned within zone A before proceeding from block 1728 to block 1730. In the event that the method 1720 determines that the I-beam is currently positioned within zone A, the method 1720 can determine that the I-beam was retracted proximally from zone B. In this scenario, the method 1720 can terminate and/or return to one or more of blocks 1721-1725.

Returning to block 1727, in the event the method 1720 determines that the current observed in the drivetrain exceeds (or meets) the current limit (block 1727: Yes), the method 1720 can proceed to block 1729. At block 1729, the method 1720 can continue by (i) stalling (e.g., disabling, cutting power to, stop from driving) the electric motor such that attempts to distally advance the I-beam are ceased and/or (ii) indicating to a user/operator that a lockout obstacle has been detected. The indication can be a visual indication (e.g., a specific color of light (e.g., red, yellow), a flashing or solid pattern of light(s), etc. emitted, for example, by an LED on the surgical handle assembly) and/or an audio indication (e.g., beeps or other sounds, such as of a specific frequency or pitch). In some embodiments, when the method 1720 determines that the current observed in the drivetrain exceeds (or meets) the current limit, the method 1720 can retract the I-beam proximally by an amount before stalling the electric motor (e.g., to relieve force exerted on the lockout obstacle or another obstacle that caused the current spike). In some embodiments, at this time, a user/operator can optionally retract the I-beam proximally.

Referring to the plot 1833*b* of FIG. 18B and the plot 1933*b* of FIG. 19B for the sake of example and clarity, as the I-beam is advanced across zone B, current observed in the drivetrain spikes to point 1837 in FIG. 18B and to point 1937 in FIG. 19B. Points 1837 and 1937 both meet or exceed the current limits 1836 and 1936, respectively. Therefore, the spikes in current can be detected at block 1727 of the method 1720. As discussed above, current in the drivetrain while advancing the I-beam distally can provide an indication of resistance to distal movement of the I-beam. Thus, a spike in current observed in the drivetrain can indicate an obstacle in the path of the I-beam, especially when coupled with little to no change in the position of the I-beam (as is shown in FIGS. 18B and 19B). As discussed above with reference to FIG. 15, zone B can correspond to a range of positions for the I-beam at which the I-beam is likely to encounter a lockout obstruction posed by a lockout mechanism of a lockout assembly of the reloadable cartridge assembly, assuming the lockout assembly has been previously triggered/engaged (e.g., via prior use and/or firing of the reloadable cartridge assembly). Therefore, as the method 1720 detects (at block 1727) the spikes in current corresponding to the points 1837 and 1937 in FIGS. 18B and 19B and/or the little to no change in position of the I-beam, the method 1720 can (a) determine that the lockout assembly for the reloadable cartridge assembly has previously been triggered/engaged and/or (b) can prevent or hinder further distal advancement of the I-beam (e.g., to reduce the risk of cutting tissue without stapling the tissue).

On the other hand, in the event that the method 1720 detects no violations of the current limits 1836 and 1936 of FIGS. 18B and 19B (and/or no violations of the current limits 1836 and 1936 coupled with little to no changes in position of the I-beam) before the I-beam is fully advanced distally across zone B, the method 1720 (*i*) can determine that the lockout assembly for the reloadable cartridge assembly has not previously been triggered/engaged and/or (ii) can permit the I-beam to be advanced further distally (e.g., to cut and/or staple the tissue).

Although the steps 1721-1730 of the method 1720 are discussed and illustrated in a particular order, the method 1720 of FIG. 17 is not so limited. In other embodiments, the steps 1721-1730 of the method 1720 can be performed in a different order. In these and other embodiments, any of the steps 1721-1730 of the method 1720 can be performed before, during, and/or after any of the other steps 1721-1730 of the method 1720. For example, the I-beam can be advanced distally (block 1722) before, during, and/or after executing all or a subset of blocks 1723-1728. As another example, the blocks 1723-1725 can be performed during or after the block 1726. Furthermore, a person of ordinary skill in the relevant art will recognize that the illustrated method 1720 can be altered and still remain within these and other embodiments of the present technology. For example, one or more of the blocks 1721-1730 of the method 1720 illustrated in FIG. 17 can be omitted (e.g. block 1729) and/or repeated (e.g., all or a subset of one or more of blocks 1721-1728) in some embodiments. Moreover, although discussed in detail above with reference to advancing an I-beam distally through zones A and B, all or a subset of one or more of the blocks 1721-1730 can be performed (i) while retracting an I-beam proximally through the zones A and/or B and/or (ii) while advancing an I-beam distally and/or retracting an I-beam proximally through one or more other zones, such as zones at ends of strokes (e.g., zones D, F, and H of FIGS. 15 and 16). In embodiments in which advancing the I-beam distally includes advancing the I-beam distally through another zone in addition to or in lieu of zone A and/or zone B, advancing the I-beam distally can include cutting and/or stapling the tissue held between the first elongated member and the second elongated member.

Figure 20:
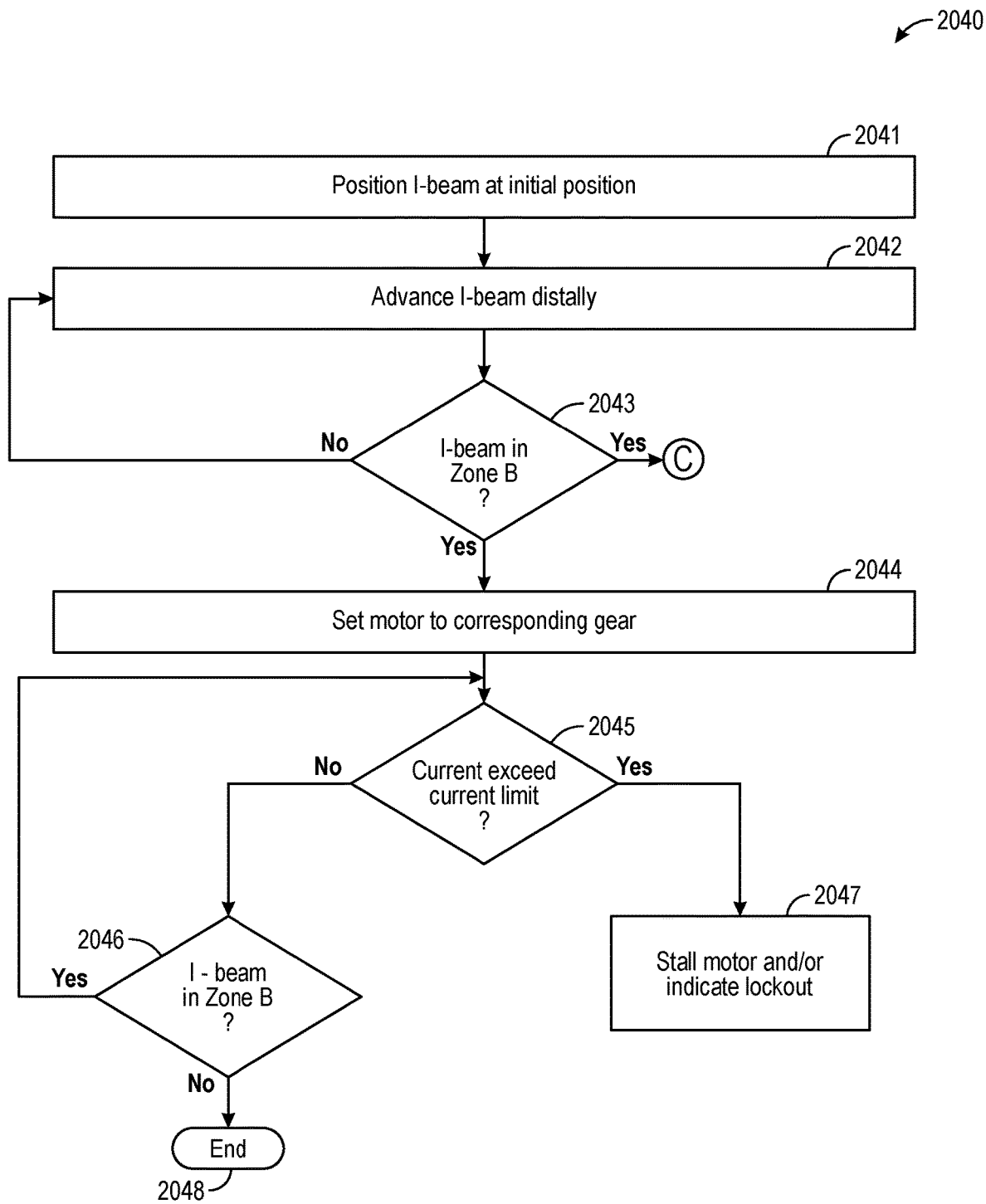
FIG. 20 is a flow diagram illustrating another single use lockout method in accordance with various embodiments of the present technology.

FIG. 20 is a flow diagram illustrating another method 2040 in accordance with various embodiments of the present technology. In some embodiments, the method 2040 can be employed while an electric motor of a surgical handle assembly is used to distally advance an I-beam of an attached reloadable cartridge assembly, for example, through zones A and/or B of FIGS. 15 and 16. In these and other embodiments, the method 2040 can be employed to distinguish between (i) resistive feedback from tissue clamped between a first elongated member and a second elongated member of the reloadable cartridge assembly and through which the I-beam can be advanced (e.g., to cut and staple the tissue) and (ii) resistive feedback corresponding to a lockout obstacle (e.g., beyond which there is a risk of cutting tissue without stapling, such as because the reloadable cartridge assembly has been previously used or fired). In these and still other embodiments, the method 2040 can be used to set a virtual gear of an electric motor, a target speed for the electric motor, and/or a current limit for a corresponding drivetrain (e.g., for use while the I-beam is advanced through zone B and/or another zone in which it is likely or expected that the I-beam can encounter an obstacle). Additionally, or alternatively, the method 2040 can be employed to detect when (i) a lockout assembly has previously been triggered and/or (ii) a lockout mechanism (e.g., a mechanical latch) of the lockout assembly is preventing or hindering further distal movement of the I-beam. In these and other embodiments, the method 2040 can be employed to determine when to stall the electric motor and/or abort firing the reloadable cartridge assembly.

The method 2040 is illustrated as a set of steps or blocks 2041-2048. All or a subset of one or more of the blocks 2041-2048 can be executed by various components of a surgical stapling system, such as by a surgical handle assembly and/or a reloadable cartridge assembly. For example, all or a subset of one or more of the blocks 2041-2048 can be executed by a microcontroller, an electric motor, a drivetrain, a gear rack, a drive shaft, a blade assembly, an I-beam, a first elongated member, and/or a second elongated member. Furthermore, all or a subset of one or more of the blocks 2041-2048 can be executed by a user or operator of the surgical stapling system. Moreover, all or a subset of one or more of the blocks 2041-2048 can be executed in accordance with the discussion above. The method 2040 is discussed in detail below with repeated reference to the LUT 1410 of FIG. 14 and to zones A and B of FIGS. 15 and 16.

The method 2040 can begin at block 2041 by positioning an I-beam (e.g., of a reloadable cartridge assembly attached to a surgical handle assembly controlled by a microcontroller) at an initial position. Positioning the I-beam at the initial position at block 2041 of the method 2040 can be generally similar to positioning an I-beam at an initial position at block 1721 of the method 1720 of FIG. 17 discussed in detail above.

At block 2042, the method 2040 can continue by advancing the I-beam distally. Advancing the I-beam distally at block 2042 of the method 2040 can be generally similar to advancing the I-beam distally at block 1722 of the method 1720 of FIG. 17 discussed in detail above.

At block 2043, the method 2040 can continue by determining whether the I-beam is currently positioned within zone B (e.g., of FIGS. 15 and/or 16). Determining whether the I-beam is currently positioned within zone B at block 2043 of the method 2040 can be generally similar to determining whether the I-beam is currently positioned within zone B at block 1726 of the method 1720 of FIG. 17. In the event the I-beam is not currently positioned within zone B (block 2043: No), the method 2040 can optionally return to block 2042 to continue to advance the I-beam distally. On the other hand, in the event the I-beam is currently positioned within zone B (block 2043: Yes), the method 2040 can proceed to block 2044. In some embodiments, in the event that the I-beam is currently positioned within zone B (block 2043: Yes), the method 2040 can additionally, or alternatively, proceed to block 2371 of the method 2370 discussed in greater detail below with reference to FIG. 23.

At block 2044, the method 2040 can continue by setting the electric motor to a virtual gear for moving the I-beam distally across zone B. In some embodiments, the virtual gear can be a preset or predetermined virtual gear for moving the I-beam distally across zone B. For example, the virtual gear can be a specific gear in the LUT 1410 of FIG. 14. As a specific example, the virtual gear can be gear 4 in the LUT 1410. Setting the electric motor to the virtual gear can include setting a current limit for the drivetrain and/or a target speed for the electric motor. The current limit and/or the target speed can correspond to the virtual gear. Continuing with the above example in which the virtual gear is gear 4 in the LUT 1410, setting the electric motor to the virtual gear can include (i) setting a current limit for the drivetrain to current limit D and (ii) setting a target speed for the electric motor to target speed D. Setting the electric motor to the virtual gear can include setting the electric motor to a virtual gear that provides enough force for the I-beam to clamp the first elongated member and the second elongated member together on tissue and/or to begin cutting and/or stapling the tissue, but not enough force to damage or bypass a lockout mechanism of a lockout assembly of the reloadable cartridge assembly in the event the lockout assembly has previously been triggered/engaged.

At block 2045, the method 2040 can continue by determining whether current observed in the drivetrain while advancing the I-beam across zone B exceeds (or meets) the current limit set at block 2044 corresponding to the virtual gear of the electric motor. In the event that the method 2040 determines that the current observed in the drivetrain does not exceed the current limit (block 2045: No), the method 2040 can proceed to block 2046 to again determine whether the I-beam is currently positioned within zone B. If, at block 2046, the method 2040 determines that the I-beam is still within zone B (block 2046: Yes), the method 2040 can return to block 2045. On the other hand, in the event the method 2040 determines that the I-beam is not (block 2046: No) currently within zone B (e.g., indicating that the I-beam has been fully advanced distally across zone B or that the I-beam has been retracted proximally back into zone A), the method 2040 can proceed to block 2048 to terminate.

In some embodiments, the method 2040 can optionally determine whether the I-beam is currently positioned within zone A before proceeding from block 2046 to block 2048. In the event that the method 2040 determines that the I-beam is currently positioned within zone A, the method 2040 can determine that the I-beam was retracted proximally from zone B. In this scenario, the method 2040 can terminate or return to one or more of blocks 2041 and/or 2042.

Returning to block 2045, in the event the method 2040 determines that the current observed in the drivetrain exceeds (or meets) the current limit (block 2045: Yes) and/or exceeds (or meets) the current limit with little to no change in position of the I-beam, the method 2040 can proceed to block 2047. At block 2047, the method 2040 can continue by (i) stalling (e.g., disabling, cutting power to, stop from driving) the electric motor such that attempts to distally advance the I-beam are ceased and/or (ii) indicating to a user/operator that a lockout obstacle has been detected. Block 2047 of the method 2040 can be generally similar to block 1729 of the method 1720 of FIG. 17 discussed above.

Although the steps 2041-2048 of the method 2040 are discussed and illustrated in a particular order, the method 2040 of FIG. 20 is not so limited. In other embodiments, the steps 2041-2048 of the method 2040 can be performed in a different order. In these and other embodiments, any of the steps 2041-2048 of the method 2040 can be performed before, during, and/or after any of the other steps 2041-2048 of the method 2040. For example, the I-beam can be advanced distally (block 2042) before, during, and/or after executing all or a subset of blocks 2043-2046. As another example, the blocks 2043 and/or 2044 can be performed during or after block 2045 and/or 2046. Furthermore, a person of ordinary skill in the relevant art will recognize that the illustrated method 2040 can be altered and still remain within these and other embodiments of the present technology. For example, one or more of the blocks 2041-2048 of the method 2040 illustrated in FIG. 20 can be omitted (e.g. block 2047) and/or repeated (e.g., all or a subset of one or more of blocks 2041-2046) in some embodiments. Moreover, although discussed in detail above with reference to advancing an I-beam distally through zones A and B, all or a subset of one or more of the blocks 2041-2048 can be performed (i) while retracting an I-beam proximally through the zones A and/or B and/or (ii) while advancing an I-beam distally and/or retracting an I-beam proximally through one or more other zones, such as zones at ends of strokes (e.g., zones D, F, and H of FIGS. 15 and 16). In embodiments in which advancing the I-beam distally includes advancing the I-beam distally through another zone in addition to or in lieu of zone A and/or zone B, advancing the I-beam distally can include cutting and/or stapling the tissue held between the first elongated member and the second elongated member.

Figure 21:
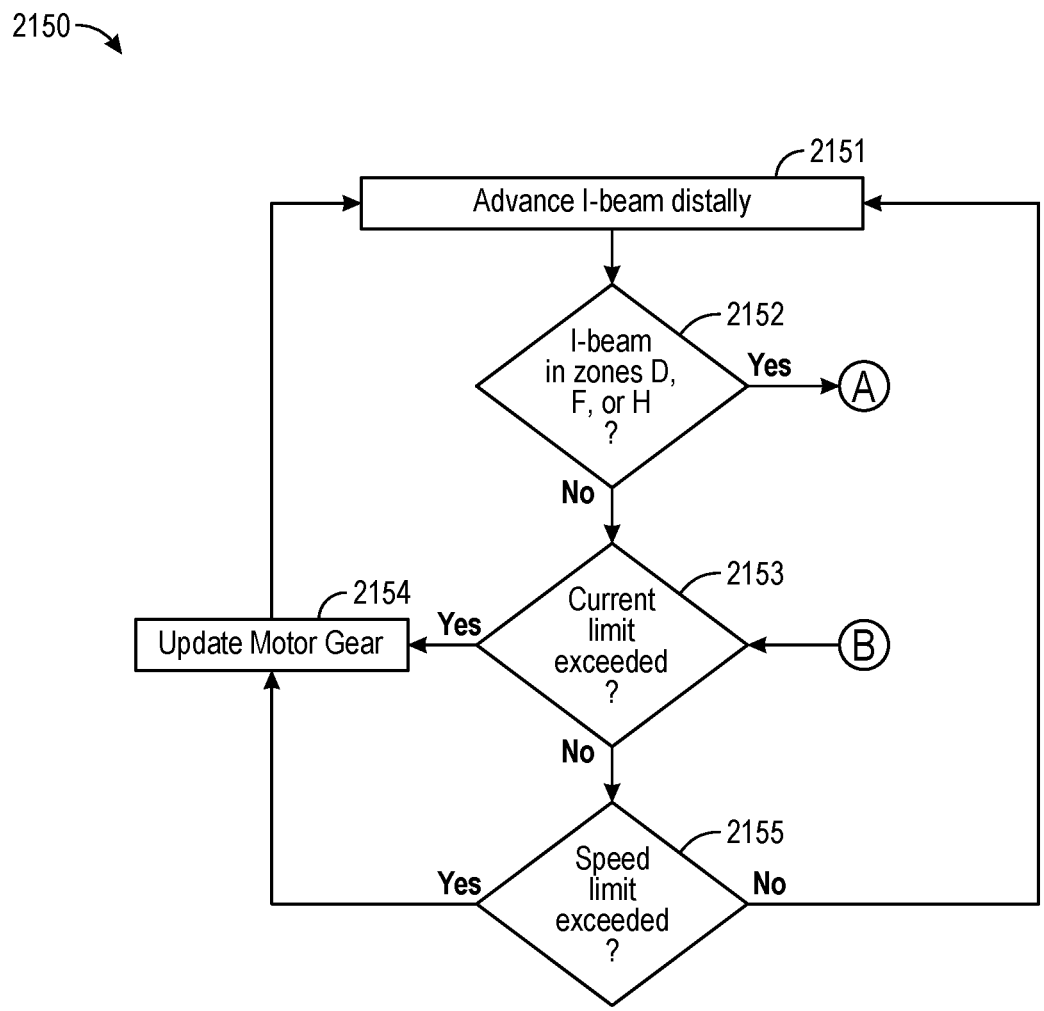
FIG. 21 is a flow diagram illustrating a method for controlling stapling speed in accordance with various embodiments of the present technology.

FIG. 21 is a flow diagram illustrating a method 2150 in accordance with various embodiments of the present technology. In some embodiments, the method 2150 can be employed to control stapling speed of a surgical stapler based on resistance feedback (e.g., current observed in a drivetrain of a surgical handle assembly of the surgical stapler, speed of the electric motor). In some embodiments, the method 2150 can be employed while an electric motor of a surgical handle assembly is used to distally advance an I-beam of an attached reloadable cartridge assembly outside of, for example, zones B, D, F, and/or H of FIGS. 15 and 16. For example, the method 2150 can be employed while an electric motor of a surgical handle assembly is used to distally advance an I-beam of an attached reloadable cartridge assembly across zones A, C, E, and/or G of FIGS. 15 and/or 16. In these and other embodiments, the method 2150 can be employed to distinguish between (i) resistive feedback from tissue clamped between a first elongated member and a second elongated member of the reloadable cartridge assembly and through which the I-beam can be advanced (e.g., to cut and staple the tissue) and (ii) resistive feedback corresponding to an obstacle (e.g., that poses as a hazard). In these and still other embodiments, the method 2150 can be used to set a virtual gear of an electric motor, a target speed for the electric motor, and/or a current limit for a corresponding drivetrain (e.g., for use while the I-beam is advanced through one or more zones in which it is not likely or expected that the I-beam will encounter an obstacle). Additionally, or alternatively, the method 2150 can be employed while an electric motor of a surgical handle assembly is used to proximally retract an I-beam of an attached reloadable cartridge assembly (e.g., within or across one or more of zones A-H of FIGS. 15 and/or 16). In these and other embodiments, the method 2150 can be employed to determine when to stall the electric motor and/or abort firing the reloadable cartridge assembly.

The method 2150 is illustrated as a set of steps or blocks 2151-2155. All or a subset of one or more of the blocks 2151-2155 can be executed by various components of a surgical stapling system, such as by a surgical handle assembly and/or a reloadable cartridge assembly. For example, all or a subset of one or more of the blocks 2151-2155 can be executed by a microcontroller, an electric motor, a drivetrain, a gear rack, a drive shaft, a blade assembly, an I-beam, a first elongated member, and/or a second elongated member. Furthermore, all or a subset of one or more of the blocks 2151-2155 can be executed by a user or operator of the surgical stapling system. Moreover, all or a subset of one or more of the blocks 2151-2155 can be executed in accordance with the discussion above. The method 2150 is discussed in detail below with repeated reference to the LUT 1410 of FIG. 14 and to zones A-H of FIGS. 15 and/or 16. The method 2150 is also discussed in detail below under the assumptions (i) that zeroing of the encoder information (e.g., similar to the process described above with reference to block 1721 of the method 1720 of FIG. 17) has already been performed and (ii) that the method 2150 is not used for advancing the I-beam across zone B and/or does not begin at block 2151 when the I-beam is positioned within zone B of FIGS. 15 and 16.

The method 2150 can begin at block 2151 by advancing the I-beam distally. Advancing the I-beam distally can include clamping the first elongated member and the second elongated member together (e.g., such that the first elongated member and the second elongated member clamp down on and/or hold tissue between the first elongated member and the second elongated member). Advancing the I-beam distally can include advancing the I-beam distally using a drivetrain, electric motor, gear rack, and/or drive shaft of the surgical handle assembly and/or a blade assembly of the reloadable cartridge assembly. Advancing the I-beam distally can include setting and/or controlling a virtual gear of the electric motor, such as using a LUT (e.g., the LUT 1410 of FIG. 14). Advancing the I-beam distally can include setting and/or controlling a current limit for the drivetrain and/or a target speed for the electric motor. Advancing the I-beam distally can include (e.g., continuously or periodically) tracking a position (e.g., a current position) of the I-beam, such as using encoder information generated by and/or received from the encoder and/or relative to an initial position or another location (in accordance with the discussion above). In these and other embodiments, advancing the I-beam distally can include tracking and/or recording the position of the I-beam over time, tracking and/or recording measurements of current observed in the drivetrain over time, and/or tracking and/or recording speeds of the electric motor over time. Advancing the I-beam distally can include advancing the I-beam distally through one or more of zone A, zone C, zone D, zone E, zone F, zone G, and/or zone H. In some zones (e.g., zones C, D, E, F, G, and/or H), advancing the I-beam distally can include cutting and/or stapling tissue held between the first elongated member and the second elongated member.

At block 2152, the method 2150 can continue by determining whether the I-beam is currently positioned within zones D, F, or H. In some embodiments, determining whether the I-beam is currently positioned within zones D, F, or H includes monitoring encoder information generated by and/or received from the encoder and/or determining a position (e.g., a current position) of the I-beam based at least in part on the encoder information. In the event the I-beam is currently positioned within zones D, F, or H (block 2152: Yes), the method 2150 can proceed to block 2261 of method 2260 discussed in greater detail below with reference to FIG. 22. On the other hand, in the event the I-beam is not currently positioned within zones D, F, or H (block 2152: No), the method 2150 can proceed to block 2153. For example, the method 2150 can proceed to block 2153 when the I-beam is currently positioned within zones C, E, G, and/or A of FIGS. 15 and/or 16.

At block 2153, the method 2150 can continue by determining whether current observed in the drivetrain exceeds (or meets) a current limit corresponding to a present virtual gear of the electric motor. For example, referring to the LUT 1410 of FIG. 14 and assuming that the electric motor is presently in virtual gear 4, determining whether the current observed in the drivetrain exceeds (or meets) the current limit can include comparing current observed in the drivetrain to the current limit D that corresponds to virtual gear 4 in the LUT 1410. Continuing with this example, in the event the method 2150 determines that the current observed in the drivetrain does not exceed (or meet) the current limit D (block 2153: No), the method 2150 can proceed to block 2155.

On the other hand, in the event the method 2150 determines that the current observed in the drivetrain exceeds (or meets) the current limit D (block 2153: Yes), the method 2150 can proceed to block 2154. In some embodiments, before proceeding to block 2154 after determining that the current observed in the drivetrain exceeds (or meets) a current limit for a present virtual gear of the electric motor, the method 2150 can determine whether the current observed in the drivetrain corresponds to a spike in the current observed in the drivetrain and/or is accompanied by little to no change in a position of the I-beam. In the event the method 2150 determines that the current observed in the drivetrain corresponds to a spike in the current observed in the drivetrain and/or is accompanied by little to no change in a position of the I-beam, the method 2150 can (e.g., in a manner generally similar to block 1729 of the method 1720 of FIG. 17) determine that the surgical stapler (e.g., the I-beam) has encountered an obstacle, can abort/stall further distal advancement of the I-beam, and/or can alert a user/operator.

At block 2155, the method 2150 can continue by determining whether a speed of the electric motor exceeds (or meets) a target speed/speed limit corresponding to a present virtual gear of the electric motor. For example, referring to the LUT 1410 of FIG. 14 and assuming that the electric motor is presently in virtual gear 4, determining whether the speed of the electric motor exceeds (or meets) the target speed can include comparing the speed of the electric motor to the target speed D that corresponds to virtual gear 4 in the LUT 1410. In these and other embodiments, determining whether the speed of the electric motor exceeds (or meets) the target speed can include determining whether the speed of the electric motor exceeds (or meets) the target speed D for more than a threshold amount of time (e.g., within a window). Continuing with this example, in the event the method 2150 determines that the speed of the electric motor does not exceed (or meet) the target speed D (block 2155: No), the method 2150 can return to block 2151.

On the other hand, in the event the method 2150 determines that the speed of the electric motor exceeds (or meets) the target speed D (block 2155: Yes), the method 2150 can proceed to block 2154. In some embodiments, before proceeding to block 2154 after determining that the speed of the electric motor exceeds (or meets) a target speed for a present virtual gear of the electric motor, the method 2150 can determine whether the speed of the electric motor corresponds little to no change in a position of the I-beam and/or to a sudden drop in the current observed in the drivetrain. In the event the method 2150 determines that the speed of the electric motor corresponds little to no change in a position of the I-beam and/or to a sudden drop in the current observed in the drivetrain, the method 2150 can (e.g., in a manner generally similar to block 1729 of the method 1720 of FIG. 17) determine that the surgical stapler (e.g., the I-beam) has encountered a problem (e.g., there is a break in the link between the gear shaft and the I-beam, tissue has slipped out from between the first elongated member and the second elongated member, etc.), can abort/stall further distal advancement of the I-beam, and/or can alert a user/operator.

At block 2154, the method 2150 can continue by updating a virtual gear of the electric motor. In some embodiments, updating the virtual gear of the electric motor can include updating the virtual gear using a LUT, such as the LUT 1410 of FIG. 14. For example, when the method 2150 proceeds to block 2154 from block 2153 (e.g., after determining that current observed in the drivetrain exceeds or meets a current limit corresponding to a present virtual gear of the electric motor), updating the virtual gear can include increasing the virtual gear of the electric motor, such as to a next higher virtual gear in the LUT or to another virtual gear in the LUT (e.g., a virtual gear corresponding to a current limit that exceeds the current observed in the drivetrain). As a specific example, when virtual gear 4 from the LUT 1410 of FIG. 14 is the present virtual gear for the electric motor and the method 2150 proceeds to block 2154 from block 2153, the method 2150 can update the virtual gear of the electric motor to virtual gear 5 or some other higher virtual gear in the LUT 1410. As discussed above with reference to FIG. 14, updating the virtual gear of the electric motor to a higher virtual gear can increase a current limit for current in the drivetrain (e.g., to increase power provided to cut/staple tissue) while decreasing a target speed for the electric motor to decrease stapling speed.

As another example, when the method 2150 proceeds to block 2154 from block 2155 (e.g., after determining that the speed of the electric motor exceeds or meets a target speed corresponding to a present virtual gear of the electric motor), updating the virtual gear can include decreasing the virtual gear of the electric motor, such as to a next lower virtual gear in the LUT or to another virtual gear in the LUT (e.g., a virtual gear corresponding to a target speed that exceeds the speed of the electric motor). As a specific example, when virtual gear 4 from the LUT 1410 of FIG. 14 is the present virtual gear for the electric motor and the method 2150 proceeds to block 2154 from block 2155, the method 2150 can update the virtual gear of the electric motor to virtual gear 3 or some other lower virtual gear in the LUT 1410. As discussed above with reference to FIG. 14, updating the virtual gear of the electric motor to a lower virtual gear can increase a target speed for the electric motor to increase stapling speed while decreasing a current limit for current in the drivetrain (e.g., to lower power provided to cut/staple tissue).

Although the steps 2151-2155 of the method 2150 are discussed and illustrated in a particular order, the method 2150 of FIG. 21 is not so limited. In other embodiments, the steps 2151-2155 of the method 2150 can be performed in a different order. In these and other embodiments, any of the steps 2151-2155 of the method 2150 can be performed before, during, and/or after any of the other steps 2151-2155 of the method 2150. For example, the I-beam can be advanced distally (block 2151) before, during, and/or after executing all or a subset of blocks 2152-2155. As another example, block 2155 can be executed before or while executing block 2153. Furthermore, a person of ordinary skill in the relevant art will recognize that the illustrated method 2150 can be altered and still remain within these and other embodiments of the present technology. For example, one or more of the blocks 2151-2155 of the method 2150 illustrated in FIG. 21 can be omitted and/or repeated (e.g., all or a subset of one or more of blocks 2151-2155) in some embodiments. Moreover, although discussed in detail above with reference to advancing an I-beam distally through zones A, C, E, and/or G, all or a subset of one or more of the blocks 2151-2155 can be performed (i) while retracting an I-beam proximally through the zones A, C, E, and/or G, and/or (ii) while retracting an I-beam proximally through one or more other zones, such as zones at ends of strokes (e.g., zones D, F, and H of FIGS. 15 and 16), and/or (iii) while retracting an I-beam proximally through zone B.

Additionally, or alternatively, the method 2150 can include additional blocks than shown in FIG. 21. As a specific example, the method 2150 can include a block at which the method 2150 determines whether current observed in the drivetrain has dropped below (or meets) another current limit (e.g., a low current limit corresponding to a present virtual gear of the electric motor). In the event the method 2150 determines that current observed in the drivetrain has dropped below or meets the other current limit, the method 2150 can proceed to update the virtual gear of the electric motor, such as using a LUT. Updating the virtual gear of the electric motor in this scenario can include decreasing the virtual gear of the electric motor. As discussed above, decreasing the virtual gear can decrease a current limit for current in the drivetrain (e.g., to lower power provided to cut/staple tissue) and/or can increase a target speed for the electric motor (e.g., increase stapling speed).

As another specific example, the method 2150 can include a block at which the method 2150 determines whether the speed of the electric motor has dropped below (or meets) another target speed (e.g., a low target speed corresponding to a present virtual gear of the electric motor). In the event the method 2150 determines that the speed of the electric motor has dropped below or meets the other target speed, the method 2150 can proceed to update the virtual gear of the electric motor, such as using a LUT. Updating the virtual gear of the electric motor in this scenario can include increasing the virtual gear of the electric motor. As discussed above, increasing the virtual gear can increase a current limit for current in the drivetrain (e.g., to increase power provided to cut/staple tissue) and/or can decrease a target speed for the electric motor (e.g., decrease stapling speed).

Figure 22:
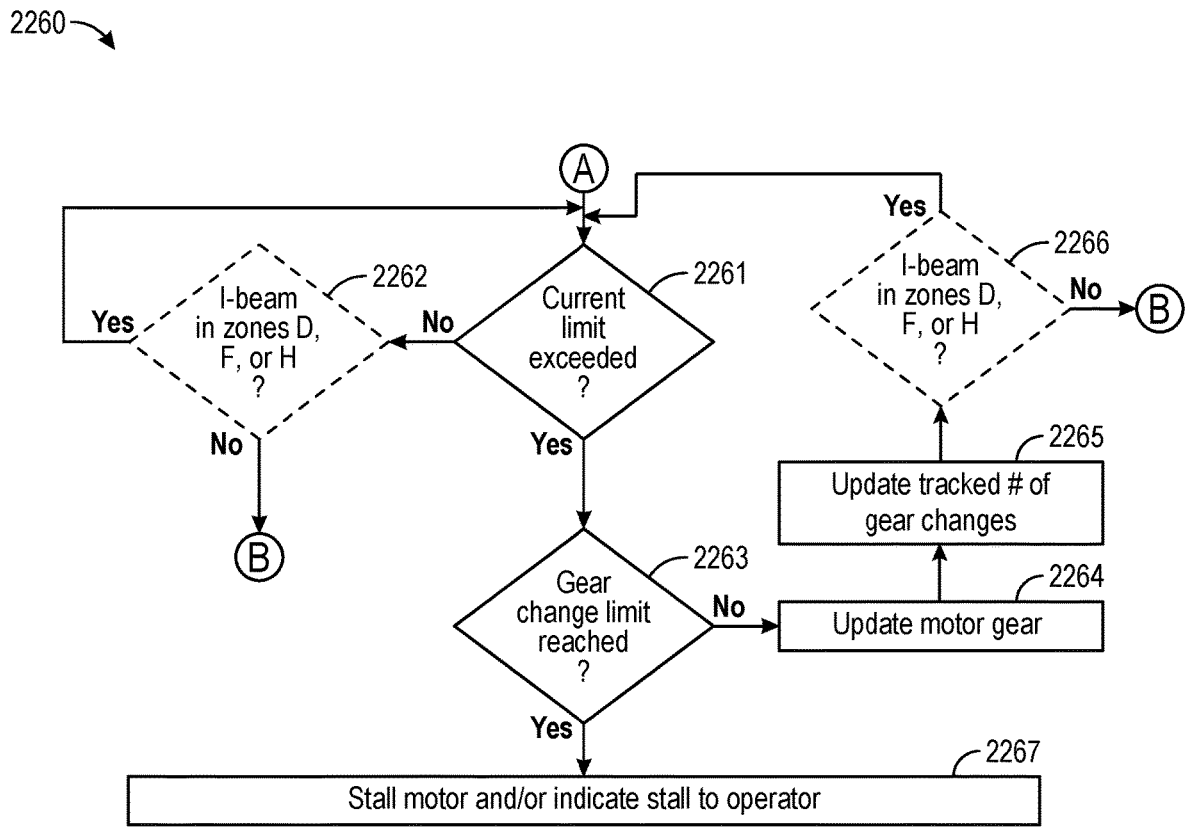
FIG. 22 is a flow diagram illustrating an end-of-reload detection method in accordance with various embodiments of the present technology.

FIG. 22 is a flow diagram illustrating a method 2260 in accordance with various embodiments of the present technology. In some embodiments, the method 2260 can be employed to control stapling speed of a surgical stapler based on resistance feedback (e.g., current observed in a drivetrain of a surgical handle assembly of the surgical stapler, speed of the electric motor). In some embodiments, the method 2260 can be employed while an electric motor of a surgical handle assembly is used to distally advance an I-beam of an attached reloadable cartridge assembly through or across, for example, zones D, F, and/or H of FIGS. 15 and 16. In these and other embodiments, the method 2260 can be employed to distinguish between (i) resistive feedback from tissue clamped between a first elongated member and a second elongated member of the reloadable cartridge assembly and through which the I-beam can be advanced (e.g., to cut and staple the tissue) and (ii) resistive feedback corresponding to an obstacle (e.g., an EOS obstacle, and/or against which there is a risk of damaging the reloadable cartridge assembly and/or tissue if attempts to advance the I-beam distally continue). In these and still other embodiments, the method 2260 can be used to set a virtual gear of an electric motor, a target speed for the electric motor, and/or a current limit for a corresponding drivetrain (e.g., for use while the I-beam is advanced through zones D, F, and/or G and/or another zone in which it is likely or expected that the I-beam can or will encounter an obstacle). Additionally, or alternatively, the method 2260 can be employed to detect when (i) an I-beam has reached its end of stroke and/or (ii) an I-beam encounters an EOS obstacle (e.g., a wall of the reloadable cartridge assembly) or another obstacle. In these and other embodiments, the method 2260 can be employed to determine when to stall the electric motor and/or stop attempts at further firing of the reloadable cartridge assembly. In these and still other embodiments, the method 2260 can be employed while an electric motor of a surgical handle assembly is used to proximally retract an I-beam of an attached reloadable cartridge assembly (e.g., within or across one or more of zones A-H of FIGS. 15 and/or 16).

The method 2260 is illustrated as a set of steps or blocks 2261-2267. All or a subset of one or more of the blocks 2261-2267 can be executed by various components of a surgical stapling system, such as by a surgical handle assembly and/or a reloadable cartridge assembly. For example, all or a subset of one or more of the blocks 2261-2267 can be executed by a microcontroller, an electric motor, a drivetrain, a gear rack, a drive shaft, a blade assembly, an I-beam, a first elongated member, and/or a second elongated member. Furthermore, all or a subset of one or more of the blocks 2261-2267 can be executed by a user or operator of the surgical stapling system. Moreover, all or a subset of one or more of the blocks 2261-2267 can be executed in accordance with the discussion above. The method 2260 is discussed in detail below with repeated reference to the LUT 1410 of FIG. 14 and to zones D, F, and H of FIGS. 15 and/or 16. The method 2260 is also discussed in detail below under the assumptions (i) that zeroing of the encoder information (e.g., similar to the process described above with reference to block 1721 of the method 1720 of FIG. 17) has already been performed, and (ii) that the method 2260 begins after determining (e.g., using the encoder information and/or at block 2152 of the method 2150 of FIG. 21) that the I-beam is currently positioned within zone D, F, or H and/or another zone in which it is likely or expected that the I-beam will reach its end of stroke and/or encounter an EOS obstacle or another obstacle.

The method 2260 can begin at block 2261 by determining whether current observed in the drivetrain exceeds (or meets) a current limit corresponding to a present virtual gear of the electric motor, such as using a LUT. For example, referring to the LUT 1410 of FIG. 14 and assuming that the electric motor is presently in virtual gear 4, determining whether the current observed in the drivetrain exceeds (or meets) the current limit can include comparing current observed in the drivetrain to the current limit D that corresponds to virtual gear 4 in the LUT 1410. Continuing with this example, in the event the method 2260 determines that the current observed in the drivetrain does not exceed (or meet) the current limit D (block 2261: No), the method 2260 can optionally proceed to block 2262 or to block 2261. On the other hand, in the event the method determines that the current observed in the drivetrain exceeds (or meets) the current limit D (block 2261: Yes), the method 2260 can proceed to block 2263. In some embodiments, determining whether current observed in the drivetrain exceeds (or meets) a current limit corresponding to a present virtual gear of the electric motor can include determining whether current observed in the drivetrain exceeds (or meets) a current limit corresponding to a present virtual gear of the electric motor while advancing the I-beam through zone D, F, and/or H, and/or while cutting and/or stapling the tissue held between the first elongated member and the second elongated member.

At block 2262, the method 2260 can continue by determining whether the I-beam is currently positioned within zones D, F, or H. In some embodiments, determining whether the I-beam is currently positioned within zones D, F, or H includes monitoring encoder information generated by and/or received from the encoder and/or determining a position (e.g., a current position) of the I-beam based at least in part on the encoder information. In the event the method 2260 determines the I-beam is currently positioned within zones D, F, or H (block 2262: Yes), the method 2260 can return to block 2261. On the other hand, in the event the method 2260 determines the I-beam is not currently positioned within zones D, F, or H (block 2262: No), the method 2260 can (i) determine that the I-beam was retracted proximally out of zone D, F, or H into another zone, (ii) determine that the I-beam was advanced distally beyond zone D, F, and/or H, and/or (iii) proceed to block 2153 of the method 2150 of FIG. 21. In some embodiments, in the event the method 2260 determines that the I-beam is not currently positioned within zones D, F, or H (block 2262: No), the method 2260 can reset a tracked number of virtual gear changes for the electric motor (described in greater detail below), such as before proceeding to block 2153 of the method 2150.

At block 2263, the method 2260 can continue by determining whether a gear change limit or threshold has been reached. In some embodiments, the method 2260 can track a number of virtual gear changes (e.g., a number of updates to the virtual gear of the electric motor, such as a number of virtual gear increases, a number of virtual gear decreases, or a total number of virtual gear increases in combination with virtual gear decreases) for the electric motor while the I-beam is (e.g., continuously) positioned within zone D, F, or H. In these and other embodiments, the gear change limit can correspond to a maximum number of permitted virtual gear changes (e.g., a maximum number of virtual gear increases, a maximum number of virtual gear decreases, or a maximum total number of virtual gear increases in combination with virtual gear decreases) for the electric motor while the I-beam is (e.g., continuously) positioned within zone D, F, or H. In these and still other embodiments, determining whether the gear change limit has been reached can include (i) comparing the tracked number of virtual gear changes to the gear change limit and (ii) determining whether the tracked number of virtual gear changes meets the gear change limit. In the event the method 2260 determines that the gear change limit has not been reached (block 2263: No), the method 2260 can proceed to block 2264.

At block 2264, the method 2260 can continue by updating a virtual gear of the electric motor. In some embodiments, updating the virtual gear of the electric motor can include updating the virtual gear using a LUT, such as the LUT 1410 of FIG. 14. For example, updating the virtual gear can include increasing the virtual gear of the electric motor, such as to a next higher virtual gear in the LUT or to another virtual gear in the LUT (e.g., a virtual gear corresponding to a current limit that exceeds the current observed in the drivetrain). As a specific example, when virtual gear 4 from the LUT 1410 of FIG. 14 is the present virtual gear for the electric motor and the method 2260 proceeds to block 2264 from block 2263, the method 2260 can update the virtual gear of the electric motor to virtual gear 5 or some other higher virtual gear in the LUT 1410. As discussed above with reference to FIG. 14, updating the virtual gear of the electric motor to a higher virtual gear can increase a current limit for current in the drivetrain (e.g., to increase power provided to cut/staple tissue) while decreasing a target speed for the electric motor to decrease stapling speed.

At block 2265, the method 2260 can continue by updating the tracked number of virtual gear changes for the electric motor. In some embodiments, updating the tracked number of virtual gear changes for the electric motor can include updating (e.g., increasing) the tracked number of virtual gear changes by one or another value.

At block 2266, the method 2260 can optionally continue by determining whether the I-beam is currently positioned within zones D, F, or H. Determining whether the I-beam is currently positioned within zones D, F, or H at block 266 can be generally similar to determining whether the I-beam is currently positioned within zones D, F, or H at block 262 discussed in detail above. In the event the method 2260 determines the I-beam is currently positioned within zones D, F, or H (block 2266: Yes), the method 2260 can return to block 2261. On the other hand, in the event the method 2260 determines the I-beam is not currently positioned within zones D, F, or H (block 2266: No), the method 2260 can (i) determine that the I-beam was retracted proximally out of zone D, F, or H into another zone, (ii) determine that the I-beam was advanced distally beyond zone D, F, and/or H, and/or (iii) proceed to block 2153 of the method 2150 of FIG. 21. In some embodiments, in the event the method 2260 determines that the I-beam is not currently positioned within zones D, F, or H (block 2267: No), the method 2260 can reset the tracked number of virtual gear changes for the electric motor, such as before proceeding to block 2153 of the method 2150.

Referring again to block 2263, in the event the method 2260 determines that the gear change limit has been reached (block 2263: Yes), the method 2260 can proceed to block 2267. At block 2267, the method 2260 can continue by (i) stalling (e.g., disabling, cutting power to, stop from driving) the electric motor such that attempts to distally advance the I-beam are ceased and/or (ii) indicating to a user/operator that an obstacle (e.g., an EOS obstacle) has been detected and/or that the I-beam has reached its end of stroke. The indication can be a visual indication (e.g., a specific color of light (e.g., red, yellow), a flashing or solid pattern of light(s), etc. emitted, for example, by an LED on the surgical handle assembly) and/or an audio indication (e.g., beeps or other sounds, such as of a specific frequency or pitch). In some embodiments, the method 2260 can retract the I-beam proximally by an amount before stalling the electric motor (e.g., to relieve force exerted on the EOS obstacle or another obstacle that caused the stall). In some embodiments, at this time, a user/operator can optionally retract the I-beam proximally.

Although the steps 2261-2267 of the method 2260 are discussed and illustrated in a particular order, the method 2260 of FIG. 22 is not so limited. In other embodiments, the steps 2261-2267 of the method 2260 can be performed in a different order. In these and other embodiments, any of the steps 2261-2267 of the method 2260 can be performed before, during, and/or after any of the other steps 2261-2267 of the method 2260. For example, block 2265 can be executed before, during, and/or after block 2264 and/or block 2266. Furthermore, a person of ordinary skill in the relevant art will recognize that the illustrated method 2260 can be altered and still remain within these and other embodiments of the present technology. For example, one or more of the blocks 2261-2267 of the method 2260 illustrated in FIG. 22 can be omitted (e.g. block 2267) and/or repeated (e.g., all or a subset of one or more of blocks 2261-2267) in some embodiments. Moreover, although discussed in detail above with reference to advancing an I-beam distally through zones D, F, and/or H, all or a subset of one or more of the blocks 2261-2267 can be performed (i) while retracting an I-beam proximally through zones D, F, and/or H, and/or (ii) while advancing an I-beam distally and/or retracting an I-beam proximally through one or more other zones (e.g., zones A, B, C, E, and/or G of FIGS. 15 and/or 16).

Additionally, or alternatively, the method 2260 can include additional blocks than shown in FIG. 22. As a specific example, the method 2260 can include a block at which the method 2260 determines whether a speed of the electric motor exceeds (or meets) a target speed/speed limit corresponding to a present virtual gear of the electric motor. For example, referring to the LUT 1410 of FIG. 14 and assuming that the electric motor is presently in virtual gear 4, determining whether the speed of the electric motor exceeds (or meets) the target speed can include comparing the speed of the electric motor to the target speed D that corresponds to virtual gear 4 in the LUT 1410. In these and other embodiments, determining whether the speed of the electric motor exceeds (or meets) the target speed can include determining whether the speed of the electric motor exceeds (or meets) the target speed D for more than a threshold amount of time (e.g., within a window). Continuing with this example, in the event the method 2260 determines that the speed of the electric motor exceeds (or meets) the target speed D, the method 2260 can proceed to block 2263.

As another specific example, the method 2260 can include a block at which the method 2260 determines whether current observed in the drivetrain has dropped below (or meets) another current limit (e.g., a low current limit corresponding to a present virtual gear of the electric motor). In the event the method 2260 determines that current observed in the drivetrain has dropped below or meets the other current limit, the method 2260 can proceed to block 2263 and/or can update the virtual gear of the electric motor, such as using a LUT. Updating the virtual gear of the electric motor in this scenario can include decreasing the virtual gear of the electric motor. As discussed above, decreasing the virtual gear can decrease a current limit for current in the drivetrain (e.g., to lower power provided to cut/staple tissue) and/or can increase a target speed for the electric motor (e.g., increase stapling speed).

As still another specific example, the method 2260 can include a block at which the method 2260 determines whether the speed of the electric motor has dropped below (or meets) another target speed (e.g., a low target speed corresponding to a present virtual gear of the electric motor). In the event the method 2260 determines that the speed of the electric motor has dropped below or meets the other target speed, the method 2260 can proceed to block 2263 and/or can update the virtual gear of the electric motor, such as using a LUT. Updating the virtual gear of the electric motor in this scenario can include increasing the virtual gear of the electric motor. As discussed above, increasing the virtual gear can increase a current limit for current in the drivetrain (e.g., to increase power provided to cut/staple tissue) and/or can decrease a target speed for the electric motor (e.g., decrease stapling speed).

Figure 23:
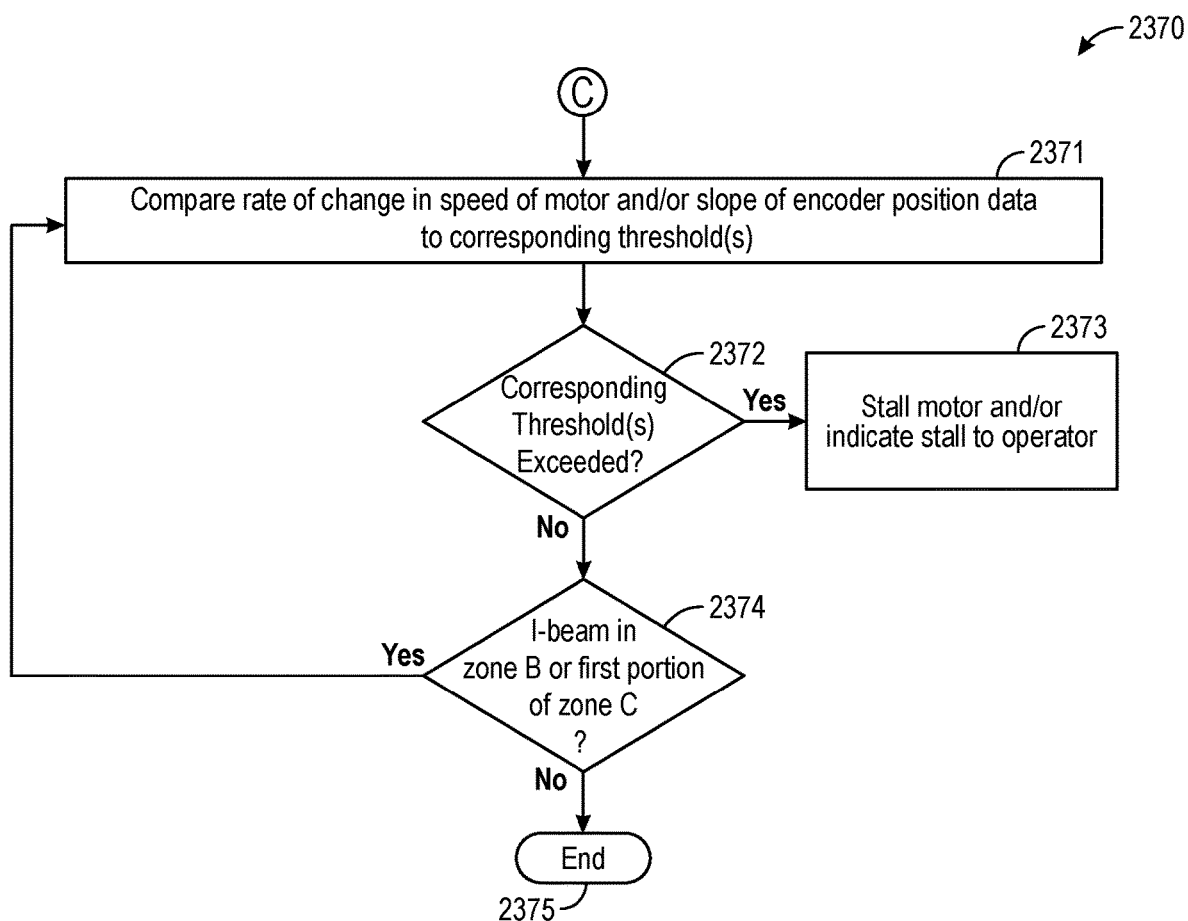
FIG. 23 is a flow diagram illustrating a mechanical failure detection method in accordance with various embodiments of the present technology.

FIG. 23 is a flow diagram illustrating a method 2370 in accordance with various embodiments of the present technology. In some embodiments, the method 2370 can be employed while an electric motor of a surgical handle assembly is used to distally advance an I-beam of an attached reloadable cartridge assembly, for example, through zones B and/or C of FIGS. 15 and 16. In these and other embodiments, the method 2370 can be employed to detect when there has been a mechanical failure in a surgical stapler system. For example, the method 2370 can be employed to distinguish between (i) resistive feedback from tissue clamped between a first elongated member and a second elongated member of the reloadable cartridge assembly and through which the I-beam can be advanced (e.g., to cut and staple the tissue) and (ii) resistive feedback corresponding to a failure of a triggered lockout mechanism (e.g., a mechanical latch) of a lockout assembly of the surgical stapler system (e.g., posing a risk of cutting tissue without stapling, such as because the reloadable cartridge assembly has been previously used or fired). In these and still other embodiments, the method 2370 can be employed to determine when to stall the electric motor and/or abort firing the reloadable cartridge assembly The method 2370 is illustrated as a set of steps or blocks 2371-2375. All or a subset of one or more of the blocks 2371-2375 can be executed by various components of a surgical stapling system, such as by a surgical handle assembly and/or a reloadable cartridge assembly. For example, all or a subset of one or more of the blocks 2371-2375 can be executed by a microcontroller, an electric motor, a drivetrain, a gear rack, a drive shaft, a blade assembly, an I-beam, a first elongated member, and/or a second elongated member. Furthermore, all or a subset of one or more of the blocks 2371-2375 can be executed by a user or operator of the surgical stapling system. Moreover, all or a subset of one or more of the blocks 2371-2375 can be executed in accordance with the discussion above. The method 2370 is discussed in detail below with repeated reference to zones B and C of FIGS. 15 and 16.

The method 2370 can begin at block 2371 by comparing a rate of change in the speed of the motor and/or a slope of encoder position data to one or more corresponding threshold values. Comparing the rate of change in the speed of the motor to a corresponding threshold value can include monitoring the speed of the motor over time and/or determining the rate of change in the speed of the motor. Additionally, or alternatively, comparing the slope of the encoder position data to a corresponding threshold value can include monitoring encoder information generated by and/or received from the encoder, determining and/or monitoring positions (e.g., current positions) of the I-beam over time and based at least in part on the encoder information, and/or determining the slope of (or rate of change in) the position of the I-beam.

As the I-beam is advanced distally through zone B and/or through at least a first or beginning portion of zone C of FIGS. 15 and 16, it is unlikely that speed increases of the motor and/or rapid changes in the position of the I-beam will be a result of varying tissue thickness or other motor driving algorithms of the present technology. Instead, due to the high probably of the I-beam encountering a lockout obstacle within zone B that is posed by a triggered lockout mechanism of a lockout assembly of the surgical stapling system, sudden speed increases in the motor and/or rapid changes in the position of the I-beam while the I-beam is positioned within zone B and/or within the first/beginning portion of zone C can indicate a mechanical failure in the surgical stapler system, such as a failure of the lockout mechanism preventing further distal movement of the I-beam along its stroke. For example, sudden speed increases and/or rapid changes in the position of the I-beam while the I-beam is positioned within zone B and/or within the first/beginning portion of zone C can indicate that the lockout mechanism posed a lockout obstacle to further distal advancement of the I-beam that the blade assembly was able to overcome or navigate about/through. Thus, in some embodiments, the one or more corresponding threshold values can be set at one or more levels at or above which there is a high probability that a mechanical failure has occurred within the surgical stapler system.

At block 2372, the method 2370 can continue by determining whether the rate of change in the speed of the motor and/or the slope of the encoder position data exceeds (or meets) the corresponding threshold value(s). In the event that the method 2370 determines that the rate of change in the speed of the motor and/or the slope of the encoder position data exceeds (or meets) the corresponding threshold value(s) (block 2372: Yes), the method 2370 can proceed to block 2373.

At block 2373, the method 2370 can continue by (i) stalling (e.g., disabling, cutting power to, stop from driving) the electric motor such that attempts to distally advance the I-beam are ceased, (ii) indicating to a user/operator that a mechanical failure has likely occurred in the surgical stapler system, (iii) indicating to a user/operator that a lockout mechanism of a lockout assembly of the surgical stapler system has failed, and/or (iv) indicating to a user/operator that a lockout obstacle has been overcome or navigated through/about. The indication can be a visual indication (e.g., a specific color of light (e.g., red, yellow), a flashing or solid pattern of light(s), etc. emitted, for example, by an LED on the surgical handle assembly) and/or an audio indication (e.g., beeps or other sounds, such as of a specific frequency or pitch).

Referring again to block 2372, in the event that the method 2370 determines that the rate of change in the speed of the motor and/or the slope of the encoder position data does not exceed (or meet) the corresponding threshold value(s) (block 2372: No), the method can proceed to block 2374. At block 2374, the method 2370 can continue by determining whether the I-beam is currently positioned within zone B or within a first/beginning portion of zone C. In some embodiments, determining whether the I-beam is currently positioned within zone B or the first/beginning portion of zone C can include determining whether the I-beam is currently positioned within a preset, predetermined, or fixed distance (e.g., approximately 1 mm) immediately distal to an end of zone B. For example, should the method 2370 determine that the I-beam is positioned within zone C and within the preset, predetermined, or fixed distance immediately distal to the end of zone B, the method 2370 can determine that the I-beam is currently positioned within zone B or the first/beginning portion of zone C (block 2374: Yes). Additionally, or alternatively, should the method 2370 determine that the I-beam is positioned within zone C but is not positioned within the preset, predetermined, or fixed distance immediately distal to the end of zone B, the method 2370 can determine that the I-beam is not currently positioned within zone B or the first/beginning portion of zone C for the purposes of block 2374 of the method 2370 (block 2374: No). In the event that the method 2370 determines that the I-beam is positioned within zone B or the first/beginning portion of zone C, the method 2370 can return to block 2371. On the other hand, in the event that the method 2370 determines that the I-beam is not positioned within zone B or the first/beginning portion of zone C, the method 2370 can proceed to block 2375 to terminate.

Although the steps 2371-2375 of the method 2370 are discussed and illustrated in a particular order, the method 2370 of FIG. 23 is not so limited. In other embodiments, the steps 2371-2375 of the method 2370 can be performed in a different order. In these and other embodiments, any of the steps 2371-2375 of the method 2370 can be performed before, during, and/or after any of the other steps 2371-2375 of the method 2370. For example, the method 2370 can perform a first instance of the block 2374 before performing a first instance of the block 2371. Furthermore, a person of ordinary skill in the relevant art will recognize that the illustrated method 2370 can be altered and still remain within these and other embodiments of the present technology. For example, one or more of the blocks 2371-2370 of the method 2370 illustrated in FIG. 23 can be omitted (e.g., block 2374) and/or repeated (e.g., all or a subset of one or more of blocks 2371-2374) in some embodiments. Moreover, although discussed in detail above with reference to advancing an I-beam distally through zone B and/or a first/beginning portion of zone C, all or a subset of one or more of the blocks 2371-2375 can be performed (i) while retracting an I-beam proximally through the zones B and/or the first/beginning portion of zone C, (ii) while advancing an I-beam distally and/or retracting an I-beam proximally through portions of zone C outside of the first/beginning portion of zone C, and/or (iii) while advancing an I-beam distally and/or retracting an I-beam proximally through one or more other zones, such as zones A, D, E, F, G, and/or H of FIGS. 15 and 16. In embodiments in which advancing the I-beam distally includes advancing the I-beam distally through another zone in addition to or in lieu of zone A, zone B and/or the first/beginning portion of zone C, advancing the I-beam distally can include cutting and/or stapling the tissue held between the first elongated member and the second elongated member.

Many embodiments or aspects of the present technology described herein can take the form of computer- or processor-executable instructions, including routines executed by a programmable computer or processor. For example, the present technology described herein can take the form of (e.g., non-transitory) computer readable media (e.g., memory devices, storage devices, disk drives, and/or other storage media) including computer- and/or processor-executable instructions stored thereon that, when executed by a processor and/or a computing device, cause systems to perform one or more of the methods described herein. Those skilled in the relevant art will appreciate that the disclosed techniques can be practiced on computer or processor systems other than those shown and described herein. The techniques described herein can be embodied in a special-purpose computer or data processor (e.g., a microcontroller, a controller, a microprocessor, etc.) that is specifically programmed, configured, or constructed to execute one or more of the computer-executable instructions described herein. Accordingly, the terms "computer," "controller," and "processor" as generally used herein refer to any data processor, and can include Internet appliances and handheld devices (including palm-top computers, wearable computers, cellular or mobile phones, multi-processor systems, processor-based or programmable consumer electronics, network computers, mini computers, and the like). Information handled by these computers and processors can be presented at any suitable display medium, including a liquid crystal display (LCD). Instructions for executing computer- or processor-executable tasks can be stored in or on any suitable computer-readable medium, including hardware, firmware, or a combination of hardware and firmware. Instructions can be contained in any suitable memory device, including, for example, a flash drive and/or other suitable medium. For example, suitable memory devices can include volatile and/or non-volatile memory. As more specific examples, the memory devices can include random access memory (RAM), electrically erasable programmable read-only memory (EEPROM), magnetic disks or tapes, and/or flash memory.

C. CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order above, alternative embodiments may perform steps in a different order. Furthermore, the various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any material incorporated herein by reference conflicts with the present disclosure, the present disclosure controls.

Where the context permits, singular or plural terms may also include the plural or singular term, respectively. In addition, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Furthermore, as used herein, the phrase "and/or" as in "A and/or B" refers to A alone, B alone, and both A and B. Additionally, the terms "comprising," "including," "having," and "with" are used throughout to mean including at least the recited feature(s) such that any greater number of the same features and/or additional types of other features are not precluded. Moreover, as used herein, the phrases "based on," "depends on," "as a result of," and "in response to" shall not be construed as a reference to a closed set of conditions. For example, an exemplary step that is described as "based on condition A" may be based on both condition A and condition B without departing from the scope of the present disclosure. In other words, as used herein, the phrase "based on" shall be construed in the same manner as the phrase "based at least in part on" or the phrase "based at least partially on."

From the foregoing, it will also be appreciated that various modifications may be made without deviating from the disclosure or the technology. For example, one of ordinary skill in the art will understand that various components of the technology can be further divided into subcomponents, or that various components and functions of the technology may be combined and integrated. In addition, certain aspects of the technology described in the context of particular embodiments may also be combined or eliminated in other embodiments. Furthermore, although advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

Furthermore, although several aspects of the present technology are discussed with reference to and set forth in examples of the present technology directed to—systems, devices, and/or methods of the present technology, these aspects of the present technology can similarly be discussed with reference to—and be set forth in examples of the present technology directed to—any of systems, devices, methods, and/or (e.g., non-transitory) computer-readable media. As such, aspects of the present technology are not limited to the form (e.g., system, device, method, computer-readable medium) in which they are presented and described above.

What is claimed is:

1. A method of operating a surgical stapler, the method comprising:
    tracking a position of a distal end of a blade assembly of a reloadable cartridge assembly of the surgical stapler as the distal end of the blade assembly is moved, via actuation of a motor and a corresponding drivetrain, along a stroke of the blade assembly; and
    adjusting a current limit for current levels in the drivetrain based at least in part on the position of the distal end of the blade assembly along the stroke.

2. The method of claim 1 wherein adjusting the current limit includes determining that the distal end of the blade assembly is positioned in a region along the stroke within which a lockout obstacle is anticipated to prevent further distal movement of the distal end of the blade assembly along the stroke.

3. The method of claim 2 wherein adjusting the current limit further includes setting the current limit to a predetermined value corresponding to a predetermined virtual gear for the motor for when the distal end blade assembly is positioned in the region.

4. The method of claim 2 wherein adjusting the current limit further includes setting the current limit based on a prediction of a current level that will be observed in the drivetrain when the distal end of the blade assembly is moved to an end or another point within the region.

5. The method of claim 4 wherein adjusting the current limit further includes generating the prediction based at least in part on a slope of a curve representing previous current levels observed in the drivetrain versus previous corresponding positions of the distal end of the blade assembly along the stroke.

6. The method of claim 4 wherein adjusting the current limit further includes generating the prediction based at least in part on an extrapolation of a curve to the end or the other point within the region, wherein the curve represents previous current levels observed in the drivetrain versus previous corresponding positions of the distal end of the blade assembly along the stroke.

7. The method of claim 4 wherein the current level is a first current level, and wherein adjusting the current limit further includes adjusting the current limit to a second current level greater than the first current level.

8. The method of claim 2, further comprising:
after adjusting the current limit, determining that a current level in the drivetrain exceeds the current limit; and
detecting engagement of a lockout assembly of the reloadable cartridge assembly based at least in part on the determination that the current level in the drivetrain exceeds the current limit.

9. The method of claim 8, wherein:
determining that the current level in the drivetrain exceeds the current limit includes detecting a spike in the current levels in the drivetrain;
the method further comprises, after adjusting the current limit, determining that the position of the distal end of the blade assembly remained approximately unchanged during a period of time corresponding to the spike in the current levels in the drivetrain; and
wherein detecting the engagement of the lockout assembly is further based at least in part on detection of the spike in the current levels in the drivetrain and the determination that the position of the distal end of the blade assembly remained approximately unchanged during the period of time.

10. The method of claim 8, further comprising:
stalling the motor based at least in part on detecting the engagement of the lockout assembly; or
providing an indication to a user that indicates detection of the engagement of the lockout assembly, wherein the indication includes an audible or visual indication.

11. The method of claim 1 wherein adjusting the current limit includes determining that the distal end of the blade assembly is positioned in a region along the stroke within which an end-of-stroke (EOS) obstacle is anticipated to prevent further distal movement of the distal end of the blade assembly along the stroke.

12. The method of claim 11, further comprising detecting the EOS obstacle, wherein detecting the EOS obstacle includes:
tracking, while the distal end of the blade assembly is positioned in the region, a number of times (a) the current limit is adjusted while the distal end of the blade assembly is positioned in the region, (b) a target speed for the motor is adjusted while the distal end of the blade assembly is positioned in the region, or (c) a virtual gear for the motor is adjusted; and
determining that the number of times has reached a predetermined limit.

13. The method of claim 12, further comprising:
stalling the motor based at least in part on detecting the EOS obstacle; or
providing an indication to a user that indicates detection of the EOS obstacle, wherein the indication includes an audible or visual indication.

14. The method of claim 1 wherein adjusting the current limit includes determining that the distal end of the blade assembly is positioned outside of (i) a first region along the stroke within which a lockout obstacle is anticipated to prevent further distal movement of the distal end of the blade assembly along the stroke and (ii) a second region along the stroke within which an end-of-stroke (EOS) obstacle is anticipated to prevent further distal movement of the distal end of the blade assembly along the stroke.

15. The method of claim 14 wherein adjusting the current limit further includes:
adjusting the current limit using a lookup table (LUT) that defines a plurality of virtual gears for the motor;
detecting (i) that a current level observed in the drivetrain violates the current limit, (ii) that a speed of the motor violates a target speed for the motor, or (iii) a first combination thereof, wherein the current limit and the target speed correspond to a first virtual gear for the motor defined in the LUT; and
updating the first virtual gear to a second virtual gear for the motor based at least in part on detecting that the current level violates the current limit corresponding to the first virtual gear, that the speed of the motor violates the target speed for the motor corresponding to the first virtual gear, or a second combination thereof.

16. The method of claim 14 wherein adjusting the current limit includes adjusting the current limit using a lookup table (LUT) that defines a plurality of virtual gears for the motor, wherein each of the plurality of virtual gears represents a pairing of a corresponding current limit with a corresponding target speed for the motor, and wherein current limits across the plurality of the virtual gears are generally inversely related to corresponding target speeds across the plurality of the virtual gears.

17. The method of claim 1 wherein:
tracking the position of the distal end of the blade assembly includes determining that the distal end of the blade assembly is positioned (i) in a region along the stroke within which a lockout obstacle is anticipated to prevent further distal movement of the distal end of the blade assembly along the stroke or (ii) within a threshold distance immediately distal to a distal end of the region; and
the method further comprises:
determining, while the distal end of the blade assembly is positioned in the region or within the threshold distance immediately distal to the distal end of the region, that a first rate of change in a speed of the motor or a second rate of change in the position of the distal end of the blade assembly exceeds a corresponding threshold value, and stalling the motor based at least in part on the determination that the first rate of change or the second rate of change exceeds the corresponding threshold value.

18. A surgical stapling system, comprising:
a surgical handle assembly including a motor and a corresponding drivetrain;
a reloadable cartridge assembly including a first elongated member, a second elongated member, and a blade assembly,
  wherein the reloadable cartridge assembly is releasably attachable to the surgical handle assembly such that the surgical handle assembly is useable to (i) clamp the first elongated member and the second elongated member together and (ii) move the blade assembly along a stroke of the blade assembly via actuation of the motor and the corresponding drivetrain;
at least one processor; and
at least one memory device operably coupled to the at least one processor and storing processor instructions that, when executed by the at least one processor, cause the surgical stapling system to perform operations comprising:
  tracking a position of a distal end of the blade assembly along the stroke of the blade assembly; and
  adjusting a current limit for current levels in the drivetrain based at least in part on the position of the distal end of the blade assembly along the stroke.

19. The surgical stapling system of claim 18 wherein the surgical handle assembly includes a processor of the at least one processor.

20. The surgical stapling system of claim 18, further comprising an encoder configured to generate encoder information usable to track the position of the distal end of the blade assembly along the stroke of the blade assembly.

21. A tangible, non-transient computer-readable medium having instructions stored thereon that, when executed by at least one processor, cause the at least one processor to perform a method, the method comprising:
  tracking a position of a distal end of a blade assembly of a reloadable cartridge assembly for a surgical stapler along a stroke of the blade assembly, wherein the distal end of the blade assembly is moveable along the stroke via actuation of a motor and a corresponding drivetrain of a surgical handle assembly to which the reloadable cartridge assembly is releasably attachable; and
  based at least in part on the position of the distal end of the blade assembly along the stroke, adjusting a target speed for the motor, a current limit for current levels in the drivetrain, or a combination thereof.

* * * * *